United States Patent
Lee et al.

(10) Patent No.: US 12,116,417 B2
(45) Date of Patent: *Oct. 15, 2024

(54) ANTI-HER2 ANTIBODY OR ANTIGEN-BINDING FRAGMENT THEREOF, AND CHIMERIC ANTIGEN RECEPTOR COMPRISING SAME

(71) Applicant: GC CELL CORPORATION, Yongin-si (KR)

(72) Inventors: Jong Seo Lee, Gyeonggi-do (KR); Kyu Tae Kim, Gyeonggi-do (KR); Young Ha Lee, Seoul (KR); In Sik Hwang, Incheon (KR); Bong Kook Ko, Seoul (KR)

(73) Assignee: GC Cell Corporation (KR)

( * ) Notice: Subject to any disclaimer, the term of this patent is extended or adjusted under 35 U.S.C. 154(b) by 939 days.

This patent is subject to a terminal disclaimer.

(21) Appl. No.: 16/764,276

(22) PCT Filed: Nov. 14, 2018

(86) PCT No.: PCT/KR2018/013928
§ 371 (c)(1),
(2) Date: Sep. 28, 2020

(87) PCT Pub. No.: WO2019/098682
PCT Pub. Date: May 23, 2019

(65) Prior Publication Data
US 2021/0179733 A1 Jun. 17, 2021

(30) Foreign Application Priority Data
Nov. 14, 2017 (KR) .................. 10-2017-0151841

(51) Int. Cl.
*C07K 16/32* (2006.01)
*A61K 35/17* (2015.01)
(Continued)

(52) U.S. Cl.
CPC .............. *C07K 16/32* (2013.01); *A61K 35/17* (2013.01); *A61P 35/00* (2018.01);
(Continued)

(58) Field of Classification Search
CPC ................ C07K 16/32; C07K 14/7051; C07K 14/70521; C07K 14/70578;
(Continued)

(56) References Cited

U.S. PATENT DOCUMENTS 4,554,101 A 11/1985 Hopp
5,783,186 A 7/1998 Arakawa et al.
(Continued)

FOREIGN PATENT DOCUMENTS

CA 2402930 3/2004
CN 104177499 12/2014
(Continued)

OTHER PUBLICATIONS

Sun et al., "Construction and evaluation of a novel humanized HER2-specific chimeric receptor," Breast Cancer Research, Jun. 11, 2014, 16:R61, 10 Pages.
(Continued)

*Primary Examiner* — Aurora M Fontainhas
*Assistant Examiner* — Selam Berhane
(74) *Attorney, Agent, or Firm* — Fish & Richardson P.C.

(57) ABSTRACT

The present disclosure relates to a novel anti-HER2 antibody or an antigen-binding fragment thereof used in the prevention or treatment of cancer, a chimeric antigen receptor including the same, and uses thereof. The antibody of the present disclosure is an antibody that specifically binds to HER2 which is highly expressed in cancer cells (particularly, breast cancer or gastric cancer cells), and binds to an epitope that is different from an epitope to which trastuzumab binds. When compared with trastuzumab, the
(Continued)

antibody of the present disclosure exhibits better killing ability for HER2-unexpressed cancer cells which have non-reactivity (or resistance) to the trastuzumab antibody or have reduced sensitivity. In addition, when the anti-HER2 antibody of the present disclosure is administered in combination with trastuzumab, a synergistic killing ability is achieved for cancer cells on which the trastuzumab antibody acts. Therefore, a composition of the present disclosure can be very usefully used for combined administration with the trastuzumab antibody for the treatment of cancer, or for the treatment of cancer not treated with trastuzumab.

24 Claims, 15 Drawing Sheets

Specification includes a Sequence Listing.

(51) Int. Cl.
| | | |
|---|---|---|
| *A61K 38/00* | (2006.01) | |
| *A61K 39/00* | (2006.01) | |
| *A61P 35/00* | (2006.01) | |
| *C07K 14/705* | (2006.01) | |
| *C07K 14/725* | (2006.01) | |
| *G01N 33/574* | (2006.01) | |

(52) U.S. Cl.
CPC .... *C07K 14/7051* (2013.01); *C07K 14/70521* (2013.01); *C07K 14/70578* (2013.01); *G01N 33/574* (2013.01); *A61K 38/00* (2013.01); *A61K 2039/5156* (2013.01); *A61K 2039/5158* (2013.01); *C07K 2317/24* (2013.01); *C07K 2317/565* (2013.01); *C07K 2317/92* (2013.01); *C07K 2319/02* (2013.01); *C07K 2319/03* (2013.01); *C07K 2319/30* (2013.01); *C07K 2319/33* (2013.01)

(58) Field of Classification Search
CPC .......... C07K 2317/24; C07K 2317/565; C07K 2317/92; C07K 2319/02; C07K 2319/03; C07K 2319/30; C07K 2319/33; A61P 35/00; A61K 35/17; A61K 38/00; A61K 2039/5156; A61K 2039/5158; G01N 33/574

See application file for complete search history.

(56) References Cited

U.S. PATENT DOCUMENTS

| | | | |
|---|---|---|---|
| 5,821,337 | A | 10/1998 | Carter et al. |
| 7,741,465 | B1 | 2/2010 | Eshhar et al. |
| 7,674,460 | B2 | 3/2010 | Serrero |
| 8,314,213 | B2 | 11/2012 | Bernett et al. |
| 8,404,811 | B2 | 3/2013 | Ye et al. |
| 9,079,976 | B2 | 7/2015 | Shirwan et al. |
| 9,394,368 | B2 | 7/2016 | Brogdon et al. |
| 9,624,276 | B2 | 4/2017 | Young et al. |
| 9,777,064 | B2 | 10/2017 | Wang et al. |
| 9,845,362 | B2 | 12/2017 | Mukherjee |
| 10,124,023 | B2 | 11/2018 | Brentjens et al. |
| 10,174,116 | B2 | 1/2019 | Lee et al. |
| 10,273,280 | B2 | 4/2019 | Ma et al. |
| 10,736,918 | B2 | 8/2020 | Jensen et al. |
| 11,197,919 | B2 | 12/2021 | Priceman et al. |
| 11,649,294 | B2 | 5/2023 | Lee et al. |
| 2009/0285837 | A1 | 11/2009 | Kao et al. |
| 2010/0183604 | A1 | 7/2010 | Ohta et al. |
| 2014/0199334 | A1 | 7/2014 | Sasikumar et al. |
| 2014/0255363 | A1 | 9/2014 | Metelitsa et al. |
| 2014/0294898 | A1 | 10/2014 | Miller et al. |
| 2014/0322275 | A1 | 10/2014 | Brogdon et al. |
| 2015/0125491 | A1 | 5/2015 | Sasikumar et al. |
| 2016/0130357 | A1 | 5/2016 | Mukherjee |
| 2016/0158285 | A1 | 6/2016 | Cooper et al. |
| 2016/0340391 | A1 | 11/2016 | Miller et al. |
| 2016/0340406 | A1 | 11/2016 | Zhao et al. |
| 2017/0107216 | A1 | 4/2017 | Wu et al. |
| 2017/0151281 | A1 | 6/2017 | Wagner et al. |
| 2017/0174679 | A1 | 6/2017 | Lajkiewicz et al. |
| 2017/0190786 | A1 | 7/2017 | Fendly et al. |
| 2017/0252432 | A1 | 9/2017 | Allen et al. |
| 2017/0313759 | A1 | 11/2017 | Batuwangala |
| 2017/0335281 | A1 | 11/2017 | Loew et al. |
| 2017/0362253 | A1 | 12/2017 | Xiao et al. |
| 2018/0057486 | A1 | 3/2018 | Wu et al. |
| 2018/0079824 | A1 | 3/2018 | Ahmed et al. |
| 2018/0326032 | A1 | 11/2018 | Priceman et al. |
| 2019/0037831 | A1 | 2/2019 | Hwang et al. |
| 2019/0336533 | A1 | 11/2019 | Hwang et al. |
| 2020/0038441 | A1 | 2/2020 | Klingemann et al. |
| 2020/0102366 | A1 | 4/2020 | Cooper et al. |
| 2020/0108096 | A1 | 4/2020 | Min et al. |
| 2020/0399397 | A1 | 12/2020 | Lee et al. |
| 2021/0008105 | A1 | 1/2021 | Martin |
| 2021/0040216 | A1 | 2/2021 | Chui et al. |
| 2021/0060070 | A1 | 3/2021 | Coughlin |
| 2021/0147803 | A1 | 5/2021 | Hwang et al. |
| 2022/0133663 | A1 | 5/2022 | Splichal |
| 2023/0025506 | A1 | 1/2023 | Hwang et al. |
| 2023/0303716 | A1 | 9/2023 | Lee et al. |

FOREIGN PATENT DOCUMENTS

| | | | |
|---|---|---|---|
| CN | 105246504 | 1/2016 | |
| CN | 105925536 | 9/2016 | |
| JP | 2010-006705 | 1/2010 | |
| JP | 2013-534809 | 9/2013 | |
| JP | 2016508725 | 3/2016 | |
| JP | 2016518368 | 6/2016 | |
| KR | 10-1453462 | 10/2014 | |
| KR | 10-2015-0048783 | 5/2015 | |
| KR | 10-2016-0015195 | 2/2016 | |
| KR | 10-2016-0022857 | 3/2016 | |
| KR | 10-2016-0062760 | 6/2016 | |
| WO | WO 1994/00136 | 1/1994 | |
| WO | WO-2006033700 A3 * | 9/2006 | ........... A61K 39/395 |
| WO | WO 2011/127297 | 10/2011 | |
| WO | WO 2013/094988 | 6/2013 | |
| WO | WO 2014/130657 | 8/2014 | |
| WO | WO 2014/185704 | 11/2014 | |
| WO | WO 2015/033299 | 3/2015 | |
| WO | WO 2015/033301 | 3/2015 | |
| WO | WO 2015/033303 | 3/2015 | |
| WO | WO 2015/034820 | 3/2015 | |
| WO | WO 2015/036927 | 3/2015 | |
| WO | WO 2015/044900 | 4/2015 | |
| WO | WO 2015/095895 | 6/2015 | |
| WO | WO 2015/160641 | 10/2015 | |
| WO | WO 2015/164594 | 10/2015 | |
| WO | WO 2016/039749 | 3/2016 | |
| WO | WO 2016/176639 | 3/2016 | |
| WO | WO 2016/077518 | 5/2016 | |
| WO | WO 2016/085248 | 6/2016 | |
| WO | WO 2016/090320 | 6/2016 | |
| WO | WO 2016/100608 | 6/2016 | |
| WO | WO 2016/120219 | 8/2016 | |
| WO | WO 2016/123333 | 8/2016 | |
| WO | WO 2016/126646 | 8/2016 | |
| WO | WO 2016/142833 | 9/2016 | |
| WO | WO 2016/142835 | 9/2016 | |
| WO | WO 2016/142852 | 9/2016 | |
| WO | WO 2016/142886 | 9/2016 | |
| WO | WO 2016/142894 | 9/2016 | |
| WO | WO 2016/154585 | 9/2016 | |
| WO | WO 2016/174652 | 11/2016 | |
| WO | WO 2016/191756 | 12/2016 | |
| WO | WO 2017/066227 | 4/2017 | |
| WO | WO 2017/070089 | 4/2017 | |
| WO | WO 2017/079694 | 5/2017 | |
| WO | WO 2017/079705 | 5/2017 | |

(56) References Cited

FOREIGN PATENT DOCUMENTS

| WO | WO-2017079694 A2 * | 5/2017 | ............ A61K 35/12 |
|---|---|---|---|
| WO | WO 2017/106634 | 6/2017 | |
| WO | WO 2017/118762 | 7/2017 | |
| WO | WO 2017/167967 | 10/2017 | |
| WO | WO 2017/176608 | 10/2017 | |
| WO | WO 2017/192961 | 11/2017 | |
| WO | WO 2017/202273 | 11/2017 | |
| WO | WO 2017/202275 | 11/2017 | |
| WO | WO 2017/202276 | 11/2017 | |
| WO | WO 2017/205464 | 11/2017 | |
| WO | WO 2017/222593 | 12/2017 | |
| WO | WO 2018/005374 | 1/2018 | |
| WO | WO 2018/006795 | 1/2018 | |
| WO | WO 2018/009505 | 1/2018 | |
| WO | WO 2018/013789 | 1/2018 | |
| WO | WO 2018/026971 | 2/2018 | |
| WO | WO 2018/044963 | 3/2018 | |
| WO | WO 2018/045142 | 3/2018 | |
| WO | WO 2018/051254 | 3/2018 | |
| WO | WO 2018/051255 | 3/2018 | |
| WO | WO 2018/140725 | 8/2018 | |
| WO | WO 2019/008152 | 1/2019 | |
| WO | WO 2019/008154 | 1/2019 | |
| WO | WO 2019/023575 | 1/2019 | |
| WO | WO 2019/030757 | 2/2019 | |
| WO | WO 2019/079564 | 4/2019 | |
| WO | WO 2019/160501 | 8/2019 | |
| WO | WO 2019/160956 | 8/2019 | |
| WO | WO 2019/182392 | 9/2019 | |
| WO | WO 2020/055040 | 3/2020 | |
| WO | WO 2020/069409 | 4/2020 | |
| WO | WO 2020/101361 | 5/2020 | |
| WO | WO 2021/071962 | 4/2021 | |
| WO | WO 2021/235894 | 11/2021 | |
| WO | WO 2022/133056 | 6/2022 | |
| WO | WO 2022/133057 | 6/2022 | |
| WO | WO 2022/133061 | 6/2022 | |
| WO | WO 2022/216144 | 10/2022 | |
| WO | WO 2022/216811 | 10/2022 | |
| WO | WO 2022/216813 | 10/2022 | |
| WO | WO 2022/216815 | 10/2022 | |
| WO | WO 2022/216826 | 10/2022 | |
| WO | WO 2022/216831 | 10/2022 | |
| WO | WO 2022/216837 | 10/2022 | |
| WO | WO 2023/080895 | 5/2023 | |
| WO | WO 2023/081317 | 5/2023 | |

OTHER PUBLICATIONS

International Preliminary Report on Patentability in International Appln. No. PCT/KR2021/006361, mailed on Dec. 1, 2022, 9 pages.
Office Action in Chinese Appln. No. 201880074007.4, dated Feb. 25, 2023, 15 pages (with English translation).
AU Office Action in Australian Appln. No. 2018370195, dated Jul. 6, 2021, 5 pages.
Extended European Search Report in European Patent Appln No. 18878132.2, dated Jul. 14, 2021, 10 pages.
Nahta et al., "The HER-2-Targeting Antibodies Transtuzumab and Pertuzumab Synergistically Inhibit the Survival of Breast Cancer Cells", Cancer Research, Apr. 2004, 64(7): 2343-2346.
Yamashita-Kashima et al., "Pertuzumab in Combination with Trastuzumab Shows Significantly Enhanced Antitumor Activity in HER2-Positive Human Gastric Cancer Xenograft Models", Clinical Cancer Research, Jun. 2011, 17(15):5060-5071.
Office Action in Indian Appln. No. 202017023032, dated Oct. 31, 2022, 6 pages.
U.S. Appl. No. 16/474,426, Hwang et al., filed Jun. 27, 2019.
U.S. Appl. No. 16/881,650, Lee et al., filed May 22, 2020.
U.S. Appl. No. 17/845,793, Hwang et al., filed Jun. 21, 2022.
Sadelain et al., "The Basic Principles of Chimeric Antigen Receptor Design," Cancer Discovery, Apr. 2013, 3:388-398.

Croft et al., "Regulation of T Cell Immunity by OX40 and OX40L," Madame Curie Bioscience Database, 2000-2013, retrieved on Jan. 12, 2022, retrieved from URL <"https://www.ncbi.nlm.nih.gov/books/NBK5990/">, 12 pages.
Webb et al., "OX40, OX40L and Autoimmunity: a Comprehensive Review," Clinic Rev. Allerg. Immunol., 2016, 50: 312-332.
International Search Report and Written Opinion in International Appln. No. PCT/KR2021/006361, dated Nov. 25, 2021, 14 pages.
U.S. Appl. No. 18/298,310, Lee et al., filed Apr. 10, 2023.
Hu et al., "Epitope mapping and structural analysis of an anti-ErbB2 antibody A21: Molecular basis for tumor inhibitory mechanism," Proteins, Feb. 15, 2008, 70(3):938-949.
Office Action in Japanese Appln. No. 2020-544730, dated Dec. 14, 2021, 11 pages (with English Translation).
Office Action in Japanese Appln. No. 2020-544730, dated May 23, 2022, 4 pages (with English Translation).
Rockberg et al., "Discovery of epitopes for targeting the human epidermal growth factor receptor 2 (HER2) with antibodies," Molecular Oncology, Jun. 2009, 3(3):238-247.
Akiyama et al., "The product of the human c-erbB-2 gene: a 185-kilodalton glycoprotein with tyrosine kinase activity," Science, Jun. 27, 1986, 232(4758):1644-1646.
Altschul et al., "Basic local alignment search tool," Journal of Molecular Biology, Oct. 5, 1990, 215(3):403-410.
Arteaga et al., "p185c-erbB-2 Signaling Enhances Cisplatin-induced Cytotoxicity in Human Breast Carcinoma Cells: Association between an Oncogenic Receptor Tyrosine Kinase and Drug-induced DNA Repair," Cancer Research, Jul. 1994, 54:3758-3765.
Bacus et al., "Differentiation of cultured human breast cancer cells (AU-565 and MCF-7) associated with loss of cell surface HER-2/neu antigen," Molecular Carcinogenesis, 1990, 3:350-362.
Bacus et al., "Tumor-inhibitory Monoclonal Antibodies to the HER-2/Neu Receptor Induce Differentiation of Human Breast Cancer Cells," Cancer Research, May 1992, 52:2580-2589.
Bussolati et al., "A modified Trastuzumab antibody for the immunohistochemical detection of HER-2 overexpression in breast cancer," British Journal of Cancer, Apr. 5, 2005, 92:1261-1267.
Corpet, "Multiple sequence alignment with hierarchical clustering," Nuc. Acids Res., Nov. 25, 1988, 16(22):10881-10890.
Crossland, "CD56-Specific T Cells; Using Genetically Engineered T Cells to Redirect Specificty to a T Cell Expressed Antigen" Dissertation for the degree of PhD, The University of Texas MD Anderson Cancer Center UTHealth Graduate School of Biomedical Sciences, Aug. 2014, 232 pages.
Gacerez et al., "How chimeric antigen receptor design affects adoptive T cell therapy" J. Cell Physiol., Dec. 2016, 231(12):2590-8.
GenBank Accession No. AB590584.1, "Synthetic construct DNA, clone: pFN21AE1768, *Homo sapiens* TNFRSF4 gene for tumor necrosis factor receptor superfamily, member 4, without stop codon, in Flexi system," Jul. 25, 2016, 2 pages.
GenBank Accession No. AF461811.1, "*Homo sapiens* NKG2D mRNA, complete cds" Jan. 17, 2002, 2 pages.
GenBank Accession No. N_000734.3, "*Homo sapiens* CD247 molecule (CD247), transcript variant 2, mRNA" Mar. 15, 2015, 5 pages.
GenBank Accession No. NM_001561.5, "*Homo sapiens* tumor necrosis factor receptor superfamily member 9 (TNFRSF9), mRNA" Nov. 20, 2015, 5 pages.
GenBank Accession No. NM_001768.6, "*Homo sapiens* CD8a molecule (CD8A), transcript variant 1, Mrna," Mar. 15, 2015, 4 pages.
GenBank Accession No. NM_003326.4, "*Homo sapiens* TNF superfamily member 4 (TNFSF4), transcript variant 1, mRNA" Nov. 21, 2015, 4 pages.
GenBank Accession No. NM_006139.3, "*Homo sapiens* CD28 molecule (CD28), transcript variant 1, mRNA," Mar. 15, 2015, 5 pages.
GenBank Accession No. X52645.1 "Human Fc-gamma RIII-2 cDNA for Fc-gamma receptor III-2 (CD16)," Oct. 7, 2008, 2 pages.
Glazyrin et al., "Direct Detection of Herceptin/Transtuzumab Binding on Breast Tissue Sections," J Histology & Cytochemistry, 2007, 55(1):25-33.

(56) References Cited

OTHER PUBLICATIONS

Hancock et al., "A Monoclonal Antibody against the c-erbB-2 Protein Enhances the Cytotoxicity of cis-Diamminedichloroplatinum against Human Breast and Ovarian Tumor Cell Lines," Cancer Res., Sep. 1, 1991, 51:4575-4580.
Harwerth et al., "Monoclonal Antibodies against the Extracellular Domain of erbB-2 Receptor Fuction as Partial Lgand Agonists," J Biol. Chem., Jul. 25, 1992, 267(21):15160-15167.
Higgins et al., "CLUSTAL: a packate for performing multiple sequence alignment on a microcomputer," Gene, 1988, 73:237-244.
Higgins et al., "Fast and sensitive multiple sequence alignments on a microcomputer," Cabios Commuications, 1989, 5(2):151-153.
Huang et al., "Parallelization of a local similarity algorithm," CABIOS, 1992, 8(2):155-165.
JP Office Action in Japanese Appln. No. 2020-544730, dated May 26, 2021, 12 pages (with English Translation).
Kasprzyk et al., "Therapy of an Animal Model of Human Gastric Cancer Using a Combination of Anti-erbB-2 Monoclonal Antibodies," Cancer Research, May 15, 1992, 52:2771-2776.
Klapper et al., "A subclass of tumor inhibitory monoclonal antibodies to ErbB-2/HER2 blocks crosstalk with growth factor receptors," Oncogene, Jan. 1997, 14:2099-2109.
Maier et al., "Requirements for the Internalization of a Murine Monoclonal Antibody Directed against the HER-2/neu Gene Product c-erbB-2," Cancer Res., Oct. 1, 1991, 51:5361-5369.
Needleman et al., "A General Method Applicable to the Search for Similarities in the Amino Acid Sequence of Two Proteins," J Mol. Biol., 1970, 48:443-453.
PCT International Preliminary Report on Patentability in International Appln. No. PCT/KR2018/013928, dated May 19, 2020, 17 pages (with English Translation).
PCT International Search Report and Written Opinion in International Appln. No. PCT/KR2018/013928, dated Mar. 15, 2019, 25 pages (with English Translation).
Ross et al., "The HER-2/neu Gene and Protein in Breast Cancer2003: Biomarker and Target of Therapy," The Oncologist, 2003, 8(4):307-325, 19 pages.
Sapino et al., "Patients with advanced stage breast carcinoma immunoreactive to biotinylated Herceptin® are most likely to benefit from trastuzumab-based therapy: an hypothesis-generating study," Annals of Oncology, Dec. 2007, 18(12):1963-1968, 6 pages.
Shawver et al., "Ligand-like Effects Induced by Anti-c-erbB-2 Antibodies Do Not Correlate with and Are Not Required for Growth Inhibition of Human Carcinoma Cells," Cancer Res., Mar. 1, 1994, 54:1367-1373.
Smith et al., "Comparison of biosequences," Adv. Appl. Math., Dec. 1981, 2(4):482-489.
Stancovski et al., "Mechanistic aspects of the opposing effects of monoclonal antibodies to the ERBB2 receptor on tumor growth," PNAS USA, Oct. 1, 1991, 88(19):8691-8695.
Tagliabue et al., "Selection of monoclonal antibodies which induce internalization and phosphorylation of P185HER2 and growth inhibition of cells with HER2/neu gene amplification," Int. J Cancer, Apr. 1, 1991, 47(6):933-937.
Uhlman et al., "Antisense oligonucleotides: a new therapeutic principle," Chemical Reviews, Jun. 1, 1990, 90(4):543-584.
Wilkie et al., "Retargeting of Human T Cells to Tumor-Associated MUC1: The Evolution of a Chimeric Antigen Receptor," The Journal of Immunology, 2008, 180:4901-9.
Xu et al., "Antibody-induced growth inhibition is mediated through immunochemically and functionally distinct epitopes on the extracellular domain of the c-erbb-2 (her-2/neu) gene product p185," Int. J Cancer, Feb. 1, 1993, 53:401-408.
U.S. Appl. No. 18/285,631, filed Oct. 4, 2023, Hwang et al.
U.S. Appl. No. 18/285,634, filed Oct. 4, 2023, Kim et al.
U.S. Appl. No. 18/285,636, filed Oct. 4, 2023, Lim et al.
Abou-Alfa et al., "Randomized phase II placebo controlled study of codrituzumab in previously treated patients with advanced hepatocellular carcinoma," J. Hepatol., Aug. 2016, 65(2):289-95.

Agus et al., "Phase I clinical study of pertuzumab, a novel HER dimerization inhibitor, in patients with advanced cancer," J. Clin. Oncol., Apr. 10, 2005, 23(11):2534-43.
Alizadeh et al., "IL15 Enhances CAR-T Cell Antitumor Activity by Reducing mTORC1 Activity and Preserving Their Stem Cell Memory Phenotype," Cancer Immunology Research, May 2019, 7(5):759-772.
Altschul et al., "Basic local alignment search tool," J. Mol. Biol., Oct. 5, 1990, 215(3):403-410.
Andre et al., "Anti-NKG2A mAb Is a Checkpoint Inhibitor that Promotes Anti-tumor Immunity by Unleashing Both T and NK Cells," Cell. Dec. 13, 2018;175(7):1731-1743.
Ataca et al., "Chimeric Antigen Receptor T Cell Therapy in Hematology," Turk J Hematol., 2015, 32:285-294.
Awada et al., "Abstract No. 2504: Results from a first-in-man, open label, safety and tolerability trial of CAN04 (nidanilimab), a fully humanized monoclonal antibody against the novel antitumor target, IL1RAP, in patients with solid tumors," Presented at ASCO 2019, Chicago, Illinois, May 31-Jun. 4, 2019, 14 pages.
Babic et al., "Pritumumab, the first therapeutic antibody for glioma patients," Hum Antibodies, Feb. 5, 2018, 26(2):95-101.
Bacigalupo et al., "Treatment of steroid resistant acute graft versus host disease with an anti-CD26 monoclonal antibody—Begelomab," Bone Marrow Transplant, Aug. 2020, 55(8):1580-1587.
Bajaj et al., "Conatumumab: a novel monoclonal antibody against death receptor 5 for the treatment of advanced malignancies in adults," Expert Opin. Biol. Ther., Nov. 2011, 11(11):1519-1524.
Baldo et al., "Amatuximab and novel agents targeting mesothelin for solid tumors," Onco Targets Ther., Nov. 2017, 10:5337-5353.
Bang et al., "First-in-human phase 1 study of margetuximab (MGAH22), an Fc-modified chimeric monoclonal antibody, in patients with HER2-positive advanced solid tumors," Ann. Oncol., Apr. 2017, 28(4):855-861.
Bauman et al., "Phase I Study of Ficlatuzumab and Cetuximab in Cetuximab-Resistant, Recurrent/Metastatic Head and Neck Cancer.," Cancers, Jun. 11, 2020, 12(6):1537.
Bhati et al., "Efficacy and safety of an anti-CD 20 monoclonal antibody (Reditux™) for the treatment of patients with moderate to severe rheumatoid arthritis following the failure of conventional synthetic disease-modifying anti-rheumatic drugs," Clin. Rheumatol., Aug. 2016, 35(8):1931-1935.
Bilen et al. "Association of Neutrophil-to-Lymphocyte Ratio with Efficacy of First-Line Avelumab plus Axitinib vs. Sunitinib in Patients with Advanced Renal Cell Carcinoma Enrolled in the Phase 3 Javelin Renal 101 Trial," Clin Cancer Res., Feb. 15, 2022, 28(4):738-747.
Bilusic et al., "Phase I trial of HuMax-IL8 (BMS-986253), an anti-IL-8 monoclonal antibody, in patients with metastatic or unresectable solid tumors," J. Immunother. Cancer, Sep. 5, 2019, 7(1):240.
Bobkov et al., "Antibodies targeting chemokine receptors CXCR4 and ACKR3," Mol. Pharmacol., Dec. 2019, 96(6):753-764.
Brunker et al., "RG7386, a novel tetravalent FAP-DR5 antibody, effectively triggers FAP-dependent, avidity-driven DR5 hyperclustering and tumor cell apoptosis," Mol. Cancer Ther., May 2016, 15(5):946-57.
Burge et al., "Pharmacokinetic and pharmacodynamic properties of TRU-015, a CD20-directed small modular immunopharmaceutical protein therapeutic, in patients with rheumatoid arthritis: a Phase I, open-label, dose-escalation clinical study," Clin. Ther., Oct. 2008, 30(10):1806-1816.
Carson et al., "A potential role for interleukin-15 in the regulation of human natural killer cell survival," The Journal of Clinical Investigation, Mar. 1, 1997, 99(5):937-943.
Casulo et al., "A phase I study of PRO131921, a novel anti-CD20 monoclonal antibody in patients with relapsed/refractory CD20+ indolent NHL: correlation between clinical responses and AUC pharmacokinetics," Clin. Immunol., Sep. 2014, 154(1):37-46.
Catenacci et al., "Phase I escalation and expansion study of bemarituzumab (FPA144) in patients with advanced solid tumors and FGFR2b-selected gastroesophageal adenocarcinoma.," J. Clin. Oncol., Jul. 20, 2020, 38(21):2418-2426.

(56) References Cited

OTHER PUBLICATIONS

Cerutti et al., "Physicochemical and biological characterization of RTXM83, a new rituximab biosimilar," BioDrugs, Jun. 2019, 33(3):307-319.
Chamie et al., "Adjuvant weekly girentuximab following nephrectomy for high-risk renal cell carcinoma: the Ariser randomized clinical trial," JAMA Oncol., Jul. 2017, 3(7):913-920.
Chen et al., "IGF-1R as an anti-cancer target—trials and tribulations," Chinese Journal of Cancer, May 2013, 32(5):242-252.
Cheney et al., "Ocaratuzumab, an Fc-engineered antibody demonstrates enhanced antibody-dependent cell-mediated cytotoxicity in chronic lymphocytic leukemia," MAbs, May-Jun. 2014, 6(3):749-55.
Cheng et al., "Safety and efficacy of tigatuzumab plus sorafenib as first-line therapy in subjects with advanced hepatocellular carcinoma: a phase 2 randomized study," J. Hepatol., Oct. 2015, 63(4):896-904.
Cho et al., "Antitumor activity of MEDI3726 (ADCT-401), a pyrrolobenzodiazepine antibody-drug conjugate targeting PSMA, in preclinical models of prostate cancer," Mol Cancer Ther., Oct. 2018, 17(10):2176-2186.
Choi et al., "Phase I Trial: Cirmtuzumab Inhibits ROR1 Signaling and Stemness Signatures in Patients with Chronic Lymphocytic Leukemia," Cell Stem Cell, Jun. 2018, 22(6):951-959.
ClinicalTrials.gov [online], "64Cu-TLX592 Phase I Safety, PK, Biodistribution and Dosimetry Study (CUPID Study) (CUPID)," NCT04726033, Nov. 28, 2022, retrieved on Feb. 20, 2024, retrieved from URL: <https://clinicaltrials.gov/study/NCT04726033>, 26 pages.
ClinicalTrials.gov [online], "A Dose Escalation Study of Glofitamab (RO7082859) as a Single Agent and in Combination With Obinutuzumab After a Fixed, Single Pre-Treatment Dose of Obinutuzumab in Participants With Relapsed/Refractory B-Cell Non-Hodgkin's Lymphoma," NCT03075696, Jan. 30, 2024, retrieved on Feb. 16, 2024, retrieved from URL: <https://clinicaltrials.gov/study/NCT03075696>, 41 pages.
ClinicalTrials.gov [online], "A Double-blind, Randomized Controlled Study in CD20-positive Diffuse B Cell Non-Hodgkin's Lymphoma Subjects," NCT01205737, Oct. 22, 2013, retrieved on Feb. 16, 2024, retrieved from URL: <https://clinicaltrials.gov/study/NCT01205737>, 22 pages.
ClinicalTrials.gov [online], "A First-in-human Study of the Safety, Pharmacokinetics, Pharmacodynamics and Anti-tumor Activity of SAR439459 Monotherapy and Combination of SAR439459 and Cemiplimab in Patients With Advanced Solid Tumors," NCT03192345, May 12, 2022, retrieved on Feb. 16, 2024, retrieved from URL: <https://clinicaltrials.gov/study/NCT03192345>, 37 pages.
ClinicalTrials.gov [online], "A Phase 1 Study of the Clinical and Immunologic Effects of ALT-803 in Patients With Advanced Solid Tumors," NCT01946789, Apr. 17, 2019, retrieved on Feb. 16, 2024, retrieved from URL: <https://clinicaltrials.gov/study/NCT01946789>, 23 pages.
ClinicalTrials.gov [online], "A Phase I Dose-Escalation Study of IMGN388 in Patients With Solid Tumors," NCT00721669, Sep. 13, 2013, retrieved on Feb. 8, 2024, retrieved from URL: <https://clinicaltrials.gov/study/NCT00721669>, 21 pages.
ClinicalTrials.gov [online], "A Phase I Pilot Study Comparing 123I MIP 1072 Versus 111In Capromab Pendetide in Subjects With Metastatic Prostate Cancer," NCT00992745, Oct. 12, 2011, retrieved on Feb. 8, 2024, retrieved from URL: <https://clinicaltrials.gov/study/NCT00992745>, 23 pages.
ClinicalTrials.gov [online], "A Phase I Study of Intravenous CO-H01 in Patients With Refractory or Relapsed Follicular Lymphoma," NCT03221348, Jan. 24, 2018, retrieved on Feb. 16, 2024, retrieved from URL: <https://clinicaltrials.gov/study/NCT03221348>, 22 pages.
ClinicalTrials.gov [online], "A Phase I Study of Lintuzumab-Ac225 in Patients With Refractory Multiple Myeloma," NCT02998047, Mar. 8, 2022, retrieved on Feb. 16, 2024, retrieved from URL: <https://clinicaltrials.gov/study/NCT02998047>, 25 pages.
ClinicalTrials.gov [online], "A Randomized, Double-blind, Multi-center, Multi-national Trial to Evaluate the Efficacy, Safety, and Immunogenicity of SAIT101 Versus Rituximab as a First-line Immunotherapy Treatment in Patients With Low Tumor Burden Follicular Lymphoma (RAMO-2)," NCT02809053, Oct. 8, 2020, retrieved on Feb. 16, 2024, retrieved from URL: <https://clinicaltrials.gov/study/NCT02809053>, 68 pages.
ClinicalTrials.gov [online], "A Safety and Tolerability Study of NC318 in Subjects With Advanced or Metastatic Solid Tumors," NCT03665285, Dec. 26, 2023, retrieved on Feb. 16, 2024, retrieved from URL: <https://clinicaltrials.gov/study/NCT03665285>, 29 pages.
ClinicalTrials.gov [online], "A Study Comparing GB241 And Rituximab in Patients With B-cell Non-Hodgkin's Lymphoma," NCT03003039, Mar. 23, 2021, retrieved on Feb. 16, 2024, retrieved from URL: <https://clinicaltrials.gov/study/NCT03003039>, 20 pages.
ClinicalTrials.gov [online], "A Study Evaluating the Safety and Pharmacokinetics of DMUC4064A in Participants With Platinum-Resistant Ovarian Cancer or Unresectable Pancreatic Cancer," NCT02146313, Jun. 21, 2018, retrieved on Feb. 16, 2024, retrieved from URL: <https://clinicaltrials.gov/study/NCT02146313>, 26 pages.
ClinicalTrials.gov [online], "A Study in Participants With Diabetic Kidney Disease," NCT01113801, Sep. 17, 2019, retrieved on Feb. 8, 2024, retrieved from URL: <https://classic.clinicaltrials.gov/ct2/show/NCT01113801>, 54 pages.
ClinicalTrials.gov [online], "A Study of AK119 (Anti-CD73 Antibody), a Treatment for COVID-19, in Health Subjects," NCT04516564, Oct. 18, 2021, retrieved on Feb. 20, 2024, retrieved from URL: <https://clinicaltrials.gov/study/NCT04516564>, 21 pages.
ClinicalTrials.gov [online], "A Study of Anti-VEGFR2 AK109 in Subjects With Advanced Solid Tumors," NCT04547205, Feb. 23, 2023, retrieved on Feb. 20, 2024, retrieved from URL: <https://clinicaltrials.gov/study/NCT04547205>, 21 pages.
ClinicalTrials.gov [online], "A Study of Axatilimab at 3 Different Doses in Participants With Chronic Graft Versus Host Disease (cGVHD) (AGAVE-201)," NCT04710576, Aug. 21, 2023, retrieved on Feb. 20, 2024, retrieved from URL: <https://clinicaltrials.gov/study/NCT04710576>, 28 pages.
ClinicalTrials.gov [online], "A Study of BI-1206 in Combination With Pembrolizumab in Subjects With Advanced Solid Tumors (KEYNOTE-A04)," NCT04219254, Nov. 24, 2023, retrieved on Feb. 20, 2024, retrieved from URL: <https://clinicaltrials.gov/study/NCT04219254>, 29 pages.
ClinicalTrials.gov [online], "A Study of HLX06, a Humanized Monoclonal Antibody Targeting Human Vascular Endothelial Growth Factor Receptor-2 in Patients With Advanced Solid Tumors," NCT03494231, Jul. 30, 2019, retrieved on Feb. 16, 2024, retrieved from URL: <https://clinicaltrials.gov/study/NCT03494231>, 23 pages.
ClinicalTrials.gov [online], "A Study of IGN002 for Refractory NHL," NCT02847949, Mar. 11, 2022, retrieved on Feb. 16, 2024, retrieved from URL: <https://clinicaltrials.gov/study/NCT02847949>, 21 pages.
ClinicalTrials.gov [online], "A Study of Imvotamab Monotherapy and in Combination in Subjects With Relapsed/Refractory Non-Hodgkin Lymphoma," NCT04082936, Nov. 15, 2023, retrieved on Feb. 20, 2024, retrieved from URL: <https://clinicaltrials.gov/study/NCT04082936>, 23 pages.
ClinicalTrials.gov [online], "A Study of JNJ-63898081 in Participants With Advanced Stage Solid Tumors," NCT03926013, Nov. 7, 2022, retrieved on Feb. 20, 2024, retrieved from URL: <https://clinicaltrials.gov/study/NCT03926013>, 23 pages.
ClinicalTrials.gov [online], "A Study of LY3076226 in Participants With Advanced or Metastatic Cancer," NCT02529553, Apr. 17, 2020, retrieved on Feb. 16, 2024, retrieved from URL: <https://clinicaltrials.gov/study/NCT02529553>, 40 pages.
ClinicalTrials.gov [online], "A Study of MIL62 in Treatment of CD20 Positive B-cell Lymphomas," NCT04103905, Jun. 16, 2021, retrieved on Feb. 20, 2024, retrieved from URL: <https://clinicaltrials.gov/study/NCT04103905>, 23 pages.
ClinicalTrials.gov [online], "A Study of MSB0254 Injection in Advanced Solid Tumors," NCT04381325, Apr. 5, 2023, retrieved on Feb. 20, 2024, retrieved from URL: <https://clinicaltrials.gov/study/NCT04381325>, 26 pages.
ClinicalTrials.gov [online], "A Study to Assess Safety and Efficacy of PRL3-Zumab in Patients With Solid Tumors," NCT04452955,

(56) References Cited

OTHER PUBLICATIONS

Mar. 1, 2023, retrieved on Feb. 20, 2024, retrieved from URL: <https://clinicaltrials.gov/study/NCT04452955>, 26 pages.
ClinicalTrials.gov [online], "A Study to Assess the Anti-Tumor Activity and Safety of Odronextamab in Patients With B-cell Non-Hodgkin Lymphoma That Have Been Previously Treated (ELM-2)," NCT03888105, Apr. 20, 2023, retrieved on Feb. 16, 2024, retrieved from URL: <https://clinicaltrials.gov/study/NCT03888105>, 36 pages.
ClinicalTrials.gov [online], "A Study to Assess the Safety and Efficacy of ASP1650, a Monoclonal Antibody Targeting Claudin 6 (CLDN6), in Male Subjects With Incurable Platinum Refractory Germ Cell Tumors," NCT03760081, Dec. 2, 2021, retrieved on Feb. 16, 2024, retrieved from URL: <https://clinicaltrials.gov/study/NCT03760081>, 65 pages.
ClinicalTrials.gov [online], "A Study to Compare the Efficacy and Safety of JHL1101 Versus Rituximab in Patients With Previously Untreated Diffuse Large B-Cell Lymphoma (DLBCL)," NCT03670901, Jan. 9, 2020, retrieved on Feb. 16, 2024, retrieved from URL: <https://clinicaltrials.gov/study/NCT03670901>, 21 pages.
ClinicalTrials.gov [online], "A Study to Evaluate Escalating Doses of ASP1235 (AGS62P1) Given as Monotherapy in Subjects With Acute Myeloid Leukemia (AML)," NCT02864290, Oct. 29, 2021, retrieved on Feb. 16, 2024, retrieved from URL: <https://clinicaltrials.gov/study/NCT02864290>, 46 pages.
ClinicalTrials.gov [online], "A Study to Evaluate Safety, Tolerability and Preliminanry Efficacy of FP-1305 in Cancer Patients (MATINS)," NCT03733990, Nov. 27, 2023, retrieved on Feb. 16, 2024, retrieved from URL: <https://clinicaltrials.gov/study/NCT03733990>, 23 pages.
ClinicalTrials.gov [online], "An A/B Dose Escalation Study of AbGn-7 Alone and With FOLFOX7 Treatment in Patients With Advanced Solid Tumors," NCT01466569, Jun. 23, 2015, retrieved on Feb. 16, 2024, retrieved from URL: <https://clinicaltrials.gov/study/NCT01466569>, 24 pages.
ClinicalTrials.gov [online], "An Active Treatment Study of SRK-015 in Patients With Type 2 or Type 3 Spinal Muscular Atrophy," NCT03921528, Apr. 12, 2023, retrieved on Feb. 20, 2024, retrieved from URL: <https://clinicaltrials.gov/study/NCT03921528>, 56 pages.
ClinicalTrials.gov [online], "An Open-Label Study of Intra-articular AMB-05X Injections in Subjects With Tenosynobial Giant Cell Tumor of the Knee," NCT04731675, Oct. 6, 2022, retrieved on Feb. 20, 2024, retrieved from URL: <https://clinicaltrials.gov/study/NCT04731675>, 24 pages.
ClinicalTrials.gov [online], "ARX517 as Monotherapy and in Combination Regimens in Subjects With Metastatic Castration-resistant Prostate Cancer (ARX517)," NCT04662580, Nov. 22, 2023, retrieved on Feb. 20, 2024, retrieved from URL: <https://clinicaltrials.gov/study/NCT04662580>, 27 pages.
ClinicalTrials.gov [online], "Assessment Of The Safety And Efficacy Of BG9924 In Rheumatoid Arthritis (RA) Participants (RESPOND)," NCT00664716, Jan. 1, 2016, retrieved on Feb. 8, 2024, retrieved from URL: <https://clinicaltrials.gov/study/NCT00664716>, 19 pages.
ClinicalTrials.gov [online], "B001 in Patients With CD20 Positive B-cell Non Hodgkin's Lymphoma," NCT03332121, Nov. 15, 2021, retrieved on Feb. 16, 2024, retrieved from URL: <https://clinicaltrials.gov/study/NCT03332121>, 21 pages.
ClinicalTrials.gov [online], "Comparative Pharmacokinetic Trial of RGB-03 and MabThera," NCT02371096, Feb. 25, 2015, retrieved on Feb. 16, 2024, retrieved from URL: <https://clinicaltrials.gov/study/NCT02371096>, 15 pages.
ClinicalTrials.gov [online], "Comparative Study of the Efficacy and Safety of BCD-132 With Teriflunomide and Placebo in Multiple Sclerosis," NCT04056897, Sep. 8, 2021, retrieved on Feb. 20, 2024, retrieved from URL: <https://clinicaltrials.gov/study/NCT04056897>, 31 pages.
ClinicalTrials.gov [online], "First in Human Trial of TAS266 in Patients With Advanced Solid Tumors," NCT01529307, Dec. 21, 2020, retrieved on Feb. 16, 2024, retrieved from URL: <https://clinicaltrials.gov/study/NCT01529307>, 20 pages.
ClinicalTrials.gov [online], "First-in-man Dose Escalation Study of BAY1179470 in Patients With Advanced, Refractory Solid Tumors," NCT01881217, Sep. 14, 2017, retrieved on Feb. 16, 2024, retrieved from URL: <https://clinicaltrials.gov/study/NCT01881217>, 24 pages.
ClinicalTrials.gov [online], "Intra-operative Optical Imaging With MDX1201-A488 in Patients With Prostate Cancer," NCT02048150, Mar. 21, 2023, retrieved on Feb. 16, 2024, retrieved from URL: <https://clinicaltrials.gov/study/NCT02048150>, 23 pages.
ClinicalTrials.gov [online], "MabionCD20 Compared to Mab Thera in Lymphoma Patients (MADILYM)," NCT02617485, Oct. 25, 2023, retrieved on Feb. 16, 2024, retrieved from URL: <https://clinicaltrials.gov/study/NCT02617485>, 51 pages.
ClinicalTrials.gov [online], "Nivolumab Combined With BMS-986253 in HCC Patients," NCT04050462, Aug. 30, 2023, retrieved on Feb. 20, 2024, retrieved from URL: <https://clinicaltrials.gov/study/NCT04050462>, 22 pages.
ClinicalTrials.gov [online], "Pharmacokinetics and Pharmacodynamics of BI 695500 vs. Rituximab as First Line-treatment in Patients With Low Tumor Burden Follicular Lymphoma," NCT01950273, Sep. 5, 2018, retrieved on Feb. 16, 2024, retrieved from URL: <https://clinicaltrials.gov/study/NCT01950273>, 45 pages.
ClinicalTrials.gov [online], "Pharmacokinetics, Efficacy and Safety of the 304 Injection," NCT03980379, Jun. 10, 2019, retrieved on Feb. 20, 2024, retrieved from URL: <https://clinicaltrials.gov/study/NCT03980379>, 22 pages.
ClinicalTrials.gov [online], "Phase 1 Study of INBRX-109 in Subjects With Locally Advanced or Metastatic Solid Tumors Including Sarcomas," NCT03715933, Feb. 15, 2024, retrieved on Feb. 16, 2024, retrieved from URL: <https://clinicaltrials.gov/study/NCT03715933>, 29 pages.
ClinicalTrials.gov [online], "Phase 1/2 Study of OBI-999 in Patients With Advanced Solid Tumors," NCT04084366, Jan. 5, 2024, retrieved on Feb. 20, 2024, retrieved from URL: <https://clinicaltrials.gov/study/NCT04084366>, 26 pages.
ClinicalTrials.gov [online], "Phase 2 Study to Evaluate Safety & Efficacy of VPI 2690B in Diabetic Nephropathy Patients," NCT02251067, Mar. 28, 2017, retrieved on Feb. 16, 2024, retrieved from URL: <https://clinicaltrials.gov/study/NCT02251067>, 18 pages.
ClinicalTrials.gov [online], "Pilot Study With CY, Pembrolizumab, GVAX, and IMC-CS4 (LY3022855) in Patients With Borderline Resectable Adenocarcinoma of the Pancreas," NCT03153410, Jan. 29, 2024, retrieved on Feb. 16, 2024, retrieved from URL: <https://clinicaltrials.gov/study/NCT03153410>, 24 pages.
ClinicalTrials.gov [online], "Preoperative Immunotherapy in Patients With Squamous Cell Carcinoma of the Head and Neck," NCT03708224, Jan. 17, 2023, retrieved on Feb. 16, 2024, retrieved from URL: <https://clinicaltrials.gov/study/NCT03708224>, 32 pages.
ClinicalTrials.gov [online], "RHCACD20MA (HS006) With CHOP (Hi-CHOP) in Patients With Previously Untreated Diffuse Large B-cell Lymphoma (Hi-CHOP)," NCT03485118, Apr. 2, 2018, retrieved on Feb. 16, 2024, retrieved from URL: <https://clinicaltrials.gov/study/NCT03485118>, 23 pages.
ClinicalTrials.gov [online], "Safety and Pharmacokinetic Study of IMM0306 in Patients With Refractory or Relapsed CD20-positive B-cell Non-Hodgkin's Lymphoma (B-NHL)," NCT04746131, Sep. 26, 2022, retrieved on Feb. 20, 2024, retrieved from URL: <https://clinicaltrials.gov/study/NCT04746131>, 18 pages.
ClinicalTrials.gov [online], "Safety, Pharmacokinetics and Pharmacodynamics of Recombinant Chimeric Anti-CD20 Monoclonal Antibody in Patients With B-cell Non-Hodgkin's Lymphoma," NCT02206308, Aug. 1, 2014, retrieved on Feb. 16, 2024, retrieved from URL: <https://clinicaltrials.gov/study/NCT02206308>, 19 pages.
ClinicalTrials.gov [online], "SRK-181 Alone or in Combination With Anti-PD(L)1 Antibody Therapy in Patients With Locally Advanced or Metastatic Solid Tumors (DRAGON)," NCT04291079, Jan. 11, 2024, retrieved on Feb. 20, 2024, retrieved from URL: <https://clinicaltrials.gov/study/NCT04291079>, 26 pages.
ClinicalTrials.gov [online], "Study Evaluating the Safety, Pharmacokinetics, and Pharmacodynamics of MYO-029,"

(56) References Cited

OTHER PUBLICATIONS

NCT00563810, Nov. 26, 2007, retrieved on Feb. 8, 2024, retrieved from URL: <https://clinicaltrials.gov/study/NCT00563810>, 16 pages.

ClinicalTrials.gov [online], "Study of AVE1642 Anti-IGF1R Monoclonal Antibody in Patients With Advanced Multiple Myeloma," NCT01233895, Nov. 3, 2010, retrieved on Feb. 16, 2024, retrieved from URL: <https://clinicaltrials.gov/study/NCT01233895>, 21 pages.

ClinicalTrials.gov [online], "Study of Efficacy and Safety of NIS793 (With and Without Spartalizumab) in Combination With SOC Chemotherapy in First-line Metastatic Pancreatic Ductal Adenocarcinoma (mPDAC) (daNIS-1)," NCT04390763, Jan. 25, 2024, retrieved on Feb. 20, 2024, retrieved from URL: <https://clinicaltrials.gov/study/NCT04390763>, 29 pages.

ClinicalTrials.gov [online], "Study of Idelalisib in Combination With BI 836826 in Participants With Chronic Lymphocytic Leukemia," NCT02538614, Nov. 25, 2020, retrieved on Feb. 16, 2024, retrieved from URL: <https://clinicaltrials.gov/study/NCT02538614>, 47 pages.

ClinicalTrials.gov [online], "Study of JTX 8064, as Monotherapy and in Combination With a PD-1 Inhibitor, in Adult Subjects With Advanced Refractory Solid Tumors," NCT04669899, Feb. 12, 2024, retrieved on Feb. 20, 2024, retrieved from URL: <https://clinicaltrials.gov/study/NCT04669899>, 32 pages.

ClinicalTrials.gov [online], "Study of MK-8808 for Participants With Follicular Lymphoma (MK-8808-001)," NCT01370694, Mar. 15, 2019, retrieved on Feb. 16, 2024, retrieved from URL: <https://clinicaltrials.gov/study/NCT01370694>, 39 pages.

ClinicalTrials.gov [online], "Study of Recombinant Human-Mouse Chimeric Anti-CD20 Monoclonal Antibody to Treat Non-hodgkin's Lymphoma," NCT01459887, Oct. 26, 2011, retrieved on Feb. 16, 2024, retrieved from URL: <https://clinicaltrials.gov/study/NCT01459887>, 23 pages.

ClinicalTrials.gov [online], "Study of STRO-001, an Anti-CD74 Antibody Drug Conjugate, in Patients With Advanced B-Cell Malignancies," NCT03424603, Dec. 14, 2022, retrieved on Feb. 16, 2024, retrieved from URL: <https://clinicaltrials.gov/study/NCT03424603>, 27 pages.

ClinicalTrials.gov [online], "Study of TQB2303 in Patients With CD20-Positive Diffuse Large B-cell Lymphoma (DLBCL)," NCT03777085, May 30, 2019, retrieved on Feb. 16, 2024, retrieved from URL: <https://clinicaltrials.gov/study/NCT03777085>, 21 pages.

ClinicalTrials.gov [online], "Study to Assess the Safety and Tolerability of Multiple Ascending Doses of REGN1033 (SAR391786)," NCT01720576, Sep. 12, 2013, retrieved on Feb. 16, 2024, retrieved from URL: <https://clinicaltrials.gov/study/NCT01720576>, 20 pages.

ClinicalTrials.gov [online], "Study to Evaluate Safety and Tolerability of XmAb13676 (Plamotamab) in Patients With CD20-expressing Hematologic Malignancies," NCT02924402, Dec. 20, 2023, retrieved on Feb. 16, 2024, retrieved from URL: <https://clinicaltrials.gov/study/NCT02924402>, 25 pages.

ClinicalTrials.gov [online], "This Study is to Evaluate Safe and Effective Treatment Dose of OBI-888 in Patients With Locally Advanced or Metastatic Solid Tumors," NCT03573544, Jul. 8, 2022, retrieved on Feb. 16, 2024, retrieved from URL: <https://clinicaltrials.gov/study/NCT03573544>, 26 pages.

ClinicalTrials.gov [online], "TREatment of degenerative and Neoplastic Diseases With Rituximab (TREND)," NCT01277172, Jan. 14, 2011, retrieved on Feb. 16, 2024, retrieved from URL: <https://clinicaltrials.gov/study/NCT01277172>, 22 pages.

ClinicalTrials.gov [online], "Trial of Active Immunotherapy With OBI-833 (Globo H-CRM197) in Advanced/Metastatic Gastric, Lung, Colorectal or Breast Cancer Subjects," NCT02310464, Oct. 3, 2022,, retrieved on Feb. 16, 2024, retrieved from URL: <https://clinicaltrials.gov/study/NCT02310464>, 42 pages.

ClinicalTrials. gov [online], "A Study of Paclitaxel/Carboplatin With or Without CDP791 in Patients With Lung Cancer," NCT00152477, Apr. 12, 2022, retrieved on Feb. 8, 2024, retrieved from URL: <https://classic.clinicaltrials.gov/ct2/show/NCT00152477>, 35 pages.

Coiffier, "Pharmacokinetics, efficacy and safety of the rituximab biosimilar CT-P10," Expert Rev. Clin. Pharmacol., Sep. 2017, 10(9):923-933.

Cooper et al., "Human natural killer cells: a unique innate immunoregulatory role for the $CD56^{bright}$ subset," Immunobiology, May 15, 2001, 97 (10): 3146-3151.

D'Angelo et al., "A phase 2 study of ontuxizumab, a monoclonal antibody targeting endosialin, in metastatic melanoma," Invest. New Drugs, Feb. 2018, 36(1):103-113.

Dalili et al., "A Review of Sorting, Separation and Isolation of Cells and Microbeads for Biomedical Applications: Microfluidic Approaches," Analyst, 2019, 144:87-113.

Damjanov et al., "Safety and efficacy of SBI-087, a subcutaneous agent for B cell depletion, in patients with active rheumatoid arthritis: results from a phase II randomized, double-blind, placebo-controlled study," J. Rheumatol., Dec. 2016, 43(12):2094-2100.

De Bono et al., "Phase I trial of a murine antibody to MUC1 in patients with metastatic cancer: evidence for the activation of humoral and cellular antitumor immunity," Ann Oncol., Dec. 2004, 15(12):1825-33.

De Weers et al., "Daratumumab, a novel therapeutic human CD38 monoclonal antibody, induces killing of multiple myeloma and other hematological tumors," J. Immunol., Feb. 2011, 186(3):1840-1848.

Dotti et al., "Design and Development of Therapies using Chimeric Antigen Receptor-Expressing T cells," Immunol Rev., Jan. 2014, 257(1)1-35.

Du et al., "Next-generation anti-CD20 monoclonal antibodies in autoimmune disease treatment," Autoimmunity Highlights, Dec. 2017, 8(1):1-2.

Forero et al., "First-in-human study of the antibody DR5 agonist DS-8273a in patients with advanced solid tumors," Invest New Drugs, Jan. 3, 2017, 35(3):298-306.

Fox et al., "A phase 2 multicenter study of ublituximab, a novel glycoengineered anti-CD20 monoclonal antibody, in patients with relapsing forms of multiple sclerosis," Mult. Scler., Mar. 2021, 27(3):420-429.

Fulciniti et al., "Anti-DKK1 mAb (BHQ880) as a potential therapeutic agent for multiple myeloma," Blood, Jul. 9, 2009, 114(2):371-9.

Gagez et al., "Obinutuzumab: a new class of anti-CD20 monoclonal antibody," Curr. Opin. Oncol., Sep. 2014, 26(5):484-491.

Garcia et al., "Bevacizumab (Avastin®) in cancer treatment: A review of 15 years of clinical experience and future outlook," Cancer Treat Rev., Jun. 2020, 86:102017.

Genovese et al., "Ocrelizumab, a humanized anti-CD20 monoclonal antibody, in the treatment of patients with rheumatoid arthritis: a phase I/II randomized, blinded, placebo-controlled, dose-ranging study," Arthritis Rheum., Sep. 2008, 58(9):2652-61.

Geoghegan et al., "Inhibition of CD73 AMP hydrolysis by a therapeutic antibody with a dual, non-competitive mechanism of action," MAbs, Apr. 2, 2016, 8(3):454-67.

Gibson et al., "Randomized Phase III Trial Results of Panitumumab, a Fully Human Anti-Epidermal Growth Factor Receptor Monoclonal Antibody, in Metastatic Colorectal Cancer," Clin Colorectal Cancer, May 1, 2006, 6(1):29-31.

Gilbert et al., "Effect of CC chemokine receptor 2 CCR2 blockade on serum C-reactive protein in individuals at atherosclerotic risk and with a single nucleotide polymorphism of the monocyte chemoattractant protein-1 promoter region," Am. J. Cardiol., Mar. 15, 2011, 107(6):906-11.

Golan et al., "LY2495655, an antimyostatin antibody, in pancreatic cancer: a randomized, phase 2 trial," J. Cachexia Sarcopenia Muscle, Oct. 2018, 9(5):871-879.

Gold et al., "Mapping PAM4 (clivatuzumab), a monoclonal antibody in clinical trials for early detection and therapy of pancreatic ductal adenocarcinoma, to MUC5AC mucin," Molecular Cancer, Dec. 2013, 12(143):1-8.

Goldenberg et al., "Veltuzumab (humanized anti-CD20 monoclonal antibody): characterization, current clinical results, and future prospects," Leuk. Lymphoma, May 2010, 51(5):747-755.

(56) References Cited

OTHER PUBLICATIONS

Goldenberg, "Trastuzumab, a recombinant DNA-derived humanized monoclonal antibody, a novel agent for the treatment of metastatic breast cancer," Clin. Ther., Feb. 1999, 21(2):309-18.

Gross et al., "Five-Year Outcomes of Panretinal Photocoagulation vs Intravitreous Ranibizumab for Proliferative Diabetic Retinopathy: A Randomized Clinical Trial," JAMA Ophthalmol., Oct. 2018, 136(10):1138-1148.

Gupta et al., "Targeting CA 19-9 with a humanized monoclonal antibody at the time of surgery may decrease recurrence rates for patients undergoing resections for pancreatic cancer, cholangiocarcinoma and metastatic colorectal cancer," J. Gastrointest. Oncol., Apr. 2020, 11(2):231-235.

Hammer et al., "Preclinical Efficacy of a PSMA-Targeted Thorium-227 Conjugate (PSMA-TTC), a Targeted Alpha Therapy for Prostate Cancer," Clin. Cancer Res., Apr. 15, 2020, 26(8):1985-1996.

Hashimoto et al., "A novel HER3-targeting antibody-drug conjugate, U3-1402, exhibits potent therapeutic efficacy through the delivery of cytotoxic payload by efficient internalization," Clin. Cancer Res., Dec. 2019, 25(23):7151-7161.

Hassan et al., "First-in-human, multicenter, phase I dose-escalation and expansion study of anti-mesothelin antibody-drug conjugate anetumab ravtansine in advanced or metastatic solid tumors," J. Clin. Oncol., Jun. 6, 2020, 38(16):1824-1835.

Hassan et al., "Mesothelin immunotherapy for cancer: ready for prime time?," J. Clin. Oncol., Dec. 12, 2016, 34(34):4171-4179.

Hensel et al., "Early development of PAT-SM6 for the treatment of melanoma," Melanoma Res., Aug. 2013, 23(4):264-75.

Hernandez-Hoyos et al., "MOR209/ES414, a novel bispecific antibody targeting PSMA for the treatment of metastatic castration-resistant prostate cancer," Mol. Cancer Ther., Sep. 2016, 15(9):2155-2165.

Hersey et al., "A randomized phase 2 study of etaracizumab, a monoclonal antibody against integrin alpha(v)beta(3), + or − dacarbazine in patients with stage IV metastatic melanoma," Cancer, Mar. 15, 2010, 116(6):1526-1534.

Heublin et al., "Potential interplay of the gatipotuzumab epitope TA-MUC1 and estrogen receptors in ovarian cancer," Int. J. Mol. Sci., Jan. 12, 2019, 20(2):295.

Hosseini et al., "Mitigating the risk of cytokine release syndrome in a Phase I trial of CD20/CD3 bispecific antibody mosunetuzumab in NHL: impact of translational system modeling," NPJ Syst. Biol. Appl., Aug. 28, 2020,6(1):28.

Hoy, "Dinutuximab: A Review in High-Risk Neuroblastoma," Target Oncol., Apr. 2016, 11(2):247-53.

Hoy, "Tafasitamab: first approval," Drugs, Nov. 2020, 80(16):1731-1737.

Hsu et al., "The Killer Cell Immunoglobulin-Like Receptor (KIR) Genomic Region: Gene-Order, Haplotypes and Allelic Polymorphism," Immunological Review, Dec. 2002, 190:40-52.

Huang et al., "The CD20-specific engineered toxin antibody MT-3724 exhibits lethal effects against mantle cell lymphoma," Blood Cancer J., Mar. 20, 2018, 8(3):33.

Hudecek et al., "Going Non-Viral: the Sleeping Beauty Transposon System Breaks on Through to the Clinical Side," Critical Reviews in Biochemistry and Molecular Biology, Jul. 4, 2017, 52(4):355-380.

Hughes et al., "Have Clinical Trials Properly Assessed c-Met Inhibitors?," Trends Cancer, Feb. 2018, 4(2):94-97.

Hummel et al., "Pasotuxizumab, a BiTE® immune therapy for castration-resistant prostate cancer: Phase I, dose-escalation study findings," Immunotherapy, Feb. 2021, 13(2):125-141.

Ishiguro et al., "An anti-glypican 3/CD3 bispecific T cell-redirecting antibody for treatment of solid tumors," Sci. Transl. Med., Oct. 4, 2017, 9(410):eaal4291.

Jiang et al., "Abituzumab targeting of αV-class integrins inhibits prostate cancer progression," Mol. Cancer Res., Jul. 2017, 15(7):875-883.

Jiang et al., "Pharmacokinetics and safety of IBI301 versus rituximab in patients with CD20+ B-cell lymphoma: a multicenter, randomized, double-blind, parallel-controlled study," Sci. Rep., Jul. 15, 2020, 10(1):11676.

Jonker et al., "Cetuximab for the treatment of colorectal cancer," N. Engl. J. Med., Nov. 15, 2007,357(20):2040-2048.

Kalaycio et al., "Subcutaneous injections of low doses of humanized anti-CD20 veltuzumab: a phase I study in chronic lymphocytic leukemia," Leuk. Lymphoma, 2016, 57(4):803-11.

Kang et al., "Drozitumab, a human antibody to death receptor 5, has potent antitumor activity against rhabdomyosarcoma with the expression of caspase-8 predictive of response," Clin. Cancer Res., May 15, 2011, 17(10):3181-92.

Kappos et al., "Ocrelizumab in relapsing-remitting multiple sclerosis: a phase 2, randomised, placebo-controlled, multicentre trial," Lancet., Nov. 19, 2011, 378(9805):1779-87.

Khan et al., "Ramucirumab for the treatment of gastric or gastroesophageal junction cancer," Expert Opin. Biol. Ther., Nov. 2019, 19(11):1135-1141.

Kim et al., "First-in-Human Phase I Study of Aprutumab Ixadotin, a Fibroblast Growth Factor Receptor 2 Antibody-Drug Conjugate (BAY 1187982) in Patients with Advanced Cancer," Target Oncol., Oct. 2019, 14(5):591-601.

Kim et al., "Phase II study of ensituximab, a novel chimeric monoclonal antibody, in adults with unresectable, metastatic colorectal cancer," Clin. Cancer Res., Jul. 15, 2020, 26(14):3557-3564.

Koene et al., "FcγRIIIa-158V/F Polymorphism Influences the Binding of IgG by Natural Killer Cell FcγRIIIa, Independently of the FcγRIIIa-48L/R/H Phenotype," Blood, Aug. 1997, 90(3):1109-1114.

Kuenen et al., "A phase I pharmacologic study of necitumumab (IMC-11F8), a fully human IgG1 monoclonal antibody directed against EGFR in patients with advanced solid malignancies," Clin. Cancer Res., Mar. 15, 2010, 16(6):1915-23.

Leary et al., "Abstract No. 2521: First-in-human first-in-class phase I trial of murlentamab, an anti-Mullerian-hormone receptor II (AMHRII) monoclonal antibody acting through tumor-associated macrophage (TAM) engagement, as single agent and in combination with carboplatin (C) and paclitaxel (P) in AMHRII-expressing advanced/metastatic gynecological cancer patients (pts)," Presented at ASCO 2019, Chicago, Illinois, May 31-Jun. 4, 2019; Journal of Clinical Oncology, May 20, 2019, 37,(15_suppl.), 2 p.

Lee et al., "Preclinical pharmacokinetics, interspecies scaling, and pharmacokinetics of a Phase I clinical trial of TTAC-0001, a fully human monoclonal antibody against vascular endothelial growth factor 2," Drug Des. Devel. Ther., Mar. 8, 2018, 12:495-504.

Lima et al., "Phase Ib study of drozitumab combined with first-line mFOLFOX6 plus bevacizumab in patients with metastatic colorectal cancer," Cancer Invest., Dec. 2012, 30(10):727-31.

Liu et al., "Identification of PAM4 (clivatuzumab)-reactive epitope on MUC5AC: a promising biomarker and therapeutic target for pancreatic cancer," Oncotarget., Feb. 28, 2015, 6(6):4274-85.

Liu et al., "Phase I study of safety and pharmacokinetics of the anti-MUC16 antibody-drug conjugate DMUC5754A in patients with platinum-resistant ovarian cancer or unresectable pancreatic cancer," Ann. Oncol., Nov. 2016, 27(11):2124-2130.

Liu et al., "Use of CAR-Transduced Natural Killer Cells in CD19-Positive Lymphoid Tumors," N. Engl. J. Med., Feb. 6, 2020, 382(6):545-553.

Lonial et al., "Elotuzumab Therapy for Relapsed or Refractory Multiple Myeloma," N. Engl. J. Med., Aug. 13, 2015, 373(7):621-631.

Lord et al., "Structure-based engineering to restore high affinity binding of an isoform-selective anti-TGFβ1 antibody," MAbs., Apr. 2018, 10(3):444-452.

LoRusso et al., "Icrucumab, a fully human monoclonal antibody against the vascular endothelial growth factor receptor-1, in the treatment of patients with advanced solid malignancies: a Phase 1 study," Invest. New. Drugs, Apr. 2014, 32(2):303-11.

Mahalingham et al., "Phase I study of imalumab (BAX69), a fully human recombinant antioxidized macrophage migration inhibitory factor antibody in advanced solid tumours," Br. J. Clin. Pharmacol., Sep. 2020, 86(9):1836-1848.

(56) References Cited

OTHER PUBLICATIONS

Marchio et al. "Evolving concepts in HER2 evaluation in breast cancer: Heterogeneity, HER2-low carcinomas and beyond," Semin Cancer Biol, Feb. 26, 2020, 72:123-135.
Marcus et al., "Obinutuzumab for the First-Line Treatment of Follicular Lymphoma," N. Engl. J. Med., Oct. 5, 2017, 377(14):1331-1344.
Markham, "Naxitamab: First Approval," Drugs, Feb. 2021, 81(2):291-296.
Martin et al., "Phase I trial of isatuximab monotherapy in the treatment of refractory multiple myeloma," Blood Cancer J., Mar. 29, 2019, 9(4):41, 10 pages.
Martinsson-Niskanen et al., "Monoclonal antibody TB-403: a first-in-human, Phase I, double-blind, dose escalation study directed against placental growth factor in healthy male subjects," Clin. Ther., Sep. 2011, 33(9):1142-9.
Milone et al., "Clinical Use of Lentiviral Vectors," Leukemia, Jul. 2018, 32(7):1529-41.
Musolino et al., "Immunoglobulin G Fragment C Receptor Polymorphisms and Clinical Efficacy of Trastuzumab-Based Therapy in Patients with HER-2/neu-Positive Metastatic Breast Cancer," J. Clin. Oncol., Apr. 10, 2008, 26(11):1789-1796.
Nadafi et al., "Anti-CD19 Monoclonal Antibodies: a New Approach to Lymphoma Therapy," Int. J. Mol. Cell Med., 2015, 4(3):143-151.
Niederwieser et al., "Efficacy and Safety of ABP 798: Results from the JASMINE Trial in Patients with Follicular Lymphoma in Comparison with Rituximab Reference Product," Target Oncol., Oct. 2020, 15(5):599-611.
O'Day et al., "A randomised, phase II study of intetumumab, an anti-αv-integrin mAb, alone and with dacarbazine in stage IV melanoma," Br. J. Cancer, Jul. 26, 2011, 105(3):346-52.
Office Action in Canadian Application No. 3082328, dated Jan. 29, 2024, 6 pages.
Okamoto et al., "TAK-701, a humanized monoclonal antibody to hepatocyte growth factor, reverses gefitinib resistance induced by tumor-derived HGF in non-small cell lung cancer with an EGFR mutation," Mol. Cancer Ther., Oct. 2010, 9(10):2785-92.
Overdijk et al., "Dual Epitope Targeting and Enhanced Hexamerization by DR5 Antibodies as a Novel Approach to Induce Potent Antitumor Activity Through DR5 Agonism," Mol. Cancer Ther., Oct. 2020, 19(10):2126-2138.
Petrylak et al., "PSMA ADC monotherapy in patients with progressive metastatic castration-resistant prostate cancer following abiraterone and/or enzalutamide: Efficacy and safety in open-label single-arm phase 2 study," Prostate, Jan. 2020, 80(1):99-108.
Piloto et al., "IMC-EB10, an anti-FLT3 monoclonal antibody, prolongs survival and reduces nonobese diabetic/severe combined immunodeficient engraftment of some acute lymphoblastic leukemia cell lines and primary leukemic samples," Cancer Res., May 2006, 66(9):4843-51.
Plummer et al., "Phase 1 and pharmacokinetic study of lexatumumab in patients with advanced cancers," Clin. Cancer Res., Oct. 15, 2007, 13(20):6187-94.
Poddubnaya et al., "Proposed rituximab biosimilar BCD-020 versus reference rituximab for treatment of patients with indolent non-Hodgkin lymphomas: An international multicenter randomized trial," Hematol. Oncol., Feb. 2020, 38(1):67-73.
Pognan et al., "Colony-stimulating factor-1 antibody lacnotuzumab in a phase 1 healthy volunteer study and mechanistic investigation of safety outcomes.," J Pharmacol Exp Ther., Jun. 2019, 369(3):428-442.
Ponath et al., "A Novel, Fully Human Anti-fucosyl-GM1 Antibody Demonstrates Potent In Vitro and In Vivo Antitumor Activity in Preclinical Models of Small Cell Lung Cancer," Clin Cancer Res., Oct. 15, 2018, 24(20):5178-5189.
Pyo et al., "Different Patterns of Evolution in the Centromeric and Telomeric Regions of Group A and B Haplotypes of the Human Killer Cell Ig-like Receptor Locus," PLOS One, Dec. 29, 2010, 5(12)e15115:1-14.

Reck et al., "A randomized, double-blind, placebo-controlled phase 2 study of tigatuzumab (CS-1008) in combination with carboplatin/paclitaxel in patients with chemotherapy-naïve metastatic/unresectable non-small cell lung cancer," Lung Cancer, Dec. 2013, 82(3):441-448.
Rice et al., "Fresolimumab treatment decreases biomarkers and improves clinical symptoms in systemic sclerosis patients," J Clin Invest., Jul. 2015, 125(7):2795-2807.
Robak, "Ofatumumab, a human monoclonal antibody for lymphoid malignancies and autoimmune disorders," Curr Opin Mol Ther., Jun. 2008, 10(3):294-309.
Rosevear et al., "Conatumumab, a fully human mAb against death receptor 5 for the treatment of cancer," Curr Opin Investig Drugs, Jun. 2010, 11(6):688-698.
Sabbatini et al., "Abagovomab as maintenance therapy in patients with epithelial ovarian cancer: a phase III trial of the AGO OVAR, COGI, GINECO, and GEICO—the MIMOSA study," J Clin Oncol., Apr. 20, 2013, 31(12):1554-1561.
Salles et al., "Rituximab in B-Cell Hematologic Malignancies: A Review of 20 Years of Clinical Experience," Adv Ther., Oct. 2017, 34(10):2232-2273.
Sasikumar et al., "Peptide and Peptide-Inspired Checkpoint Inhibitors: Protein Fragments to Cancer Immunotherapy," Medicine in Drug Discovery, Dec. 2020, 8(100073):1-10.
Sato et al., "Profile of farletuzumab and its potential in the treatment of solid tumors," Onco Targets Ther., Mar. 7, 2016, 9:1181-1188.
Sawas et al., "A phase 1/2 trial of ublituximab, a novel anti-CD20 monoclonal antibody, in patients with B-cell non-Hodgkin lymphoma or chronic lymphocytic leukaemia previously exposed to rituximab," Br J Haematol., Apr. 2017, 177(2):243-253.
Segal et al., "Phase I Study of Single-Agent Utomilumab (PF-05082566), a 4-1BB/CD137 Agonist, in Patients with Advanced Cancer," Clin Cancer Res., Apr. 15, 2018, 24(8):1816-1823.
Segal et al., "Results from an Integrated Safety Analysis of Urelumab, an Agonist Anti-CD137 Monoclonal Antibody," Clin Cancer Res., Apr. 15, 2017, 23(8):1929-1936.
Sharman et al., "A Randomized, Double-Blind, Efficacy and Safety Study of PF-05280586 (a Rituximab Biosimilar) Compared with Rituximab Reference Product (MabThera®) in Subjects with Previously Untreated CD20-Positive, Low-Tumor-Burden Follicular Lymphoma (LTB-FL)," BioDrugs, Apr. 2020, 34(2):171-181.
Shi et al., "A phase 3 study of rituximab biosimilar HLX01 in patients with diffuse large B-cell lymphoma," J Hematol Oncol., Apr. 16, 2020, 13(1):38, 5 pages.
Simonelli et al., "Phase I study of PF-03446962, a fully human monoclonal antibody against activin receptor-like kinase-1, in patients with hepatocellular carcinoma," Ann Oncol., Sep. 2016, 27(9):1782-1787.
Smith and Waterman, "Identification of common molecular subsequences," J Mol Biol., Mar. 25, 1981, 147(1):195-197.
Smolen et al., "A randomised, double-blind trial to demonstrate bioequivalence of GP2013 and reference rituximab combined with methotrexate in patients with active rheumatoid arthritis," Ann Rheum Dis., Sep. 2017, , 76(9):1598-1602.
Sorensen et al., "Safety and efficacy of ofatumumab in relapsing-remitting multiple sclerosis: a phase 2 study," Neurology, Feb. 18, 2014, 82(7):573-581.
Stasi, "Gemtuzumab ozogamicin: an anti-CD33 immunoconjugate for the treatment of acute myeloid leukaemia," Expert Opin Biol Ther., Apr. 2008, 8(4):527-540.
Strouhalova et al., "Vimentin intermediate filaments as potential target for cancer treatment," Cancers, Jan. 11, 2020, 12(1):184.
Swords et al., "KB004, a first in class monoclonal antibody targeting the receptor tyrosine kinase EphA3, in patients with advanced hematologic malignancies: Results from a phase 1 study.," Leuk Res., Nov. 2016, 50:123-131.
Takebe et al., "Targeting Notch signaling pathway in cancer: clinical development advances and challenges," Pharmacol Ther., Feb. 2014, 141(2):140-149.
Tolcher et al., "A phase 1 study of anti-TGFβ receptor type-II monoclonal antibody LY3022859 in patients with advanced solid tumors," Cancer Chemother Pharmacol., Apr. 2017, 79(4):673-680.

(56) References Cited

OTHER PUBLICATIONS

Tolcher et al., "Cantuzumab mertansine, a maytansinoid immunoconjugate directed to the CanAg antigen: a phase I, pharmacokinetic, and biologic correlative study," J Clin Oncol., Jan. 15, 2003, 21(2):211-222.

UniProtKB Accession No. P40933, "RecName: Full=Interleukin-15; Short=IL-15; Flags: Precursor," Dec. 24, 2019, 6 pages.

UniProtKB Accession No. P41273, "RecName: Full=Tumor necrosis factor ligand superfamily member 9; AltName: Full=4-1BB ligand; Short=4-1BBL," Oct. 16, 2019, 5 pages.

Vaickus, "Immune markers in hematologic malignancies," Crit Rev. in Oncol./Hemotol., Dec. 1991, 11(4):267-297.

Vallabhajosula et al., "Radioimmunotherapy of Metastatic Prostate Cancer with $^{177}$Lu-DOTAhuJ591 Anti Prostate Specific Membrane Antigen Specific Monoclonal Antibody," Curr Radiopharm., 2016, 9(1):44-53.

Van der Horst et al., "Epcoritamab induces potent anti-tumor activity against malignant B-cells from patients with DLBCL, FL and MCL, irrespective of prior CD20 monoclonal antibody treatment," Blood Cancer J., Feb. 18, 2021, 11(38):1-8.

Vose et al., "Multicenter phase II study of iodine-131 tositumomab for chemotherapy-relapsed/refractory low-grade and transformed low-grade B-cell non-Hodgkin's lymphomas," J Clin Oncol., Mar. 2000, 18(6):1316-1323.

Waddell et al., "Potential role of rilotumumab in the treatment of gastric cancer," Immunotherapy, Dec. 2014, 6(12):1243-1253.

Wagner et al., "Randomized phase 2 trial and open-label extension of domagrozumab in Duchenne muscular dystrophy," Neuromuscul Disord., Jun. 2020, 30(6):492-502.

Wall et al., "The anti-DKK1 antibody DKN-01 as an immunomodulatory combination partner for the treatment of cancer," Expert Opin Investig Drugs., Jul. 2, 2020, 29(7):639-644.

Wiseman et al., "Phase I/II $^{90}$Y-Zevalin (yttrium-90 ibritumomab tiuxetan, IDEC-Y2B8) radioimmunotherapy dosimetry results in relapsed or refractory non-Hodgkin's lymphoma," Eur J Nucl Med., 2000, 27(7):766-777.

Witzig et al., "Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma," J Clin Oncol., May 15, 2002, 20(10):2453-2463.

Wolff et al., "Human Epidermal Growth Factor Receptor 2 Testing in Breast Cancer," Arch Pathol Lab Med., Nov. 2018, 142(11):1364-1382.

Wu et al., "piggyBac is a Flexible and Highly Active Transposon as Compared to Sleeping Beauty, Tol2, and Mos1 in Mammalian Cells," PNAS, Oct. 10, 2006, 103(41):15008-15013.

Yoo et al., "Phase I study of bintrafusp alfa, a bifunctional fusion protein targeting TGF-β and PD-L1, in patients with pretreated biliary tract cancer.," J Immunother Cancer, May 2020,8(1):e000564, 9 pages.

Yu et al., "Antibody-drug conjugates in clinical trials for lymphoid malignancies and multiple myeloma," Journal of Hematology & Oncology, Dec. 2019, 12(94):1-7.

Zelenetz, "A clinical and scientific overview of tositumomab and iodine I 131 tositumomab," Semin Oncol., Apr. 2003, 30(2 Suppl 4):22-30.

Zhang et al., "A novel anti-DR5 antibody-drug conjugate possesses a high-potential therapeutic efficacy for leukemia and solid tumors.," Theranostics., Jul. 13, 2019, 9(18):5412-5423.

* cited by examiner

ANTI-HER2 ANTIBODY OR ANTIGEN-BINDING FRAGMENT THEREOF, AND CHIMERIC ANTIGEN RECEPTOR COMPRISING SAME

REFERENCE TO SEQUENCE LISTING SUBMITTED ELECTRONICALLY

The instant application includes a Sequence Listing which has been submitted electronically in ASCII and is hereby incorporated by reference in its entirety. Said ASCII copy, created Sep. 28, 2020 is named 4411_0210001_SL_ST25.txt and is 116,784 bytes in size.

TECHNICAL FIELD

The research was conducted under the support of the Ministry of Trade, Industry and Energy of Korea with the project number 1415118385. The R&D management agency of the project is the Korea Institute for Advancement of Technology, the R&D project title is "Global innovation technology alliance", and the research title is "Development of global antibody drug based on novel epitope screening platform technology". The research was conducted by AbClon Inc. from Nov. 1, 2011 until Oct. 31, 2014.

This application claims the priority of Korean Patent Application No. 10-2017-0151841 filed on Nov. 14, 2017 in the Korean Intellectual Property Office, the disclosure of which is incorporated herein by reference in its entirety.

The present disclosure relates to a novel anti-HER2 antibody or an antigen-binding fragment thereof, a chimeric antigen receptor including the same, and uses thereof.

BACKGROUND ART

The Her2/neu (ErbB2) gene encodes a 185-kDa transmembrane glycoprotein that belongs to the family of epidermal growth factor receptors (EGFRs). The Her2 protein is composed of an extracellular domain consisting of 620 amino acid residues, a transmembrane domain 23 amino acid residues, and an intracellular domain with tyrosine kinase activity, consisting of 490 amino acid residues (Akiyama T, et al., Science, 232 (4758): 1644-1646 (1986)).

Anti-HER2 antibodies with various characteristics have been described: Tagliabue et al., Int. J. Cancer 47: 933-937 (1991); McKenzie et al., Oncogene 4: 543-548 (1989); Maier et al., Cancer Res. 51: 5361-5369 (1991); Bacus et al., Molecular Carcinogenesis 3: 350-362 (1990); Stancovski et al., PNAS USA 88: 8691-8695 (1991); Bacus et al., Cancer Research 52: 2580-2589 (1992); Xu et al., Int. J. Cancer 53: 401-408 (1993); WO94/00136; Kasprzyk et al., Cancer Research 52: 2771-2776 (1992); Hancock et al., Cancer Res. 51: 4575-4580 (1991); Shawver et al., Cancer Res. 54: 1367-1373 (1994); Arteaga et al., Cancer Res. 54: 3758-3765 (1994); Harwerth et al., J. Biol. Chem. 267: 15160-15167 (1992); U.S. Pat. No. 5,783,186; Kao et al., US Patent Application Publication No. 2009/0285837 (2009); Ross et al., The Oncologist 8: 307-325 (2003); and Klapper et al., Oncogene 14: 2099-2109 (1997).

The most commercially successful anti-HER2 antibody is trastuzumab antibody (commercially available as Herceptin™, U.S. Pat. No. 5,821,337) and many researches have been conducted thereon: Sapino, A., et al., Annals of Oncology (2007) 18: 1963-1968; Bussolati, G, et al., British Journal of Cancer (2005) 92, 1261-1267; and Glazyrin A, et al., J Histology & Cytochemistry (2007) 55 (1): 25-33.

Although the trastuzumab antibody has been commercially successful, use of the trastuzumab antibody for therapeutic purposes is limited because there are various cancer cells which have non-reactivity (or resistance) to the antibody or have reduced sensitivity. Accordingly, there have been attempts to resolve the therapeutic problem of the antibody.

For example, U.S. Pat. No. 7,674,460 discloses a method for increasing the HER2 sensitivity of cancer cells using an HER2 antagonist such as the trastuzumab antibody and a PC cell-derived growth factor (PCDGF) antagonist. WO 2011/127297 discloses a method for inhibiting the proliferation of trastuzumab-resistant tumor cells using a combination of a FoxMl inhibitor and the trastuzumab antibody.

US Patent Application Publication No. 2010-0183604 discloses a method for treating trastuzumab-resistant cancer using a cofilin inhibitor, a PAK1 inhibitor, a LIMK inhibitor, an RHO inhibitor, a ROCK1 inhibitor or a ROCK2 inhibitor.

DISCLOSURE

Technical Problem

The inventors of the present disclosure have made efforts to develop a novel antibody which is capable of preventing or treating cancer (particularly, breast cancer and gastric cancer), exhibits better killing ability (or proliferation-inhibiting ability) for cancer cells which have non-reactivity (or resistance) to the trastuzumab antibody or have reduced sensitivity, and is capable of preventing or treating cancer with improved anticancer activity when co-administered with the trastuzumab antibody as compared to single administration of trastuzumab. As a result, they have developed a novel antibody which exhibits better killing ability for HER2-overexpressed cancer cells on which the trastuzumab antibody hardly acts, or exhibits improved anticancer activity when co-administered with the trastuzumab antibody, and have completed the present disclosure.

The present disclosure is directed to providing an antibody (anti-HER2 antibody) against HER2 (human epidermal growth factor receptor 2) or an antigen-binding fragment thereof.

The present disclosure is also directed to providing a fusion protein including the anti-HER2 antibody or an antigen-binding fragment thereof.

The present disclosure is also directed to providing a chimeric antigen receptor (CAR) including the anti-HER2 antibody or an antigen-binding fragment thereof and an effector cell expressing the same.

The present disclosure is also directed to providing a nucleic acid molecule encoding the anti-HER2 antibody or an antigen-binding fragment thereof, or the chimeric antigen receptor.

The present disclosure is also directed to providing a recombinant vector including the nucleic acid molecule.

The present disclosure is also directed to providing a host cell transformed with the recombinant vector.

The present disclosure is also directed to providing a pharmaceutical composition for preventing or treating cancer, which contains the anti-HER2 antibody or an antigen-binding fragment thereof.

The present disclosure is also directed to providing a kit for diagnosing cancer, which includes the anti-HER2 antibody or an antigen-binding fragment thereof.

The present disclosure is also directed to providing a method for preventing or treating cancer by administering a composition containing the anti-HER2 antibody or an antigen-binding fragment thereof to a subject.

The present disclosure is also directed to providing a method for treating a disease related with HER2 overexpression (e.g., cancer) by administering an effector cell expressing the chimeric antigen receptor to a subject.

Technical Solution

The present disclosure provides an antibody binding specifically to HER2 (human epidermal growth factor receptor 2) and modified antibodies thereof that have undergone affinity maturation.

A first aspect of the present disclosure provides an antibody against HER2 (human epidermal growth factor receptor 2) including the followings or an antigen-binding fragment thereof:
- (a) a heavy chain variable region including the following heavy chain CDR (complementarity-determining region) amino acid sequences:
  CDRH1 of SEQ ID NO 1, CDRH2 of SEQ ID NO 2 and CDRH3 of SEQ ID NO 3; and
- (b) a light chain variable region including the following light chain CDR amino acid sequences:
  CDRL1 of SEQ ID NO 4, CDRL2 of SEQ ID NO 5 and CDRL3 of SEQ ID NO 6.

A second aspect of the present disclosure provides an antibody against HER2 (human epidermal growth factor receptor 2) including the followings or an antigen-binding fragment thereof:
- (a) a heavy chain variable region including the following heavy chain CDR (complementarity-determining region) amino acid sequences:
  CDRH1 of SEQ ID NO 7, CDRH2 of SEQ ID NO 8 and CDRH3 of SEQ ID NO 9, 71 or 72; and
- (b) a light chain variable region including the following light chain CDR amino acid sequences:
  CDRL1 of SEQ ID NO 10, CDRL2 of SEQ ID NO 11 and CDRL3 of SEQ ID NO 12, 73 or 74.

A third aspect of the present disclosure provides an antibody against HER2 (human epidermal growth factor receptor 2) including the following or an antigen-binding fragment thereof:
- (a) a heavy chain variable region including the following heavy chain CDR (complementarity-determining region) amino acid sequences:
  CDRH1 of SEQ ID NO 13, CDRH2 of SEQ ID NO 14 and CDRH3 of SEQ ID NO 15; and
- (b) a light chain variable region including the following light chain CDR amino acid sequences:
  CDRL1 of SEQ ID NO 16, CDRL2 of SEQ ID NO 17 and CDRL3 of SEQ ID NO 18.

A fourth aspect of the present disclosure provides an antibody against HER2 (human epidermal growth factor receptor 2) including the following or an antigen-binding fragment thereof:
- (a) a heavy chain variable region including the following heavy chain CDR (complementarity-determining region) amino acid sequences:
  CDRH1 of SEQ ID NO 19, CDRH2 of SEQ ID NO 20 and CDRH3 of SEQ ID NO 21; and
- (b) a light chain variable region including the following light chain CDR amino acid sequences:
  CDRL1 of SEQ ID NO 22, CDRL2 of SEQ ID NO 23 and CDRL3 of SEQ ID NO 24.

A fifth aspect of the present disclosure provides an antibody against HER2 (human epidermal growth factor receptor 2) including the following or an antigen-binding fragment thereof:
- (a) a heavy chain variable region including the following heavy chain CDR (complementarity-determining region) amino acid sequences:
  CDRH1 of SEQ ID NO 25, CDRH2 of SEQ ID NO 26 and CDRH3 of SEQ ID NO 27; and
- (b) a light chain variable region including the following light chain CDR amino acid sequences:
  CDRL1 of SEQ ID NO 28, CDRL2 of SEQ ID NO 29 and CDRL3 of SEQ ID NO 30.

The antibody of the first aspect, the antibody of the second aspect, the antibody of the third aspect, the antibody of the fourth aspect and the antibody of the fifth aspect are referred to, respectively, as 2G10, 39D2, 24D3, 1G3 and 8G11 antibodies. They are mouse antibodies or chimeric antibodies. Among them, the humanized antibodies are expressed with the prefix hz, e.g., as hz2G10, hz39D2 and hz8G11 antibodies.

The inventors of the present disclosure have made efforts to develop a novel antibody which is capable of preventing or treating cancer (particularly, breast cancer and gastric cancer), exhibits better killing ability (or proliferation-inhibiting ability) for cancer cells which have non-reactivity (or resistance) to the trastuzumab antibody or have reduced sensitivity, and is capable of preventing or treating cancer with improved anticancer activity when co-administered with the trastuzumab antibody as compared to single administration of trastuzumab. As a result, they have developed a novel antibody which exhibits better killing ability for HER2-overexpressed cancer cells on which the trastuzumab antibody hardly acts, or exhibits improved anticancer activity when co-administered with the trastuzumab antibody, and have completed the present disclosure.

The antibody of the present disclosure or an antigen-binding fragment thereof has a specific binding ability for HER2. In particular, among the antibodies of the present disclosure, hz2G10 and hz39D2 bind to an epitope in domain 1 of domains 1-4 of HER2, 24D3 binds to an epitope in domain 3, and 1G3 and hz8G11 bind to an epitope in domain 4, like trastuzumab, which is different from the epitope to which trastuzumab binds.

In the present disclosure, the term "trastuzumab" refers to an antibody disclosed in U.S. Pat. No. 5,821,337.

The antibody of the present disclosure has superior killing ability or proliferation-inhibiting ability for cancer cells which have non-reactivity (or resistance) to the trastuzumab antibody or have reduced sensitivity, when used either alone or in combination with trastuzumab. In the present disclosure, the terms "killing", "proliferation-inhibiting" or "growth-inhibiting" are used interchangeable with the same meaning with regard to cancer cells.

In the present disclosure, the term "antibody" refers to an antibody specific for HER2, and includes not only the whole antibody but also an antigen-binding fragment of the antibody molecule.

A whole antibody has two full-length light chains and two full-length heavy chains. The light chains and heavy chains are connected by disulfide bonds. The constant region of the heavy chain has gamma ($\gamma$), mu ($\mu$), alpha ($\alpha$), delta ($\delta$) and epsilon ($\varepsilon$) types, and has subclasses gamma1 ($\gamma$1), gamma2 ($\gamma$2), gamma3 ($\gamma$3), gamma4 ($\gamma$4), alpha1 ($\alpha$1) and alpha2 ($\alpha$2). The constant region of the light chain has kappa ($\kappa$) and lambda ($\lambda$) types.

In the present disclosure, the term "antigen-binding fragment" refers to a fragment having antigen-binding ability, and includes Fab, F(ab'), F(ab')$_2$, Fv, etc. Among the antibody fragments, Fab (fragment antigen-binding) has a structure having a variable region of the light and heavy chains, a constant region of the light chain and the first constant region (C$_{H1}$) of the heavy chain and has one antigen-binding site. Fab' differs from Fab in that it has a hinge region including at least one cysteine residue at the C-terminus of the heavy chain CH1 domain. In the F(ab')$_2$ antibody, a cysteine residue in the hinge region of Fab' forms a disulfide bond. Recombinant techniques for generating Fv fragments with minimal antibody fragments in which Fv has only the heavy chain variable region and the light chain variable region are known in the related art. A double-chain variable fragment (dcFv) is linked to a heavy chain variable region and a light chain variable region via a non-covalent bond, and a single-chin variable fragment (scFv) is generally linked to covalently to the variable region of a heavy chain via a peptide linker, or to the C-terminus, to form a dimer such as the double-chain Fv. These antibody fragments can be obtained using proteases (for example, Fab can be obtained by cleaving a whole antibody with papain, and the F(ab')2 fragment can be obtained by cleaving with pepsin), or can be prepared using genetic recombination techniques.

Specifically, in the present disclosure, the antibody includes a monoclonal antibody, a multispecific antibody, a human antibody, a humanized antibody, a chimeric antibody, a single-chain Fv (scFv), a single-chain antibody, an Fab fragment, an F(ab') fragment, a disulfide-linked Fv (dsFv), an anti-idiotypic (anti-Id) antibody, and epitope-binding fragments of these antibodies, although not being limited thereto.

In the present disclosure, the term "heavy chain" encompasses a full-length heavy chain including a variable region domain V$_H$ and three constant region domains C$_{H1}$, C$_{H2}$ and C$_{H3}$, including an amino acid sequence having a variable region sequence sufficient for conferring specificity to an antigen, and fragments thereof. Also, in the present disclosure, the term "light chain" encompasses a full-length light chain including a variable region domain V$_L$ and a constant region domain CL, including an amino acid sequence having a variable region sequence sufficient for conferring specificity to an antigen, and fragments thereof.

In the present disclosure, the term "variable region" or "variable domain" refers to a domain of an antibody heavy chain or light chain associated with binding of an antibody to an antigen. In general, the variable domains of a heavy chain and a light chain (V$_H$ and V$_L$, respectively) of a native antibody have similar structures, and each domain includes four conserved framework region (FRs) and three hypervariable regions (HVRs) (Kindt et al., Kuby Immunology, 6th ed., W.H. Freeman and Co., page 91 (2007)).

In the present disclosure, the term "CDR (complementarity-determining region)" refers to the amino acid sequence of the hypervariable region of a heavy chain and a light chain of an immunoglobulin (Kabat et al., Sequences of Proteins of Immunological Interest, 4th ed., U.S. Department of Health and Human Services, National Institutes of Health (1987)). Each of the heavy chain (CDRH1, CDRH2 and CDRH3) and the light chain (CDRL1, CDRL2 and CDRL3) includes three CDRs. The CDR provides major contact residue for binding of an antibody to an antigen or an epitope.

In the present disclosure, the term "framework region" or "FR" refers to a variable domain residue other than a hypervariable region (HVR) residue. The FR of a variable domain generally consists of four FR domains: FR1, FR2, FR3 and FR4. Accordingly, the HVR and FR sequences generally appear in the following order in V$_H$:

FRH1 (framework region 1 of heavy chain)-CDRH1 (complementarity-determining region 1 of heavy chain)-FRH2-CDRH2-FRH3-CDRH3-FRH4.

And, the HVR and FR sequences generally appear in the following order in V$_L$ (or V$_k$):

FRL1 (framework region 1 of light chain)-CDRL1 (complementarity-determining region 1 of light chain)-FRL2-CDRL2-FRL3-CDRL3-FRL4.

In the present disclosure, the term "specific binding" means that an antibody or an antigen-binding fragment thereof, or another construct such as scFv forms a relatively stable complex with an antigen under physiological conditions. The specific binding may be characterized by an equilibrium dissociation constant of about $1 \times 10^{-6}$ M or smaller (e.g., the smaller the K$_d$, the tighter the binding). Methods for determining if two molecules bind specifically are well known in the art, for example, equilibrium dialysis, surface plasmon resonance, etc.

In the present disclosure, the term "affinity" refers to the strength of the sum of noncovalent interactions between a single binding site of a molecule (e.g., an antibody) and its binding partner (e.g., an antigen). Unless specified otherwise, "binding affinity" refers to intrinsic binding affinity which reflects a 1:1 interaction between the members of a binding pair (e.g., an antibody and an antigen). The affinity of a molecule X for its partner Y may generally be represented by a dissociation constant (K$_d$). The affinity can be measured by common methods known in the art, including those described in the present disclosure.

In the present disclosure, the "human antibody" or "humanized antibody" possesses an amino acid sequence which corresponds to an antibody produced by human or a human cell, or an antibody derived from a non-human source that utilizes human antibody repertoires or other human antibody-encoding sequences.

In the present disclosure, the term "chimeric antibody" refers to an antibody in which a portion of the heavy chain and/or light chain is derived from a particular source or species while the remainder of the heavy chain and/or light chain is derived from a different source or species.

The anti-HER2 antibody of the present disclosure or an antigen-binding fragment thereof may include variants of the amino acid sequences described in the attached sequence listings within the scope of specifically recognizing HER2. For example, the amino acid sequence of an antibody may be modified to improve the binding affinity and/or other biological properties of the antibody. Such modification includes, for example, deletion, insertion and/or substitution of the amino acid sequence residue of the antibody.

Such amino acid variation is made based on the relative similarity of amino acid side chain substituents, such as hydrophobicity, hydrophilicity, charge, size, etc. From analysis of the size, shape and type of amino acid side chain substituents, it is recognized that arginine, lysine and histidine are positively charged residues; alanine, glycine and serine have similar sizes; and phenylalanine, tryptophan and tyrosine have similar shapes. Based on these considerations, it is thus recognized that arginine, lysine and histidine; alanine, glycine and serine; and phenylalanine, tryptophan and tyrosine are biologically functional equivalents.

For introduction of mutation, the hydropathy indices of amino acids may be considered. Each amino acid is assigned a hydropathy index according to its hydrophobicity and charge: isoleucine (+4.5); valine (+4.2); leucine (+3.8);

phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydropathy indices of amino acids are very important in imparting the interactive biological function of proteins. It is well known that similar biological activity can be retained when substitution is made with an amino acid having a similar hydropathy index. In this regard, when mutation is introduced, substitution is made between amino acids showing difference in the hydropathy index preferably within ±2, more preferably within ±1, even more preferably within ±0.5.

Meanwhile, it is also well known that substitution between amino acids having similar hydrophilicity values leads to proteins with equivalent biological activity. As disclosed in U.S. Pat. No. 4,554,101, the following hydrophilicity values are assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In this regard, when mutation is introduced, substitution is made between amino acids showing difference in the hydrophilicity value preferably within ±2, more preferably within ±1, even more preferably within ±0.5.

Amino acid substitutions in proteins that do not entirely alter the activity of the molecules are known in the art (H. Neurath, R. L. Hill, The Proteins, Academic Press, New York, 1979). The most commonly occurring substitutions are substitutions between the following amino acid residues: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly.

In an exemplary embodiment of the present disclosure, the heavy chain variable region of the hz2G10 antibody and the 2G10 antibody respectively includes amino acid sequences of SEQ ID NO 31 and 32.

In an exemplary embodiment of the present disclosure, the light chain variable region of the hz2G10 antibody and the 2G10 antibody respectively includes amino acid sequences of SEQ ID NO 35 and 77.

In an exemplary embodiment of the present disclosure, the heavy chain variable region of the hz39D2 antibody and the 39D2 antibody respectively includes amino acid sequences of SEQ ID NO 39 and 83.

In an exemplary embodiment of the present disclosure, the light chain variable region of the hz39D2 antibody and the 39D2 antibody respectively includes amino acid sequences of SEQ ID NO 43 and 85.

In an exemplary embodiment of the present disclosure, the heavy chain variable region of the 24D3 antibody includes an amino acid sequence of SEQ ID NO 47.

In an exemplary embodiment of the present disclosure, the light chain variable region of the 24D3 antibody includes an amino acid sequence of SEQ ID NO 51.

In an exemplary embodiment of the present disclosure, the heavy chain variable region of the 1G3 antibody includes an amino acid sequence of SEQ ID NO 55.

In an exemplary embodiment of the present disclosure, the light chain variable region of the 1G3 antibody includes an amino acid sequence of SEQ ID NO 59.

In an exemplary embodiment of the present disclosure, the heavy chain variable region of the hz8G11 antibody and the 8G11 antibody respectively includes amino acid sequences of SEQ ID NO 63 and 79.

In an exemplary embodiment of the present disclosure, the light chain variable region of the hz8G11 antibody and the 8G11 antibody respectively includes amino acid sequences of SEQ ID NO 67 and 81.

The antibody of the present disclosure includes a monoclonal antibody, a multispecific antibody, a human antibody, a humanized antibody, a chimeric antibody, a single-chain Fv (scFv), a single-chain antibody, an Fab fragment, an F(ab') fragment, a disulfide-linked Fv (dsFv), an anti-idiotypic (anti-Id) antibody, and epitope-binding fragments of these antibodies, although not being limited thereto.

Meanwhile, the antibody of the present disclosure is unique in that its CDR sequence has very low homology (similarity) to the CDR sequences of existing anti-HER2 antibodies. For example, as a result of BLAST search for hz2G10 from among the antibodies of the present disclosure, the highest CDR sequence homology of the antibody of the present disclosure to the antibodies disclosed in U.S. Pat. Nos. 8,314,213 and 8,404,811 was less than 50%. In addition, the antibodies disclosed in U.S. Pat. Nos. 8,314, 213 and 8,404,811 bind to CD25 and EGFL7, respectively, and are different from the antibody of the present disclosure in their targets.

In addition, the anti-HER2 antibody of the present disclosure or an antigen-binding fragment thereof encompasses an anti-HER2 antibody including a slight change in the amino acid sequence described above, including the modification that hardly affects the tertiary structure and function of the antibody, or an antigen-binding fragment thereof. Accordingly, in some exemplary embodiments, the antibody may have an amino acid sequence with at least 90%, 93%, 95% or 98% similarity to the above-described sequence.

Also, in the present disclosure, the heavy chain variable region and the light chain variable region of the antibody or an antigen-binding fragment thereof may be linked by a linker composed of an amino acid sequence represented by the general formula $(G_nS_m)_p$ or $(S_mG_n)_p$.

In the formula, n, m and p satisfy the followings:
n is an integer from 1 to 7;
m is an integer from 0 to 7;
n+m is an integer which is 8 or smaller; and
p is an integer from 1 to 7.

In a specific exemplary embodiment of the present disclosure, n=1-5 and m=0-5. In a more specific exemplary embodiment, n=4 and m=1. In a further more specific exemplary embodiment, the linker is $(G_4S)_3$ or $(S_4G)_3$.

In another exemplary embodiment, the linker is VDGS. In another exemplary embodiment, the linker is ASGS.

In addition, the light chain variable region and the heavy chain variable region of the antibody according to the present disclosure or an antigen-binding fragment may in the following orientations:
light chain variable region-linker-heavy chain variable region; or
heavy chain variable region-linker-light chain variable region.

Another aspect of the present disclosure provides a fusion protein including an anti-HER2 antibody or an antigen-binding fragment thereof.

In the present disclosure, the fusion protein is prepared for the productivity purification efficiency, improved biological activity, increased stability, improved folding and/or binding to a functional moiety for additional function of the anti- HER2 antibody of the present disclosure or an antigen-binding fragment thereof. The fusion protein may be formed as two or more polypeptide chains are linked by a covalent bond, or may be in the form of a conjugate wherein two or more polypeptide chains are linked by chemical conjugation.

Another aspect of the present disclosure provides a chimeric antigen receptor polypeptide including the followings:
(a) an HER2-binding domain;
(b) a transmembrane domain (TM);
(c) a costimulatory domain (domain); and
(d) an intracellular signaling domain (ICD).

In the present disclosure, the term "chimeric antigen receptor (CAR)" refers to an artificially constructed hybrid protein (fusion protein) or polypeptide containing a target-binding domain (e.g. single-chain variable fragment (scFv)) linked to an effector cell-signaling or effector cell-activating domain (e.g. T-cell signaling or T-cell activating domain). In general, the chimeric antigen receptor has the ability of redirecting T-cell specificity and reactivity toward a selected target in a non-MHC restricted manner by taking advantage of the antigen-binding property of a monoclonal antibody. The non-MHC-restricted antigen recognition confers the ability to recognize an antigen on T-cells expressing CAR, thus bypassing the major mechanism of tumor escape. Moreover, when expressed in T-cells, the CAR advantageously does not dimerize with the endogenous T-cell receptor (TCR) alpha and beta chains.

In an exemplary embodiment of the present disclosure, the chimeric antigen receptor of the present disclosure recognizes the HER2 antigen and is expressed on the cell surface since it includes the HER2-binding domain including the anti-HER2 antibody of the present disclosure or an antigen-binding fragment thereof.

The chimeric antigen receptor of the present disclosure includes a transmembrane domain because it is expressed on the cell surface. The transmembrane domain may be a transmembrane domain of a protein selected from a group consisting of the T-cell receptor alpha, beta or zeta chain, CD28, CD3 epsilon, CD45, CD4, CD5, CD8, CD9, CD16, CD22, CD33, CD37, CD64, CD80, CD86, CD134, CD137 and CD154, although not being limited thereto.

In a specific exemplary embodiment of the present disclosure, the transmembrane domain may be a transmembrane domain of CD8 or CD28.

The costimulatory domain of the chimeric antigen receptor of the present disclosure may be a functional signaling domain obtained from a protein selected from a group consisting of MHC class I molecule, TNF receptor protein, immunoglobulin-like protein, cytokine receptor, integrin, signaling lymphocytic activation molecule (SLAM), activating NK cell receptor, BTLA (B- and T-lymphocyte attenuator), Toll-like ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand binding specifically to CD83, although not being limited thereto.

In a specific exemplary embodiment of the present disclosure, the costimulatory domain may be a functional signaling domain obtained from a protein selected from a group consisting of CD28, OX40, 4-1BB (CD137) and/or ICOS (CD278), more specifically a functional signaling domain of CD28 and/or OX40.

In another exemplary embodiment of the present disclosure, the intracellular signaling domain is a functional signaling domain of 4-1BB, CD28, OX40 or CD3 zeta, or a combination thereof. Most specifically, the intracellular signaling domain is a functional signaling domain of CD3 zeta.

The HER2-binding domain of the chimeric antigen receptor of the present disclosure is linked to the transmembrane domain by a hinge domain.

In another exemplary embodiment of the present disclosure, the hinge domain may be IgG4 hinge, CD8 hinge or IgD hinge.

Another aspect of the present disclosure provides a nucleic acid molecule encoding the anti-HER2 antibody or an antigen-binding fragment thereof, or the chimeric antigen receptor polypeptide described above.

In the present disclosure, the term "nucleic acid molecule" encompasses DNA (gDNA and cDNA) and RNA molecules, and the nucleotides that are the basic building blocks of the nucleic acid molecule include not only natural nucleotides but also analogues having modified sugar or base moieties (Scheit, *Nucleotide Analogs*, John Wiley, New York (1980); Uhlman and Peyman, *Chemical Reviews*, 90: 543-584 (1990)).

A nucleotide sequence encoding the antibody of the present disclosure or an antigen-binding fragment thereof, or the chimeric antigen receptor polypeptide is not limited to a specific nucleotide sequence as long as it is a nucleotide sequence encoding the amino acid sequences constituting the chimeric antigen receptor molecule.

This is because the variation in nucleotide sequences may not lead to change in protein sequences through expression. This is called codon degeneracy. Accordingly, the nucleotide sequence includes a nucleotide sequence including functionally equivalent codons, or codons encoding the same amino acid (for example, six codons encode arginine or serine due to codon degeneracy) or codons encoding a biologically equivalent amino acid.

In a specific exemplary embodiment of the present disclosure, the nucleotide sequence encoding the polypeptide constituting the heavy chain CDR, light chain CDR, heavy chain variable region, light chain variable region, heavy chain or light chain of the anti-HER2 antibody of the present disclosure or an antigen-binding fragment thereof is described in the attached sequence listings.

The nucleic acid molecule of the present disclosure, which encodes the anti-HER2 antibody or an antigen-binding fragment thereof, or the chimeric antigen receptor polypeptide, is understood to encompass a nucleotide sequence exhibiting substantial identity for the nucleotide sequence. The substantial identity means that, when the nucleotide sequence of the present disclosure is aligned to another sequence correspond to each other as much as possible and the aligned sequences are analyzed using an algorithm commonly used in the art, the nucleotide sequences exhibit at least 80% homology, more specifically at least 90% homology, most specifically at least 95% homology.

When considering the variation of biologically equivalent activity, it is understood that the nucleic acid molecule encoding the antibody of the present disclosure or an antigen-binding fragment; or the chimeric antigen receptor polypeptide encompasses a sequence exhibiting substantial identity to the sequences described in the sequence listings. The substantial identity means that, when the sequence of the present disclosure and another sequence are aligned to correspond to each other as much as possible and the aligned sequences are analyzed using an algorithm commonly used in the art, the sequences have at least 61% homology, more specifically 70% homology, further more specifically 80% homology, most specifically 90% homology. Methods of the alignment for sequence comparison are known in the art. Various methods and algorithms for the alignment are disclosed in Smith and Waterman, *Adv. Appl. Math.* 2: 482 (1981); Needleman and Wunsch, *J. Mol. Bio.* 48: 443 (1970); Pearson and Lipman, *Methods in Mol. Biol.* 24: 307-31 (1988); Higgins and Sharp, *Gene* 73: 237-44 (1988); Higgins and Sharp, *CABIOS* 5: 151-3 (1989); Corpet et al., *Nuc. Acids Res.* 16: 10881-90 (1988); Huang et al., *Comp. Appl. BioSci.* 8: 155-65 (1992) and Pearson et al., *Meth. Mol. Biol.* 24: 307-31 (1994). The NCBI's basic local alignment search tool (BLAST) (Altschul et al., *J. Mol. Biol.* 215: 403-10 (1990)) is accessible from the NBCI (National Center for Biotechnology Information) and on the Internet and may be used in connection with sequence analysis programs such as blastp, blastn, blastx, tblastn and tblastx. BLAST may be accessed through the BLAST webpage of the NCBI's website. The method for comparing sequence homology using such a program is available from the BLAST help page of the NCBI's website.

Another aspect of the present disclosure provides a recombinant vector including the nucleic acid molecule.

In the present disclosure, the term "vector" includes a delivery vector and an expression vector.

In the present disclosure, the term "delivery vector" refers to a composition of a material which contains an isolated nucleic acid and can be used to deliver the isolated nucleic acid into a cell. It includes a linear polynucleotide, a polynucleotide associated with an ionic or amphiphilic compound, a plasmid and a virus, although not being limited thereto. More specifically, the delivery vector includes a self-replicating plasmid or virus. The term is also construed to include non-plasmid and non-viral compounds which facilitate transfer of nucleic acids into cells, such as, for example, polylysine compounds, liposomes, etc. Examples of the viral delivery vector include an adenoviral vector, an adeno-associated viral vector, a retroviral vector and a lentiviral vector, although not being limited thereto.

In the present disclosure, the term "expression vector" refers to a vector including a recombinant nucleotide including an expression control sequence operably linked to a nucleotide sequence to be expressed for expression of a target gene in a host cell. The expression vector includes a cis-acting element sufficient for expression and other elements for expression can be provided by a host cell or an in-vitro expression system. The expression vector includes a plasmid vector including a recombinant polynucleotide; a cosmid vector; and a viral vector such as a bacteriophage vector, an adenoviral vector, a lentiviral vector, a retroviral vector and an adeno-associated viral vector. In a specific exemplary embodiment of the present disclosure, a nucleic acid molecule encoding a switch molecule is operatively linked to a promoter of the vector of the present disclosure. In the present disclosure, the term "operatively linked" refers to functional linkage between a nucleic acid expression control sequence (e.g., a promoter, a signal sequence, or an array of a transcription factor binding site) and another nucleic acid sequence, wherein the control sequence affects the transcription and/or translation of the another nucleic acid sequence.

The recombinant vector system of the present disclosure may be constructed according to various methods known in the art. Specific methods are described in Sambrook et al., Molecular Cloning, A Laboratory Manual, Cold Spring Harbor Laboratory Press (2001), which is incorporated into the present disclosure by reference.

The vector of the present disclosure may be constructed as a vector for gene cloning, a vector for protein expression, or a vector for gene delivery. In addition, the vector of the present disclosure may be constructed by using a prokaryotic cell or a eukaryotic cell as a host cell.

For example, when the vector of the present disclosure is an expression vector and a eukaryotic cell is used as a host cell, a promoter derived from the genome of a mammalian cell (e.g., metallothionein promoter, β-actin promoter, human hemoglobin promoter and human muscle creatine promoter) or a promoter derived from a mammalian virus (e.g., adenovirus late promoter, vaccinia virus 7.5K promoter, SV40 promoter, cytomegalovirus promoter, tk promoter of HSV, mouse mammary tumor virus (MMTV) promoter, LTR promoter of HIV, Moloney virus promoter, Epstein-Barr virus (EBV) promoter and Rous sarcoma virus (RSV) promoter) may be used, and they generally have a polyadenylation sequence as a transcription termination sequence.

In an exemplary embodiment of the present disclosure, when the vector is a delivery vector, it may be a "retroviral vector". Retrovirus provides a convenient platform for a gene delivery system. A gene selected for gene delivery may be inserted in the retroviral vector and may be packaged within a retroviral particle. Then, the recombinant retrovirus may be delivered to a target host cell in vivo or in vitro. Many retroviral vectors are known in the art. In a specific exemplary embodiment of the present disclosure, the retroviral vector may be a pMT retroviral vector which is an MLV-based retroviral vector, although not being limited thereto.

In another exemplary embodiment of the present disclosure, the vector is a lentiviral vector or an adenoviral vector.

The vector of the present disclosure may be fused with other sequences for easy purification of the polypeptide or protein expressed thereby. For example, the fused sequence may be glutathione S-transferase (Pharmacia, USA), maltose-binding protein (NEB, USA), FLAG (IBI, USA), 6×His (hexahistidine; Quiagen, USA), etc. Meanwhile, the expression vector of the present disclosure may include a selectable marker gene and/or a reporter gene for evaluating the expression of the antibody of the present disclosure or an antigen-binding fragment thereof, or a CAR polypeptide including the same. The selectable marker gene includes an antibiotic-resistant gene commonly used in the art, e.g., genes resistant to ampicillin, gentamicin, carbenicillin, chloramphenicol, streptomycin, kanamycin, geneticin, neomycin and tetracycline. The reporter gene includes luciferase, beta-galactosidase, chloramphenicol, acetyltransferase or green fluorescent protein gene.

Methods for introducing the recombinant vector of the present disclosure into a cell and expressing the same are well known in the related art. The vector may be easily introduced into a host cell, e.g., a mammalian cell, a bacterial cell, a yeast cell or an insect cell according to methods known in the art. For example, the vector may be delivered into a host cell by physical, chemical or biological means. The physical means includes calcium phosphate coprecipitation, lipofection, particle bombardment, microinjection, electroporation, etc. The chemical means includes a colloidal dispersion system, e.g., a macromolecular complex, a nanocapsule, a microsphere, a bead, and a lipid-based system including an oil-in-water emulsion, a micelle, a mixed micelle and a liposome. And, the biological means includes use of a DNA or RNA vector such as a lentiviral vector, a retroviral vector, etc. as described above.

Another aspect of the present disclosure provides a host cell transformed with the recombinant vector.

The host cell capable of cloning and expressing the vector of the present disclosure stably and continuously may be any host cell known in the art. For example, a eukaryotic host cell suitable for the vector includes a monkey kidney cell 7 (COST), an NSO cell, an SP2/0 cell, a Chinese hamster ovary (CHO) cell, a W138 cell, a baby hamster kidney (BHK) cell, a MDCK cell, a myeloma cell, a HuT 78 cell and an HEK-293 cell, although not being limited thereto.

Another aspect of the present disclosure provides an effector cell expressing the chimeric antigen receptor (CAR) polypeptide.

In an exemplary embodiment of the present disclosure, the effector cell is selected from a group consisting of a dendritic cell, a killer dendritic cell, a mast cell, a natural killer cell, a B lymphocyte, a T lymphocyte, a macrophage and precursor cells thereof, although not being limited thereto. The T lymphocyte cell is selected from a group consisting of an inflammatory T lymphocyte, a cytotoxic T lymphocyte, a regulatory T lymphocyte or a helper T lymphocyte.

In the present disclosure, the effector cell includes a group of autologous cells or allogenic cells. That is to say, the effector cell includes a group of autologous cells or allogenic cells expressing the HER2-specific CAR polypeptide.

In another exemplary embodiment of the present disclosure, the effector cell includes a group of cells transfected or transduced with a vector including a nucleic acid molecule encoding the HER2-specific CAR polypeptide. The transfection or transduction may be achieved by various means known in the art without limitation.

Accordingly, in a specific exemplary embodiment of the present disclosure the present disclosure, the HER2-specific CAR-encoding nucleic acid molecule is delivered into an effector cell, e.g., a T lymphocyte or a natural killer cell, and transcribed into mRNA. The HER2-specific CAR polypeptide is translated from the mRNA and expressed on the surface of the effector cell.

Another aspect of the present disclosure provides a pharmaceutical composition for preventing or treating cancer, which contains: (a) a pharmaceutically effective amount of the anti-HER2 antibody of the present disclosure or the antigen-binding fragment thereof described above; and (b) a pharmaceutically acceptable carrier.

Another aspect of the present disclosure provides a pharmaceutical composition for treating cancer or an inflammatory disease, which contains an effector cell expressing the chimeric antigen receptor polypeptide described above.

The pharmaceutical composition is a pharmaceutical composition for immunotherapy, which contains an effector cell expressing the anti-HER2 antibody or an antigen-binding fragment thereof; or the chimeric antigen receptor polypeptide.

In the present disclosure, "immunotherapy" refers to treatment of cancer by activating the immune system. Immunotherapy is classified into active immunotherapy and passive immunotherapy. Active immunotherapy includes i) cancer vaccine therapy of activating the immune system by injecting cancer cells or substances produced by cancer cells into human body, and ii) immunomodulatory therapy of activating specific leukocytes by administering immunomodulatory agents such as cytokines (interferons, interleukins, etc.), growth factors, etc. Passive immunotherapy includes antibody therapy and immune cell therapy. Specifically, immune cell therapy includes dendritic cell vaccine therapy, chimeric antigen receptor T (CAR-T) cell therapy, natural killer (NK) cell therapy, cytotoxic T lymphocyte (CTL) therapy, adoptive cell transfer, etc., although not being limited thereto. In the present disclosure, the immunotherapy mainly refers to antibody therapy using the anti-HER2 antibody and immune cell therapy using the HER2-specific CAR.

The pharmaceutical composition of the present disclosure contains an effector cell expressing the anti-HER2 antibody of the present disclosure or an antigen-binding fragment thereof; the chimeric antigen receptor polypeptide; or the chimeric antigen receptor as an active ingredient. Therefore, description of the details described above will be omitted to avoid redundancy.

As demonstrated in the following examples, the anti-HER2 antibody of the present disclosure exhibits better killing ability for MCF-7 cells on which the trastuzumab antibody hardly acts. In addition, the anti-HER2 antibody of the present disclosure exhibits improved killing ability for SKBR3 breast cancer cells when co-administered with trastuzumab. Accordingly, the composition of the present disclosure is very effective for combined administration with the trastuzumab antibody for treatment of cancer and for treatment of cancer not treated with trastuzumab.

The cancer that can be prevented or treated by the composition of the present disclosure includes various cancers known in the art. For example, it includes breast cancer, ovarian cancer, gastric cancer, lung cancer, liver cancer, bile duct cancer, bronchial cancer, nasopharyngeal cancer, laryngeal cancer, pancreatic cancer, bladder cancer, kidney cancer, colorectal cancer, colon cancer, cervical cancer, brain cancer, prostate cancer, bone cancer, head and neck cancer, skin cancer, thyroid cancer, parathyroid cancer or ureteral cancer.

Specifically, the cancer that can be prevented or treated by the composition of the present disclosure is HER2-expressing cancer, more specifically HER2-expressing breast cancer or gastric cancer.

The pharmaceutically acceptable carrier contained in the pharmaceutical composition of the present disclosure is one commonly used in preparation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain a lubricant, a wetting agent, a sweetener, a flavor, an emulsifier, a suspending agent, a preservative, etc. in addition to the above-described ingredients. Suitable pharmaceutically acceptable carriers and preparations are described in detail in Remington's Pharmaceutical Sciences (19th ed., 1995).

The pharmaceutical composition of the present disclosure may be administered orally or parenterally. For example, it may be administered intravenously, subcutaneously, intramuscularly, intraperitoneally, topically, intranasally, intrapulmonarily, intrathecally, ocularly, intradermally, transdermally, etc.

An administration dosage of the pharmaceutical composition of the present disclosure varies depending on such factors as formulation method, administration method, the age, body weight, sex of a patient, pathological condition, food, administration time, administration route, excretion rate and responsiveness. A normally trained physician can easily determine and prescribe an administration dosage for effective treatment or prevention. In a specific exemplary embodiment of the present disclosure, a daily administration dosage of the pharmaceutical composition of the present disclosure is 0.0001-100 mg/kg. In the present disclosure, the term "pharmaceutically effective amount" refers to an amount sufficient for preventing or treating cancer.

The pharmaceutical composition of the present disclosure may be formulated into a unit-dosage form or a multiple-dosage form using a pharmaceutically acceptable carrier and/or excipient according to a method that can be easily employed by those of ordinary skill in the art to which the present disclosure belongs. The formulation may be in the form of a solution in an oily or aqueous medium, a suspension, an emulsion, an extract, a pulvis, a suppository, a powder, a granule, a tablet or a capsule, and may further contain a dispersant or a stabilizer.

In an exemplary embodiment of the present disclosure, the pharmaceutical composition of the present disclosure may further contain the trastuzumab antibody.

The pharmaceutical composition of the present disclosure may further contain, in addition to the active ingredient derived above, another pharmaceutically active medication or drug, e.g., a chemotherapy agent such as asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc., a targeted therapy agent such bevacizumab, olaparib, etc., or an immune checkpoint inhibitor such as nivolumab or pembrolizumab, or may be co-administered with them.

Another aspect of the present disclosure provides a method for treating cancer, which includes a step of administering a composition containing an effector cell expressing the anti-HER2 antibody or an antigen-binding fragment thereof; or the HER2-specific chimeric antigen receptor to a subject in need of treatment.

The cancer to be treated by the therapeutic method of the present disclosure is the same as defined above with regard to the pharmaceutical composition.

In an exemplary embodiment of the present disclosure, the subject may be a mammal or human.

Since the method for treating cancer or an inflammatory disease of the present disclosure uses an effector cell expressing the antibody or an antigen-binding fragment; or the chimeric antigen receptor described above as an active ingredient, description of the details described above will be omitted to avoid redundancy.

The anti-HER2 antibody or an antigen-binding fragment thereof described above may be used for diagnosis, e.g., diagnosis of cancer.

Accordingly, another aspect of the present disclosure provides a kit for diagnosing cancer, which includes the anti-HER2 antibody of the present disclosure or an antigen-binding fragment thereof.

Since the diagnostic kit of the present disclosure includes the anti-HER2 antibody of the present disclosure or an antigen-binding fragment thereof described above and diagnoses the same disease as described above with regard to the pharmaceutical composition of the present disclosure, description of the details described above will be omitted to avoid redundancy.

Since the kit includes an antibody, it can be prepared to be suitable for various immunoassay or immunostaining applications. The immunoassay or immunostaining includes radioimmunoassay, radioimmunoprecipitation, immunoprecipitation, enzyme-linked immunosorbent assay (ELISA), capture ELISA, inhibition or competition assay, sandwich assay, flow cytometry, immunofluorescence staining and immunoaffinity purification, although not being limited thereto. Methods for the immunoassay or immunostaining are described in Enzyme Immunoassay, E. T. Maggio, ed., CRC Press, Boca Raton, Florida, 1980; Gaastra, W., Enzyme-linked immunosorbent assay (ELISA), in Methods in Molecular Biology, Vol. 1, Walker, J. M. ed., Humana Press, N J, 1984; and Ed Harlow and David Lane, Using Antibodies: A Laboratory Manual, Cold Spring Harbor Laboratory Press, 1999, which are incorporated in the present disclosure by reference.

For example, when the method of the present disclosure is carried out by radioimmunoassay, an antibody labeled with a radioisotope (e.g., $C^{14}$, $I^{125}$, $P^{32}$ or $S^{35}$) may be used to detect the HER2 protein. When the method of the present disclosure is carried out by ELISA, a specific exemplary embodiment of the present disclosure includes: (i) a step of coating a sample to be analyzed on the surface of a solid substrate; (ii) a step of reacting the sample with the anti-HER2 antibody of the present disclosure as a primary antibody; (iii) a step of reacting the resultant of the step (ii) with a secondary antibody coupled with an enzyme; and (iv) a step of measuring the activity of the enzyme.

Appropriate examples of the solid substrate are a hydrocarbon polymer (e.g., polystyrene or polypropylene), glass, a metal or a gel, most specifically, a microtiter plate.

The enzyme coupled with the secondary antibody may include an enzyme that catalyzes chromogenic reaction, fluorescence reaction, luminescent reaction or infrared reaction, although not being limited thereto. For example, it includes alkaline phosphatase, β-galactosidase, horseradish peroxidase, luciferase and cytochrome P450. When alkaline phosphatase is used as the enzyme coupled with the secondary antibody, a chromogenic substrate such as bromochloroindolyl phosphate (BCIP), nitro blue tetrazolium (NBT), naphthol-AS-B1-phosphate and enhanced chemifluorescence (ECF) may be used as the substrate. When horseradish peroxidase is used, a substrate such as chloronaphthol, aminoethylcarbazole, diaminobenzidine, D-luciferin, lucigenin (bis-N-methylacridinium nitrate), resorufin benzyl ether, luminol, Amplex Red (10-acetyl-3,7-dihydroxyphenoxazine), HYR (p-phenylenediamine-HCl and pyrocatechol), tetramethylbenzidine (TMB), 2,2-azino-di[3-ethylbenzthiazoline sulfonate] (ABTS), o-phenylenediamine (OPD), naphthol/pyronin, glucose oxidase, t-NBT (nitro blue tetrazolium) and m-PMS (phenzaine methosulfate) may be used.

When the method of the present disclosure is carried out by capture ELISA, the method includes: (i) a step of coating the HER2 antibody as a capture antibody on the surface of a solid substrate; (ii) a step of reacting the capture antibody with a sample; (iii) a step of reacting the resultant of the step (ii) with an HER2 detection antibody conjugated with a label; and (iv) a step of measuring a signal generated from the label.

The anti-HER2 antibody of the present disclosure has a label that generates a signal that can be detected by the detection antibody. The label includes a chemical substance (e.g., biotin), an enzyme (alkaline phosphatase, β-galactosidase, horseradish peroxidase or cytochrome P450), a radioactive substance (e.g., $C^{14}$, $I^{125}$, $P^{32}$ and $S^{35}$) a fluorescent material (e.g., fluorescein), a light-emitting material, a chemiluminescent material and a FRET (fluorescence resonance energy transfer) material, although not being limited thereto. Various labels and labeling method are described in Ed Harlow and David Lane, Using Antibodies: A Laboratory Manual, Cold Spring Harbor Laboratory Press, 1999.

In the ELISA method and the capture ELISA, the measurement of the enzyme activity or the measurement of the signal may be carried out according to various methods known in the art. The signal may be detected easily by using streptavidin when biotin is used as the label, and using luciferin when luciferase is used.

The sample to which the kit of the present disclosure can be applied includes a cell, a tissue, a tissue-derived extract, a lysate, a purification product, a blood, a plasma, a serum, a lymph or ascites, although not being limited thereto.

The antibody of the present disclosure may be used in in-vivo or in-vitro imaging.

Another aspect of the present disclosure provides a composition for imaging, which contains a conjugate in which the antibody of the present disclosure is conjugated to a label generating a detectable signal.

The label generating a detectable signal includes a T1 contrast agent (e.g., a Gd chelate compound), a T2 contrast agent (e.g., a superparamagnetic material (e.g., magnetite, $Fe_3O_4$, $\gamma$-$Fe_2O_3$, manganese ferrite, cobalt ferrite and nickel ferrite)), a radioiosotope (e.g., $^{11}C$, $^{15}O$, $^{13}N$, $P^{32}$, $S^{35}$, $^{44}Sc$, $^{45}Ti$, $^{118}I$, $^{136}La$, $^{198}Tl$, $^{200}Tl$, $^{205}Bi$ and $^{206}Bi$), a fluorescent material (fluorescein, phycoerythrin, rhodamine, lissamine, Cy3 and Cy5), a chemiluminescent material, a magnetic particle, a mass label or an electron-dense particle, although not being limited thereto.

Advantageous Effects

The features and advantages of the present disclosure may be summarized as follows:
(a) The antibody of the present disclosure or an antigen-binding fragment is an antibody that specifically binds to HER2 which is highly expressed in cancer cells (particularly, breast cancer or gastric cancer cells), and binds to an epitope that is different from an epitope to which trastuzumab binds. The present disclosure provides the antibody or the antigen-binding fragment, a chimeric antigen receptor including the same, and uses thereof.
(b) The antibody of the present disclosure or an antigen-binding fragment is unique in that its CDR sequence has very low homology to the CDR sequences of existing HER2-targeting antibodies.
(c) When compared with trastuzumab, the antibody of the present disclosure exhibits better killing ability for HER2-unexpressed cancer cells which have non-reactivity (or resistance) to the trastuzumab antibody or have reduced sensitivity. In addition, when the anti-HER2 antibody of the present disclosure is administered in combination with trastuzumab, a synergistic killing ability is achieved for cancer cells on which the trastuzumab antibody acts. Therefore, a composition of the present disclosure can be very usefully used for combined administration with the trastuzumab antibody for the treatment of cancer, or for the treatment of cancer not treated with trastuzumab. In particular, when expressed in effector cells such as T lymphocytes, etc., the chimeric antigen receptor including the anti-HER2 antibody of the present disclosure or an antigen-binding fragment may be usefully used for immune cell therapy of various HER2-related cancers.
(d) Without wishing to be bound by theory, it is considered that the antibody of the present disclosure exhibits the above-described effects since it binds to an epitope that is different from an epitope to which trastuzumab binds and inhibits HER2 in a different manner from that of trastuzumab.

BEST MODE FOR CARRYING OUT INVENTION

Figure 1:
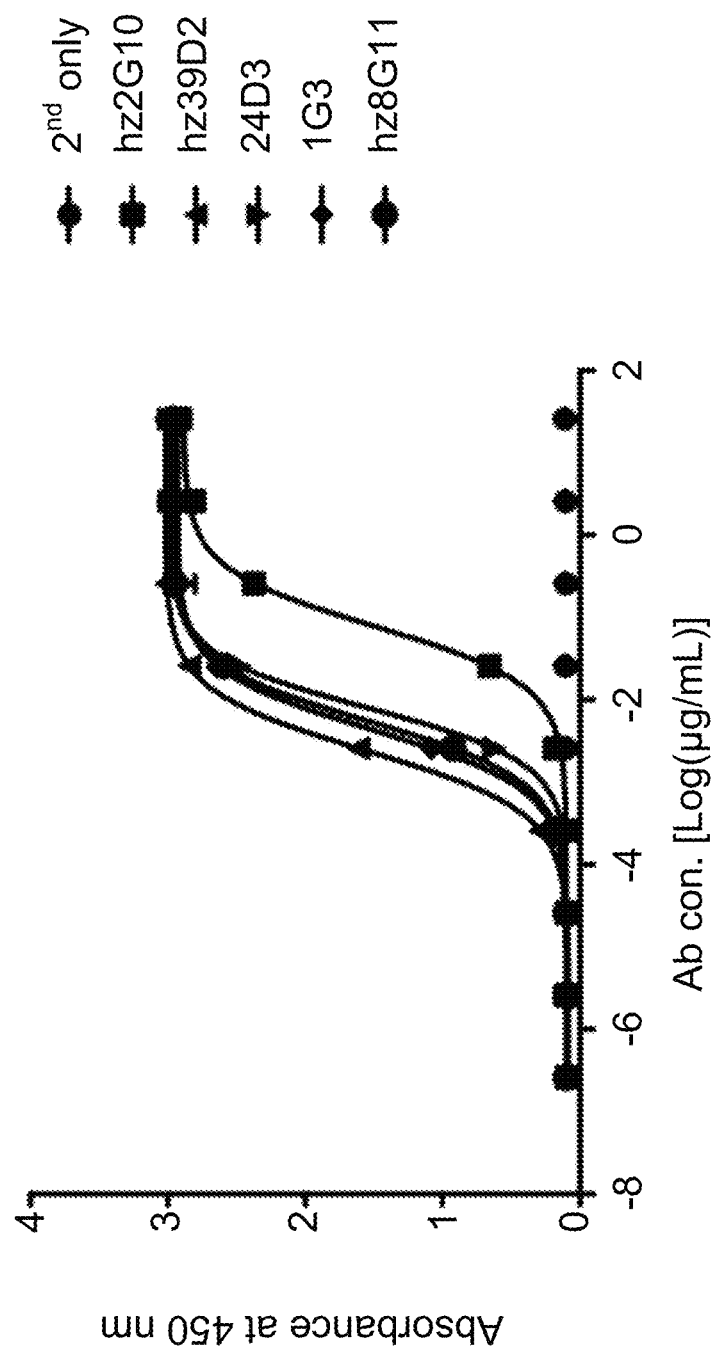
FIG. 1 shows a result of analyzing the affinity of hz2G10, hz39D2, 24D3, 1G3 and hz8G11 clones for the HER2-ECD-Fc antigen by ELISA.

Hereinafter, the present disclosure will be described in detail through examples. However, the following examples are for illustrative purposes only and it will be apparent to those of ordinary skill in the art that the scope of the present disclosure is not limited by the examples.

EXAMPLES

Example 1: Development of Anti-HER2 Antibody

For development of antibodies, the extracellular domain (ECD) of the HER2 protein was produced using animal cells. The DNA in which a hinge and an Fc region ($CH_2$—$CH_3$) of human IgG1 were bound to the C-terminus of ECD was cloned into pCEP4 (Invitrogen, Cat. No. V044-50) using HindIII and BamHI restriction enzymes. Then, the cloned vector was transiently transformed into FreeStyle 293F (Invitrogen, Cat. No. R790-07) cells using polyethyleneimine (Polyscience Inc., Cat. No. 23966) and then purified from the cell culture using a Protein-A Ceramic HyperD F resin (PALL, Cat No. 20078-028). The purified protein was quantitated using a protein assay dye (Bio-Rad, Cat. No. 500-0006) and its concentration and purity were investigated via Coomassie Blue staining following SDS-PAGE. 100 µg of the protein antigen was mixed with a Freund's adjuvant (Sigma, Cat. No. F5506) and then injected intraperitoneally into BALB/c mouse (Dae Han Bio). 2 weeks later, 100 µg of the antigen diluted in PBS was injected further. 3 days later, the spleen of the mouse was taken out and lymphocytes were isolated. The isolated lymphocytes were mixed with SP2/0-Ag14 myeloma cells (ATCC, Cat. No. CRL-1581) at a ratio of 5:1 and then fused using PEG-1500 (Roche, Cat. No. 783641). The fused cells (hybridoma) were selectively sorted out and cultured in a medium containing a HAT supplement (Sigma, Cat. No. H0262).

The obtained hybridoma cells were examined via ELISA to determine whether they were the cells producing an antibody that bind to the antigen. HER2-ECD-Fc or ChromPure human IgG (hIgG, Jackson Immunoresearch Lab. Inc., Cat. No. 009-000-003) was immobilized at room temperature onto a Costar 96-well plate (Corning, Cat. No. 3590) at a concentration of 1 µg/mL for 1 hour. The resultant was washed 3 times with TBS-T (0.05% Triton X-100) and then blocked at room temperature for 30 minutes with 300 µL of TBS-T/SM (2% skim milk). After washing the blocked plate 3 times and adding the hybridoma culture, the antibody was allowed to bind at 37° C. for 1 hour. After washing 3 times and then adding anti-mIgG-HRP (Pierce, Cat. No. 31439) diluted to 1:5,000 in TBS-T/SM, as a secondary antibody, the antibody was allowed to bind at 37° C. for 1 hour. After washing the resultant 3 times and adding TMB (SurModics, Cat. No. TMBC-1000-01), the mixture was allowed to develop color at room temperature for 5 minutes. Then, the color development was stopped by adding 1 N sulfuric acid (DukSan, Cat. No. 254). Absorbance was measured at 450 nm using Victor X3 (PerkinElmer, Cat. No. 2030-0030) and the antibody binding specifically to HER2-ECD-Fc was selected.

Since HER2 is a protein expressed on cell surface, it was investigated whether the developed antibody was bound to HER2-overexpressing cells via cell-based ELISA. HER2-overexpressing SKOV-3 ovary cancer cells (Korean Cell Line Bank, Cat. No. 30077) were aliquoted onto a Costar 96-well cell culture plate (Corning, Cat. No. 3595) at 10,000 cell/well and then cultured for 24 hours. On the following day, after removing the cell culture supernatant, the resultant was washed 3 times with PBS and cultured further at 37° C. for 2 hours after adding the hybridoma cell culture. After washing 3 times with TBS-T and adding goat anti-mIgG-HRP diluted in PBS/FBS (3% FBS) to 1:5,000, as a secondary antibody, the resultant was treated at room temperature for 1 hour. After washing 3 times with TBS-T, it was allowed to develop color using TMB. 61 clones showing higher absorbance than that of the SP2/0 cell culture as a negative control group were selected.

The five antibodies (hz2G10, hz39D2, 24D3, 1G3, hz8G11) finally selected from the monoclonal antibodies binding specifically to HER2 were modified to chimeric antibodies or humanized antibodies (hz). The amino acid sequences of the chimeric antibodies or humanized antibodies are described in the attached sequence listings.

The absorbance of the finally selected five antibodies (hz2G10, hz39D2, 24D3, 1G3, hz8G11) is shown in FIG. 1 and Table 1.

Verification of Binding of HER2 Proteins of Five Selected Antibodies to Extracellular Domain (ECD)

| Antibodies | Concentration (µg/mL) | | | | | | | | |
|---|---|---|---|---|---|---|---|---|---|
| | $5 \times 10^{-7}$ | $5 \times 10^{-6}$ | $5 \times 10^{-5}$ | $5 \times 10^{-4}$ | $5 \times 10^{-3}$ | $5 \times 10^{-2}$ | $5 \times 10^{-1}$ | 5 | 50 |
| PBS | 0.13 | 0.13 | 0.14 | 0.14 | 0.14 | 0.13 | 0.16 | 0.15 | 0.14 |
| hz2G10 | 0.12 | 0.12 | 0.12 | 0.12 | 0.22 | 1.16 | 2.69 | 2.79 | 2.81 |
| hz39D2 | 0.12 | 0.12 | 0.15 | 0.47 | 2.29 | 2.92 | 2.78 | 2.90 | 2.83 |
| 24D4 | 0.11 | 0.11 | 0.12 | 0.22 | 1.13 | 2.76 | 2.90 | 2.92 | 2.75 |
| 1G3 | 0.11 | 0.11 | 0.14 | 0.35 | 1.77 | 2.79 | 2.78 | 2.81 | 2.76 |
| hz8G11 | 0.12 | 0.12 | 0.14 | 0.34 | 1.67 | 2.72 | 2.94 | 2.90 | 2.74 |

Example 2: Verification of Binding Site of Developed Antibody for HER2 Protein

The binding site of the selected five antibodies (hz2G10, hz39D2, 24D3, 1G3, hz8G11) for the extracellular domain (ECD) of the HER2 protein was verified by ELISA. For ELISA, the extracellular domain (ECD) of the ERBB family protein was produced using animal cells and was used as an antigen. Specifically, the DNA in which a hinge and an Fc region ($CH_2$—$CH_3$) of human IgG1 were bound to the C-terminus of ECD was cloned into pCEP4 (Invitrogen, Cat. No. V044-50) using HindIII and BamHI restriction enzymes. Then, the cloned vector was transiently transformed into FreeStyle 293F (Invitrogen, Cat. No. R790-07) cells using polyethyleneimine (Polyscience Inc., Cat. No. 23966) and then HER2-ECD DI Fc, HER2-ECD DII Fc, HER2-ECD DIII Fc, HER2-ECD DIV Fc and HER2-ECD Fc fusion proteins were purified from the cell culture using a Protein-A Ceramic HyperD F resin (PALL, Cat No. 20078-028). The purified protein was quantitated using a protein assay dye (Bio-Rad, Cat. No. 500-0006) and its concentration and purity were investigated via Coomassie Blue staining following SDS-PAGE.

The HER2-ECD DI Fc, HER2-ECD DII Fc, HER2-ECD DIII Fc, HER2-ECD DIV Fc and HER2-ECD Fc fusion proteins were immobilized at 4° C. overnight onto a Costar 96-well plate (Corning, Cat. No. 3590) at a concentration of 1 µg/mL for 1 hour. The resultant was washed 3 times with TBS-T (0.05% Triton X-100) and then blocked at room temperature for 1 hour with 100 µL of TBS-T/BSA (5% BSA). After washing the blocked plate 3 times and adding the anti-HER2 antibody, the antibody was allowed to bind at room temperature for 1 hour. After washing 3 times and then adding anti-human IgG-HRP diluted to 1:3,000 in TBS-T/BSA, as a secondary antibody, the antibody was allowed to bind at room temperature for 1 hour. After washing the resultant 3 times and adding TMB (SurModics, Cat. No. TMBC-1000-01), the mixture was allowed to develop color at room temperature for 5 minutes. Then, the color development was stopped by adding 1 N sulfuric acid (DukSan, Cat. No. 254). Absorbance was measured at 450 nm using Victor X3 (PerkinElmer, Cat. No. 2030-0030).

Figure 2:
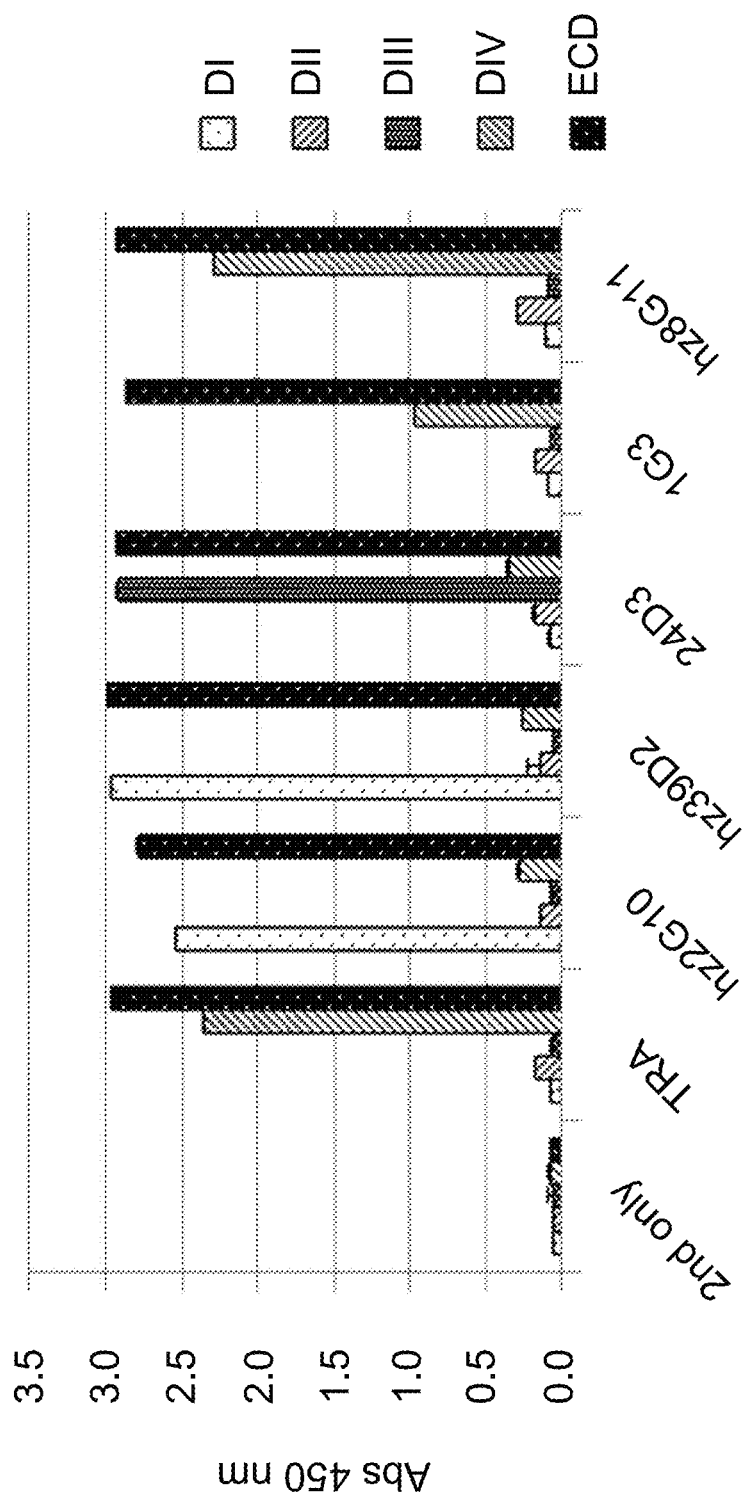
FIG. 2 shows a result of investigating the extracellular domain of HER2 to which hz2G10, hz39D2, 24D3, 1G3 and hz8G11 clones bind.

The result is shown in FIG. 2.

As show in FIG. 2, among the antibodies developed in the present disclosure, hz2G10 and hz39D2 were bound to the domain 1 of the extracellular domains of the HER2 protein, 24D3 was bound to the domain 3, and 1G3 and hz8G11 were bound to the domain 4.

From this result, it can be seen that the five antibodies of the present disclosure can inhibit the growth of the HER2-overexpressed cancer cells by binding to the HER domain which is different from the extracellular domain 4 of the HER2 protein to which trastuzumab (TRA) binds (hz2G10, hz39D2, 24D3), or can exhibit remarkably superior effect of inhibiting cellular growth when used alone or co-administered with trastuzumab. Therefore, they can be usefully used for prevention or treatment of cancer related with the expression of the HER2 proteins either alone or together with trastuzumab.

Example 3: Comparison of Inhibitory Effect of Developed Antibody Against Growth of Breast Cancer Cells Cell viability was analyzed by treating HER2-overexpressed SKBR3 breast cancer cells or HER2-unexpressed breast cancer cells with MCF-7 either alone or together with trastuzumab. For co-administration, the developed antibody and trastuzumab were mixed at a weight ratio of 1:1. SKBR3 cells (Korean Cell Line Bank, Cat. No. 30030, 5,000 cells/well) and MCF-7 cells (ATCC, Cat. No. HTB22, 5,000 cells/well) were aliquoted onto a 96-well plate and cultured for 24 hours. The cells were cultured further for 4 days after treating with the purified antibody at a final concentration of 20 μg/mL. For measurement of cell viability, CCK-8 (Dojindo, Cat. No. CK-04-13) was added to a final concentration of 10% and absorbance was measured after treating at 37° C. for 3 hours. Relative cell viability was calculated with respect to the absorbance of the antibody-untreated well as 100%.

The result is shown in FIGS. 3a-3d and Table 2.

Relative Cell Viability of HER2-Positive SKBR3 Breast Cancer Cells and HER2-Negative MCF-7 Breast Cancer Cells Treated with Antibody (Single Treatment)

| Relative cell viability at 20 μg/mL (%) | | |
|---|---|---|
| Clones | SKBR3 | MCF-7 |
| hIgG | 94.68 | 92.11 |
| TRA (trastuzumab) alone | 63.68 | 98.22 |
| hz2G10 | 89.06 | 97.43 |
| hz39D2 | 96.46 | 91.42 |
| 24D3 | 93.97 | 87.33 |
| 1G3 | 74.81 | 98.66 |
| hz8G11 | 74.02 | 98.95 |

Figure 3A:
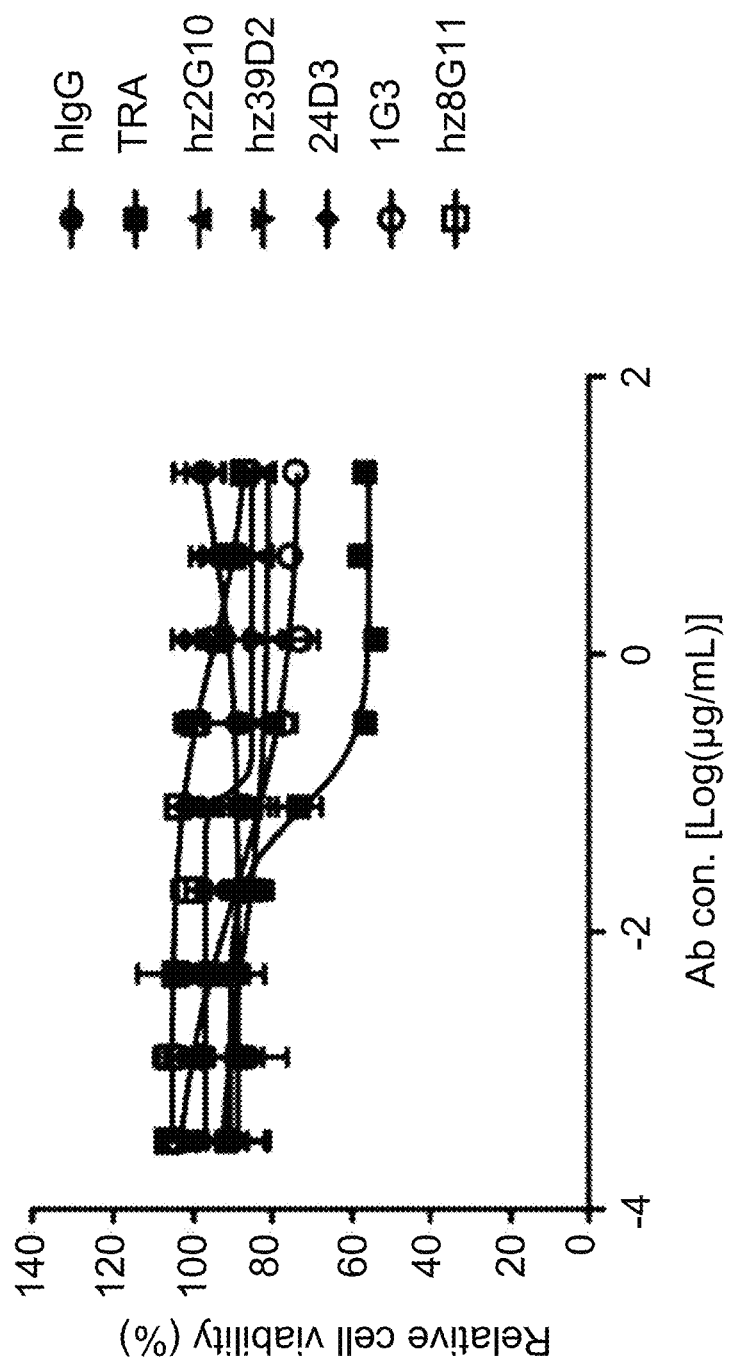
FIG. 3a and FIG. 3b show a result of analyzing the effect of single administration of five antibodies of the present disclosure (hz2G10, hz39D2, 24D3, 1G3 and hz8G11) on the inhibition of the growth of HER2-overexpressed breast cancer cells (SKBR3) and HER2-unexpressed breast cancer cells (MCF-7).
Figure 3B:
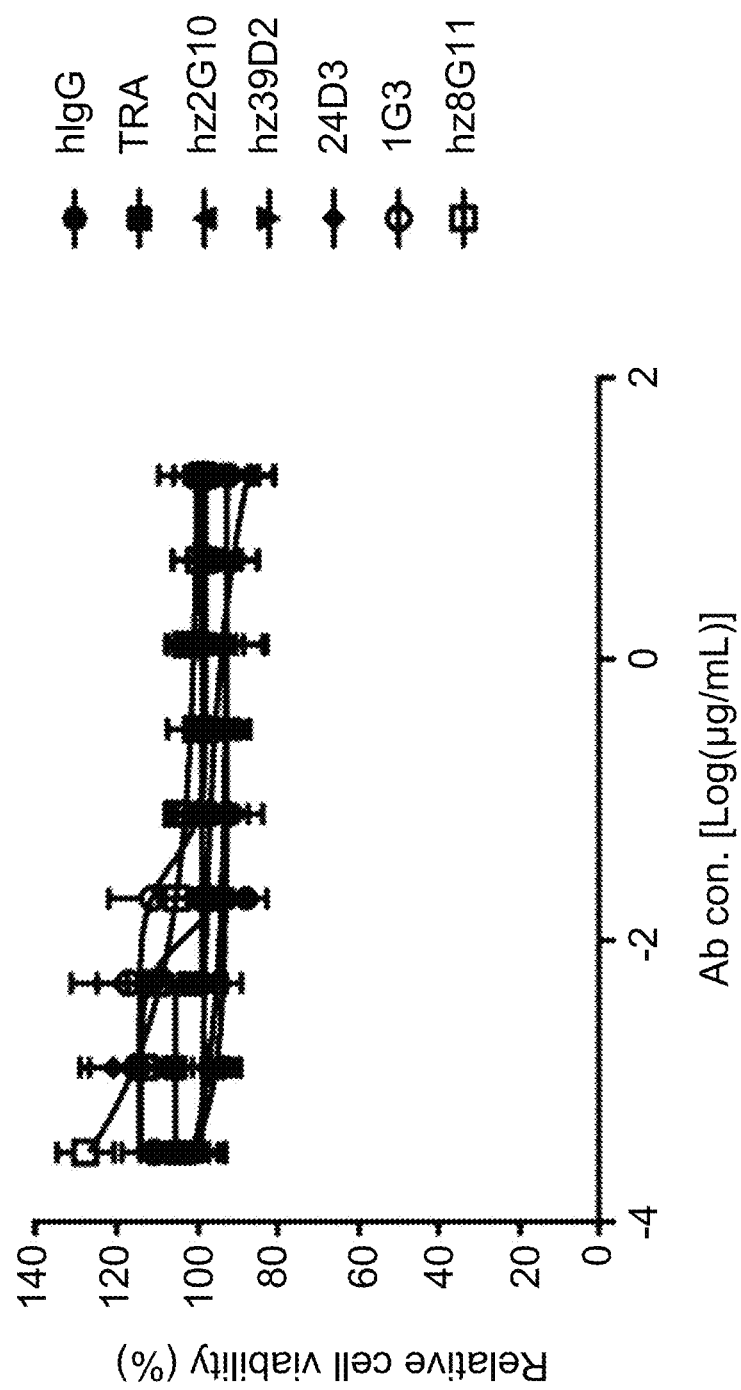

In the above table, hIgG stands for human IgG. As seen from FIG. 3a, FIG. 3b and Table 2, the five antibodies of present disclosure showed the effect of inhibiting the proliferation of SKBR3 breast cancer cells when treated alone. They showed comparable or better effect of inhibiting cellular growth as compared to the positive control trastuzumab at different concentrations (FIG. 3a). However, the five antibodies of present disclosure did not show significant effect of inhibiting cell proliferation of the HER2-negative MCF-7 cells like the positive control trastuzumab (FIG. 3b).

Relative Cell Viability of HER2-Positive SKBR3 Breast Cancer Cells and HER2-Negative MCF-7 Breast Cancer Cells Treated with Antibody (Co-Treatment)

| Relative cell viability at 20 μg/mL (%) | | |
|---|---|---|
| Clones | SKBR3 | MCF-7 |
| hIgG | 94.68 | 92.11 |
| TRA (trastuzumab) alone | 63.68 | 98.22 |
| TRA + hz2G10 | 68.98 | 90.56 |
| TRA + hz39D2 | 77.29 | 90.62 |
| TRA + 24D3 | 63.75 | 97.21 |
| TRA + 1G3 | 62.16 | 102.33 |
| TRA + hz8G11 | 52.62 | 98.41 |

Figure 3C:
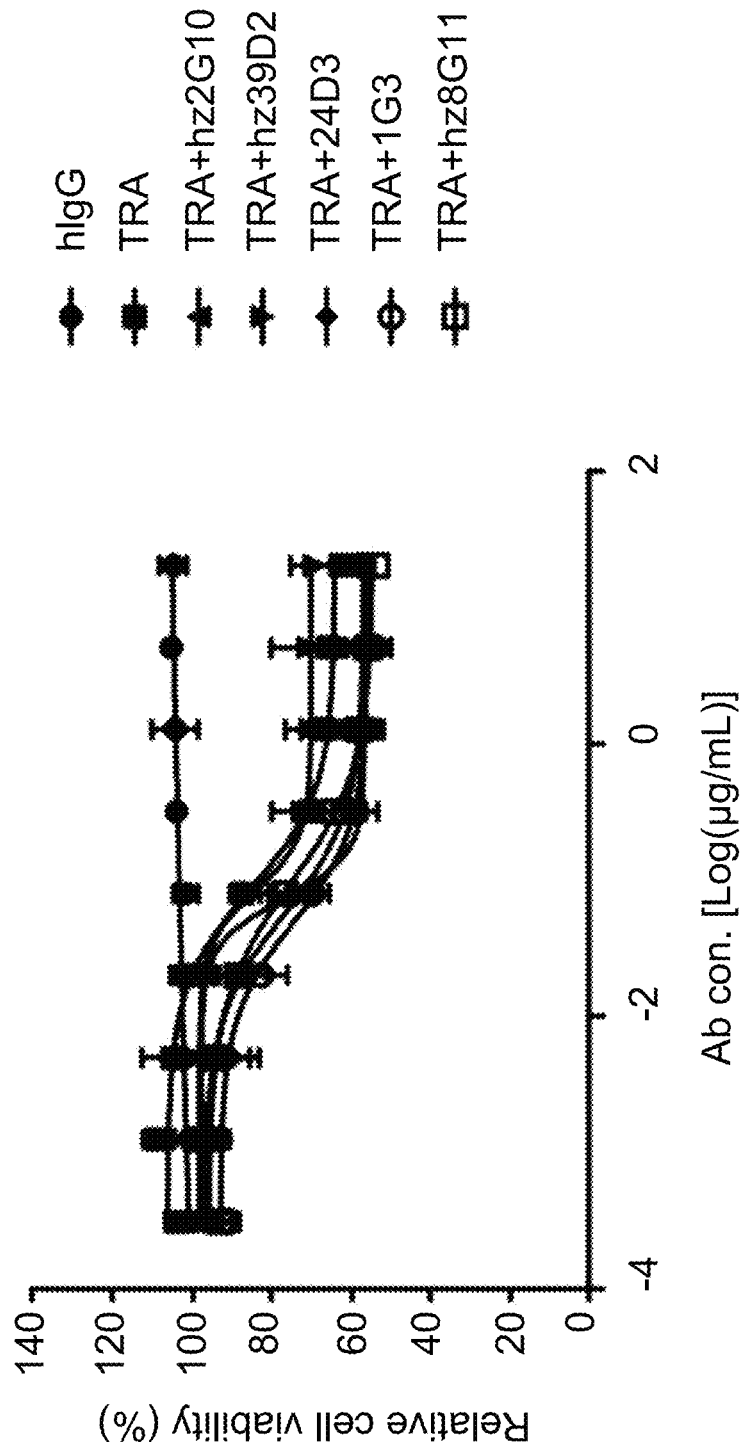
FIG. 3c and FIG. 3d show a result of analyzing the effect of co-administration of five antibodies of the present disclosure (hz2G10, hz39D2, 24D3, 1G3 and hz8G11) and the trastuzumab (TRA) antibody on the inhibition of the growth of HER2-overexpressed breast cancer cells (SKBR3) and HER2-unexpressed breast cancer cells (MCF-7).
Figure 3D:
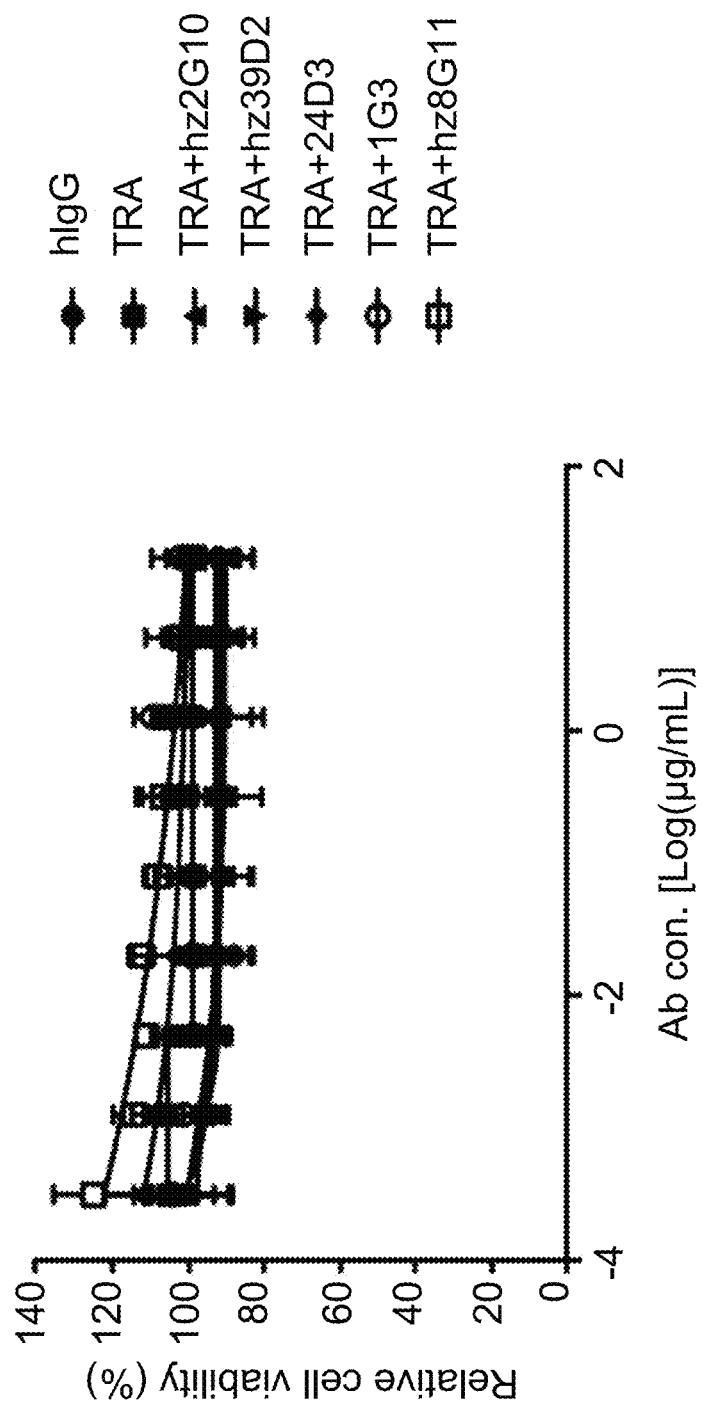

In the above table, hIgG denotes the test group treated with human IgG, and TRA+ denotes the test groups co-administered with trastuzumab and the antibody of the present disclosure. As seen from FIG. 3c, FIG. 3d and Table 3, all of the five antibodies of present disclosure (hz2G10, hz39D2, 24D3, 1G3, hz8G11) showed comparable or better effect of inhibiting cellular growth when treated to the SKBR3 breast cancer cells together with trastuzumab as compared to single treatment with trastuzumab (FIG. 3c).

Without wishing to be bound by theory, it is considered that the antibody of the present disclosure exhibits the above-described effect since it binds to an epitope on HER2 that is different from an epitope to which trastuzumab binds and inhibits HER2 in a different manner from that of trastuzumab.

Example 4: Antibody Sequence Analysis

For analysis of the antibody sequence, a phage Fab antibody library was constructed using the respective hybridoma RNAs and a 3-step panning was conducted to obtain a phage that binds to HER2-ECD-Fc (Phage display: a laboratory manual, Carlos Barbas III, et al., Cold Spring Harbor Laboratory Press). After culturing the hybridoma, RNA was isolated using the SV total RNA isolation system (Promega, Cat. No. Z3100) and cDNA was synthesized therefrom. Using a known primer set (see Phage display: a laboratory manual, Carlos Barbas III, et al., Cold Spring Harbor Laboratory Press), the variable region of the antibody was amplified and cloned into the pComb3X vector (Barbas Laboratory, Scripps Research Institute) using a Sfi-I restriction enzyme after ligating to human Ck (kappa chain) and CH1, and then transformed into ER2537 bacteria (New England Biolabs, Cat. No. 801-N). The transformed bacteria were transfected with the VCSM13 helper phage (Stratagene, Cat. No. 200251) and a clone which binds to HER2-ECD-Fc was obtained using an immunotube to which HER2-ECD-Fc was immobilized.

From the colonies of the antibodies, the antibody that binds to HER2-ECD-Fc was confirmed via ELISA. The colonies of the transformed bacteria were cultured at 37° C. until the absorbance at 600 nm reached 0.5, treated with IPTG at a final concentration of 1 mM, and allowed to express antibodies in the form of Fab while culturing overnight at 30° C. After collecting cells by centrifuging 5 mL of the culture, the cells were suspended in 0.4 mL of 1×TES (50 mM Tris, 1 mM EDTA, 20% (v/v) sucrose, pH 8.0) and then treated at 4° C. for 10 minutes. After adding 0.6 mL of 0.2×TES thereto and treating further at 4° C. for 30 minutes, the resultant was centrifuged and a supernatant was taken. After washing a Costar 96-well half area plate (Corning Inc., Cat. No. 3690) coated with HER2-ECD-Fc at a concentration of 1 µg/mL 3 times with TBS-T, it was blocked with TBS-T/SM (3% non-fat skim milk, 0.05% Triton X-100) at room temperature for 1 hour. The culture broth or periplasmic extract (periplasm) of each colony was diluted at a ratio of 1:3 using TBS-T/SM and allowed to bind at room temperature for 1 hour. After washing 3 times and diluting to 1:5000 with anti-HA-HRP (Roche, Cat. No. 120-138-190-01) as a secondary antibody, the resultant was allowed to bind at room temperature for 1 hour. After washing 3 times, the resultant was allowed to develop color using TMB.

Most colonies showed absorbance of 0.2 or higher in the cell culture or periplasmic extract, and the base sequence of the antibody was analyzed for these clones. The base sequence analysis revealed that the colonies derived from the single hybridoma had the same sequences.

The CDR sequence of the antibody produced from each clone is summarized in Table 4 and Table 5.

TABLE 4

| Clones | CDRH1 | CDRH2 | CDRH3 |
|---|---|---|---|
| hz2G10 | DYYMY (SEQ ID NO 1) | YINSGGG-STYYPDTVKG (SEQ ID NO 2) | EALYDYDYAMDY (SEQ ID NO 3) |
| hz39D2 | NYGVN (SEQ ID NO 7) | WINTHTGEPTY-AEEFKG (SEQ ID NO 8) | DDYYVRVDY (SEQ ID NO 9) |
| 24D3 | SCAMS (SEQ ID NO 13) | TISGGG-SYTYYPDSVKG (SEQ ID NO 14) | HGGYESWFPY (SEQ ID NO 15) |
| 1G3 | DTYMH (SEQ ID NO 19) | RID-PANGYTRYDPNFQG (SEQ ID NO 20) | YYYGFYAMDY (SEQ ID NO 21) |
| hz8G11 | GYYMH (SEQ ID NO 25) | HINPNNGGTSYN-QKFKG (SEQ ID NO 26) | EEAFAY (SEQ ID NO 27) |

TABLE 5

| Clones | CDRL1 | CDRL2 | CDRL3 |
|---|---|---|---|
| hz2G10 | KSSQSLLYSNGKTYLN (SEQ ID NO 4) | LVSKLDS (SEQ ID NO 5) | VQGTHFPLT (SEQ ID NO 6) |
| hz39D2 | KASQDINSYLS (SEQ ID NO 10) | RANRLVD (SEQ ID NO 11) | LQYDEFPWT (SEQ ID NO 12) |
| 24D3 | RSSQSLVHSNGNTYLH (SEQ ID NO 16) | KVSNRFS (SEQ ID NO 17) | SQSTHVPPWT (SEQ ID NO 18) |
| 1G3 | KASQDVSTAVA (SEQ ID NO 22) | SASYRYT (SEQ ID NO 23) | QQHYSTPPT (SEQ ID NO 24) |
| hz8G11 | RASQDISNYLN (SEQ ID NO 28) | YTSRLHS (SEQ ID NO 29) | QQGITPPWT (SEQ ID NO 30) |

Tables 4 and 5 show the amino acid sequences of the heavy chain CDR (CDRH) and the light chain CDR (CDRL) of the developed antibodies.

Example 5: Specificity of Developed Antibody for HER2

It was investigated whether the developed five antibodies of the present disclosure specifically bind to HER2 belonging to the ErbB family proteins by ELISA. In order to confirm whether the developed antibody binds specifically to HER2 belonging to the ErbB family proteins, the extracellular domains of EGFR, HER2, HER3 and HER4 belonging to the ErbB family were examined via ELISA. The extracellular domain of EGFR (EGFR-ECD-Fc) was produced in the same manner as the HER2-ECD-Fc described above in Example 2, and the HER3 (R&D Systems, #348-RB-050) and HER4 (R&D Systems, #1131-ER-050) proteins were purchased. Cetuximab (CET), trastuzumab (TRA) and patritumab (AMG888, AMG) were used as control group antibodies binding to EGFR, HER2 and HER3, respectively.

Figure 4:
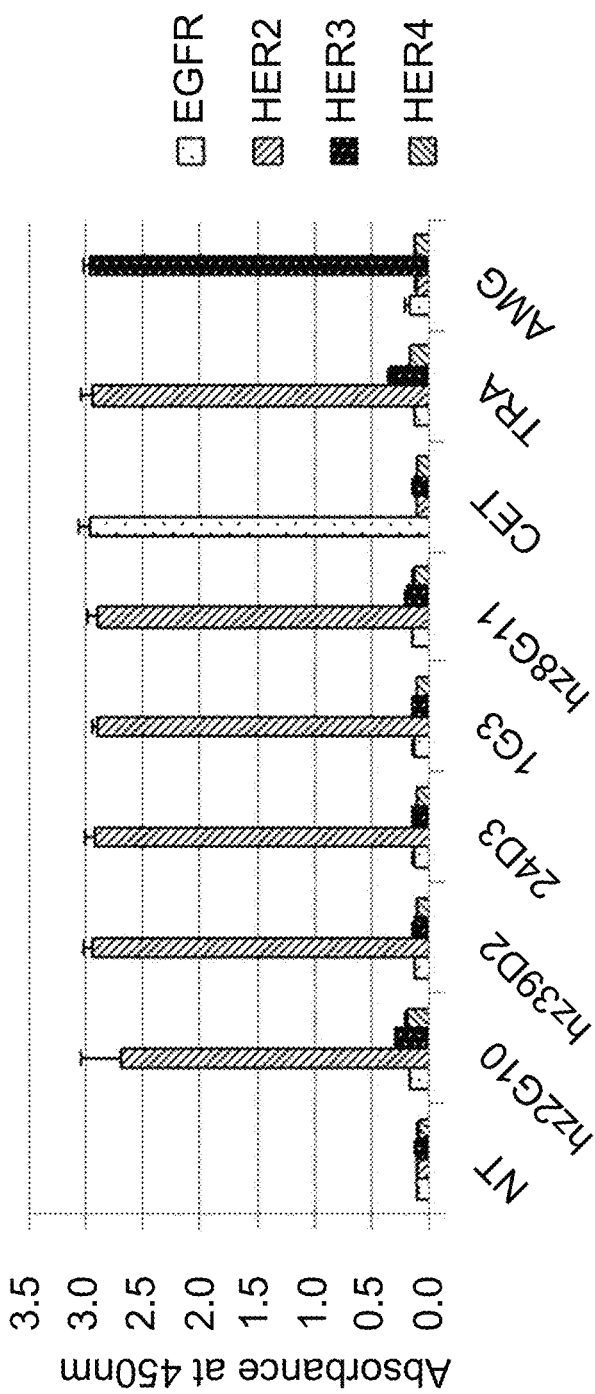
FIG. 4 shows a result of investigating the specificity of antibodies developed by expressing the ErbB family. Cetuximab (CET), trastuzumab (TRA) and patritumab (AMG888, AMG) were used as control groups binding to EGFR, HER2 and HER3, respectively.
Figure 5A:
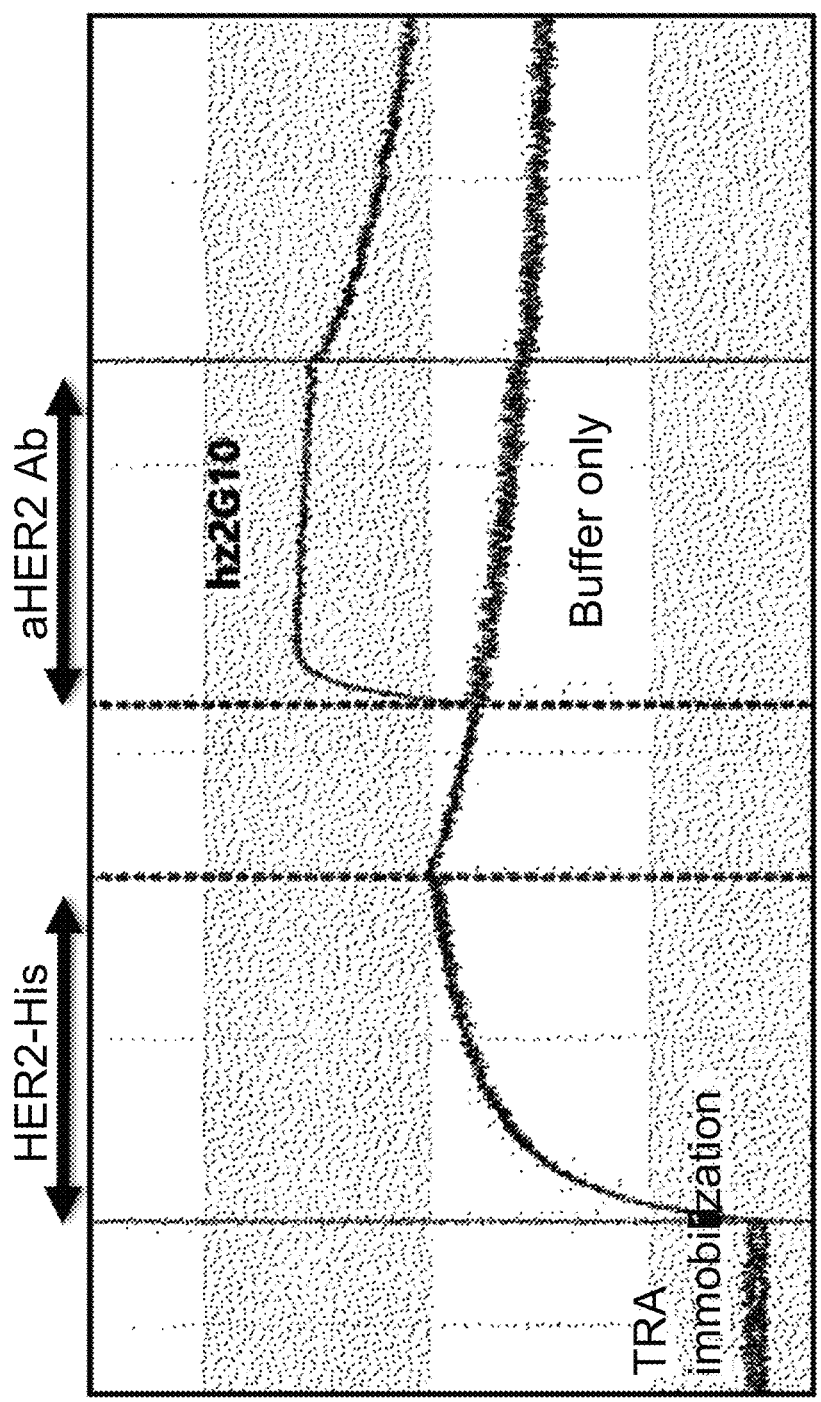
FIGS. 5a-5e show a result of comparing the epitopes of developed antibodies with trastuzumab. For comparison with the epitope of trastuzumab, trastuzumab and HER2-His were immobilized on a sensor chip and then the binding with five antibodies of the present disclosure was analyzed.
Figure 5B:
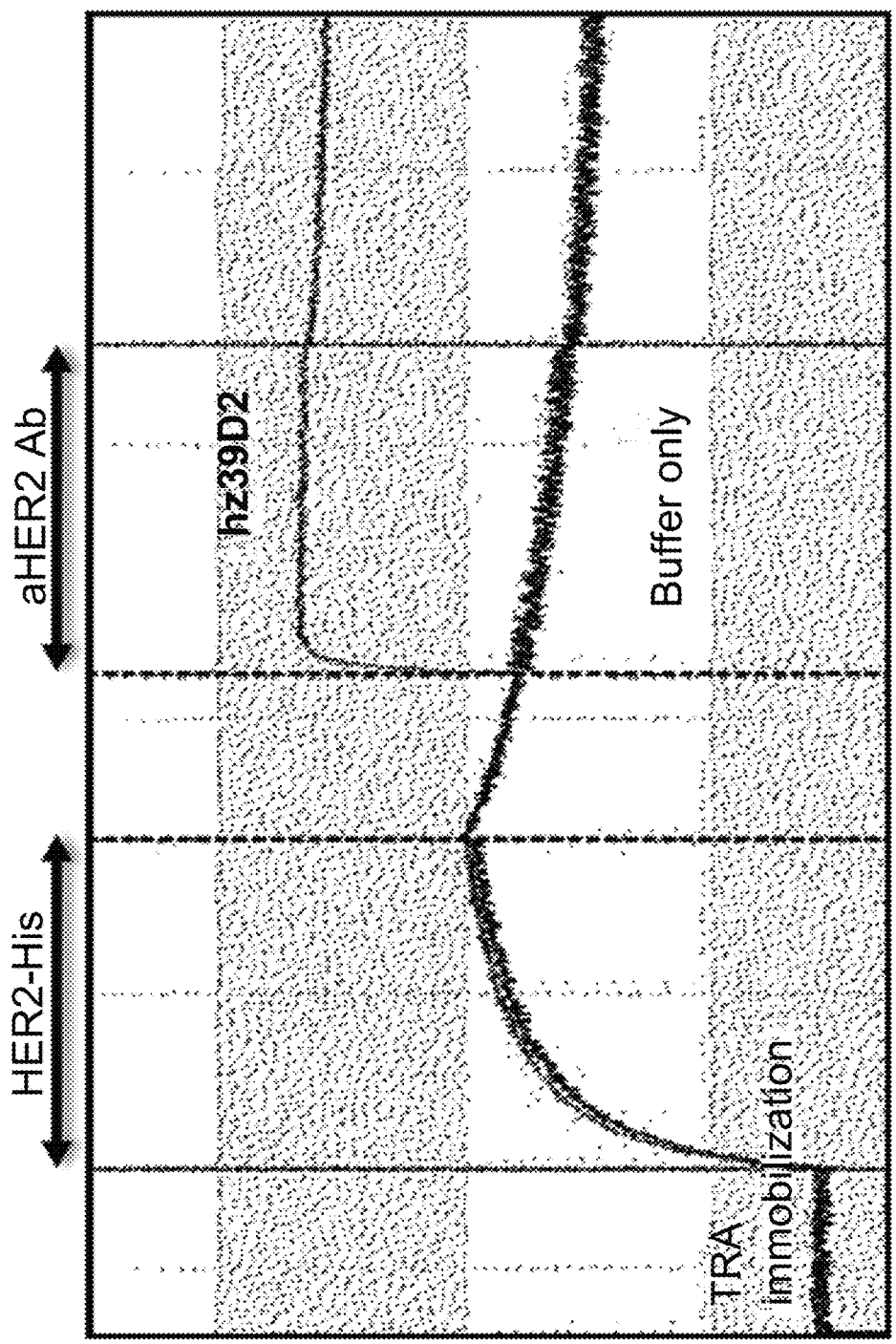
Figure 5C:
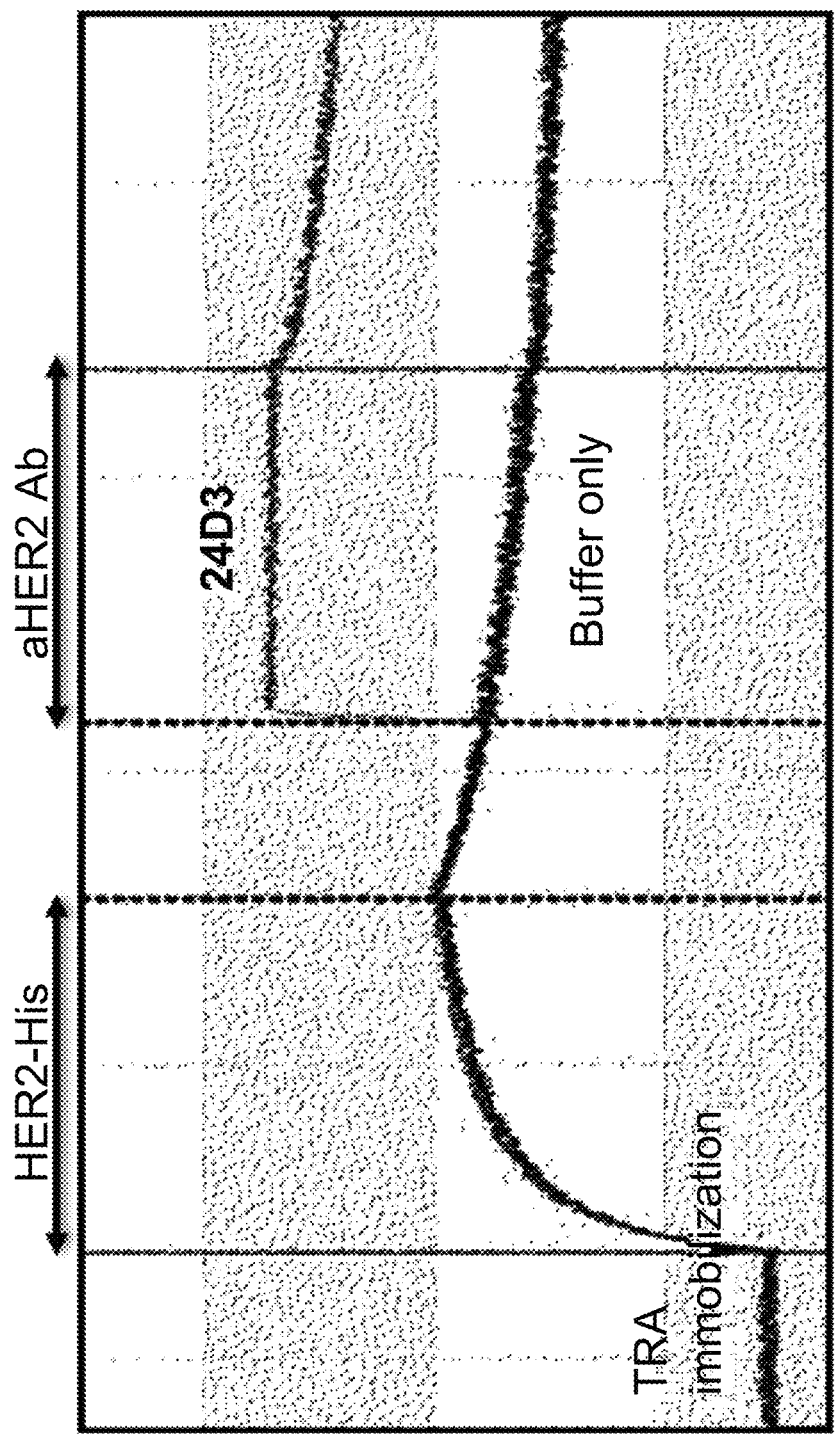
Figure 5D:
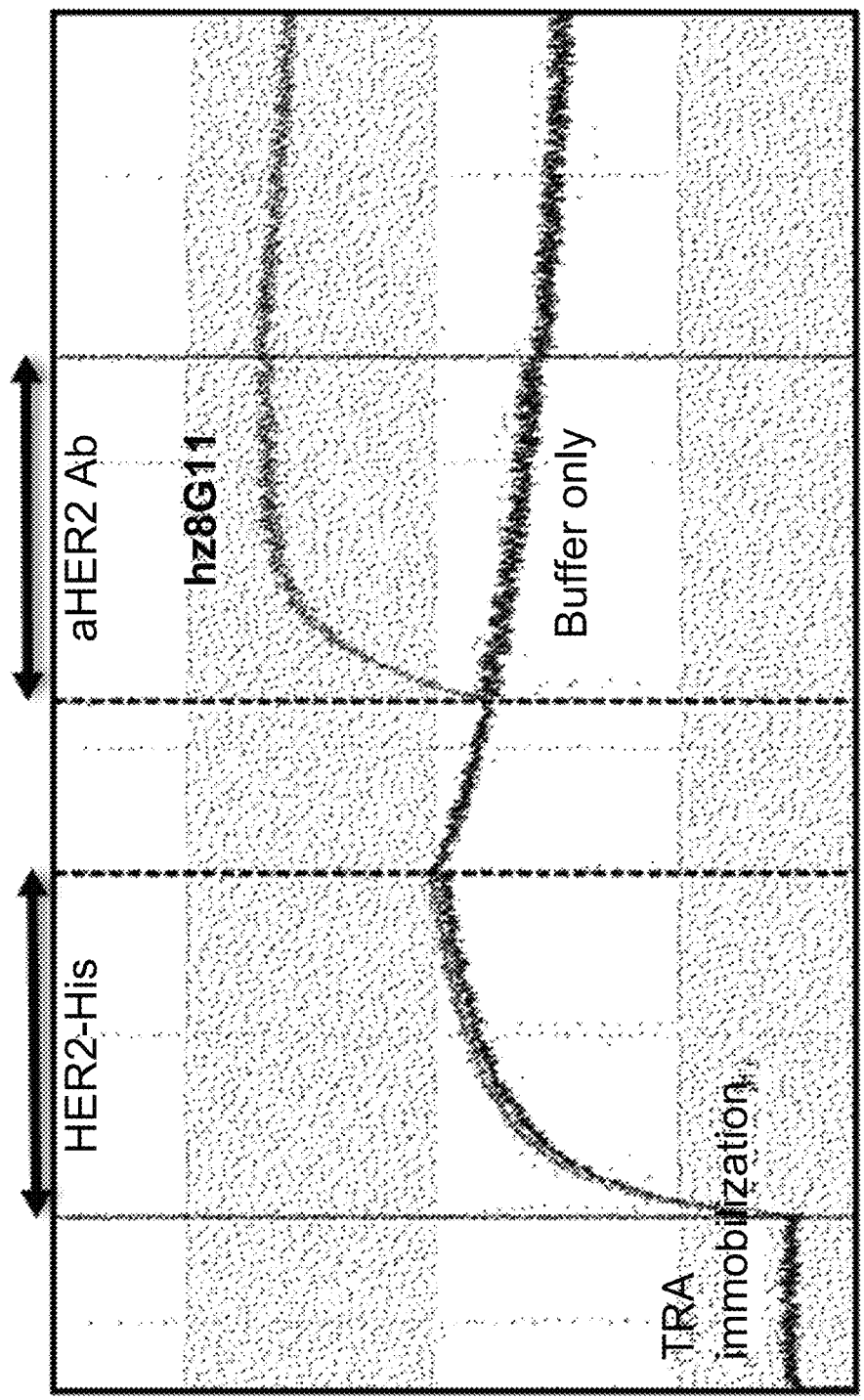
Figure 5E:
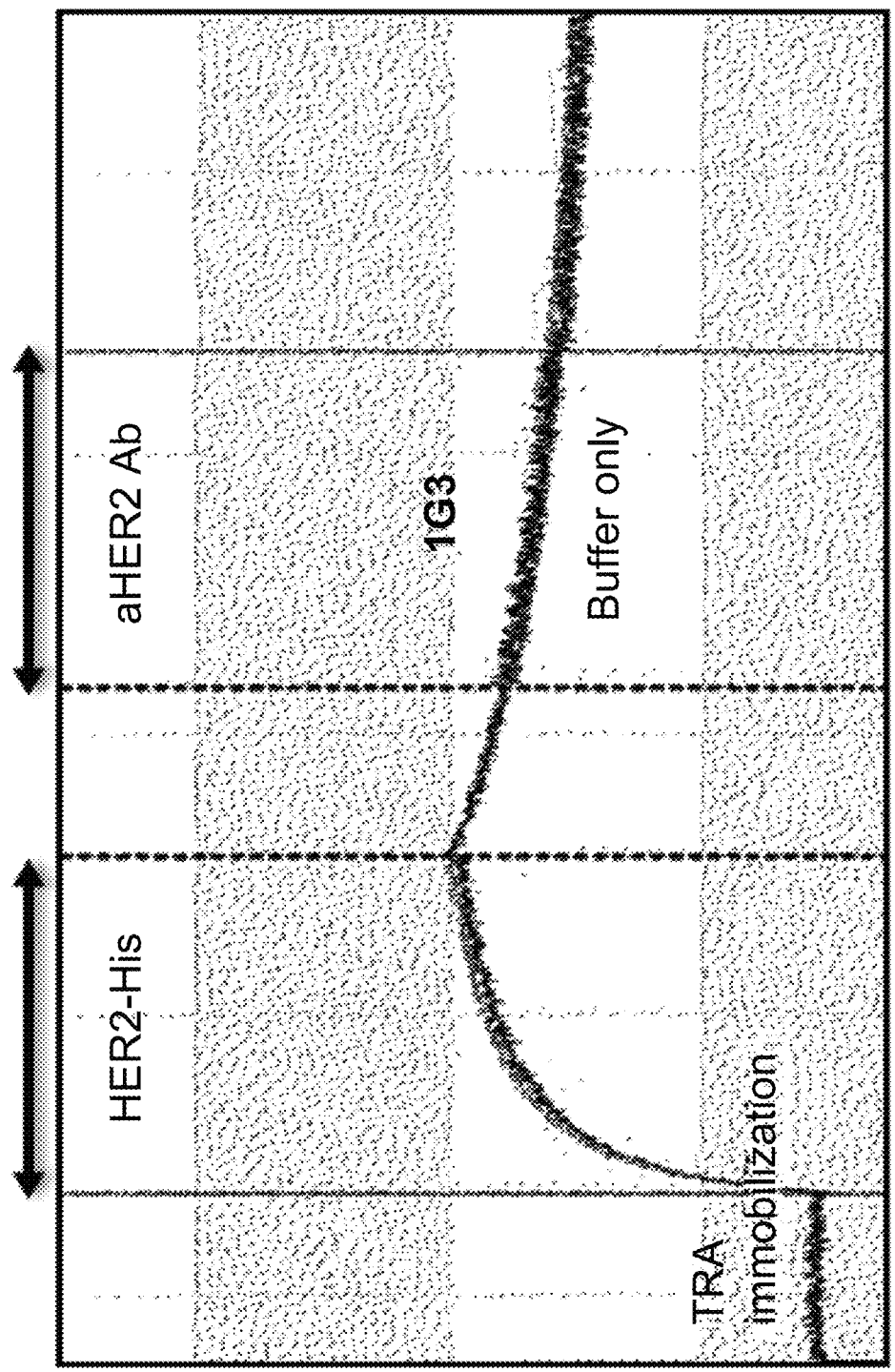

The result is shown in FIG. 4.

As seen from FIG. 4, it was confirmed that the five antibodies of the present disclosure bind specifically to HER2 among the human ErbB family proteins.

Example 6: Comparison of Epitopes of Developed Antibody and Trastuzumab

It is known that the anti-HER2 antibody trastuzumab binds to the domain 4 among the four domains of HER2 ECD. In order to investigate whether the developed antibodies and trastuzumab share the epitope for HER2, epitope binning was conducted using Octet (Pall ForteBio). Trastuzumab was immobilized onto an AR2G sensor chip (ForteBio, Cat. Nos. 18-5092 (tray), 18-5093 (pack), 18-5094 (case)) at a concentration of 10 µg/mL by amine coupling using ECD/NHS. After allowing the HER2-ECD-His protein to bind to the trastuzumab-immobilized sensor chip at a concentration of 10 µg/mL for 10 minutes, the binding between trastuzumab and HER2-ECD was stabilized for 5 minutes. Then, the five antibodies of the present disclosure were bound at a concentration of 10 µg/mL for 10 minutes and the binding between the antigen and the antibodies was stabilized for 10 minutes. After the immobilization of trastuzumab, all the antibodies and antigen were diluted using a kinetics buffer (ForteBio, Cat No. 18-1092). The same buffer was used during the stabilization. If the additionally added antibody binds to the trastuzumab-bound HER2-ECD protein, it can be interpreted that the antibody does not share the epitope with trastuzumab.

The result is shown in FIGS. 5a-5e.

As seen from FIGS. 5a-5e, it was confirmed that the developed antibodies hz2G10, hz39D2, 24D3 and hz8G11 had different epitopes from that of trastuzumab because they were bound to the trastuzumab-bound HER2-ECD. In contrast, 1G3 did not bind to the trastuzumab-bound HER2-ECD, suggesting that it shares the epitope with trastuzumab.

Example 7: Development of hz39D2 Antibody with Increased Affinity

In order to develop antibodies with improved affinity based on the humanized 39D2 antibody (hz39D2), the inventors of the present disclosure have developed a phage antibody library with CDR3 of the light chain or heavy chain randomized (Phage display: a laboratory manual, Carlos Barbas III, et al., Cold Spring Harbor Laboratory Press). D and Y corresponding to D101 and Y102 of the CDR3 of the heavy chain according to Kabat numbering and P, W and T corresponding to P95, W96, T97 of the CDR3 of the light chain according to Kabat numbering were excluded from the randomization because they are commonly observed amino acids in human antibodies. Primers were synthesized such that adenine (A), cytosine (C), guanine (G) and thymine (T) were inserted randomly into the first and second positions of the codon corresponding to the amino acid to be randomized, with the same ratio, and guanine (G) or cytosine (C) was inserted into the third position at the same ratio. From the developed library, the clones with improved affinity were selected through biopanning using the HER2-ECD-His protein. The CDR sequence data of the finally selected three antibodies, hz39D2.14, hz39D2.22 and hz39D2.23, are summarized in Table 6 and Table 7. The amino acid residues modified to improve affinity are underlined.

TABLE 6

| Clones | CDRH1 | CDRH2 | CDRH3 |
|---|---|---|---|
| hz39D2 | NYGVN (SEQ ID NO 7) | WINTHTGEPTYAEEFKG (SEQ ID NO 8) | DDYYVRVDY (SEQ ID NO 9) |
| hz39D2.14 | NYGVN (SEQ ID NO 7) | WINTHTGEPTYAEEFKG (SEQ ID NO 8) | DEYYVRTDY (SEQ ID NO 71) |
| hz39D2.22 | NYGVN (SEQ ID NO 7) | WINTHTGEPTYAEEFKG (SEQ ID NO 8) | DEYYVRVDY (SEQ ID NO 72) |
| hz39D2.23 | NYGVN (SEQ ID NO 7) | WINTHTGEPTYAEEFKG (SEQ ID NO 8) | DEYYVRVDY (SEQ ID NO 73) |

TABLE 7

| Clones | CDRL1 | CDRL2 | CDRL3 |
|---|---|---|---|
| hz39D2 | KASQDINSYLS (SEQ ID NO 10) | RANRLVD (SEQ ID NO 11) | LQYDEFPWT (SEQ ID NO 12) |
| hz39D2.14 | KASQDINSYLS (SEQ ID NO 10) | RANRLVD (SEQ ID NO 11) | LQYDEFPWT (SEQ ID NO 12) |
| hz39D2.22 | KASQDINSYLS (SEQ ID NO 10) | RANRLVD (SEQ ID NO 11) | LELDEFPWT (SEQ ID NO 73) |
| hz39D2.23 | KASQDINSYLS (SEQ ID NO 10) | RANRLVD (SEQ ID NO 11) | LQLDEFPWT (SEQ ID NO 74) |

IgG antibodies were produced to verify the increased affinity of the three selected antibodies (hz39D2.14, hz39D2.22 and hz39D2.23). 2000 RU of goat anti-human IgG (Invitrogen, #H10500) was immobilized onto a CM5 sensor chip by ECD/NHS. Then, the antibodies were allowed to bind at a rate of 50 μL/min for 5 minutes and then stabilized for 5 minutes by flowing a buffer. After stabilizing the antibodies, the HER2-ECD-His protein was allowed to bind at a rate of 50 μL/min for 4 minutes and then separated by flowing a buffer for 15 minutes. After analyzing the concentration, the resultant was recycled using 10 mM glycine (pH 1.5) and then subjected to the subsequent assay. The affinity of the antibodies was analyzed using the BIAevaluation software. The analysis result is summarized in Table 8. As seen from Table 8, all of the three selected antibodies (hz39D2.14, hz39D2.22 and hz39D2.23) showed improved affinity as compared to hz39D2.

TABLE 8

| Clones | $K_a$ (1/Ms) | $K_d$ (1/s) | $K_D$ (M) |
|---|---|---|---|
| hz39D2 | 6.8E+04 | 2.5E−03 | 3.7E−08 |
| hz39D2.14 | 3.7E+04 | 3.0E−04 | 8.0E−09 |
| hz39D2.22 | 8.1E+04 | 1.6E−04 | 2.0E−09 |
| hz39D2.23 | 7.1E+04 | 2.0E−04 | 2.8E−09 |

Figure 6A:
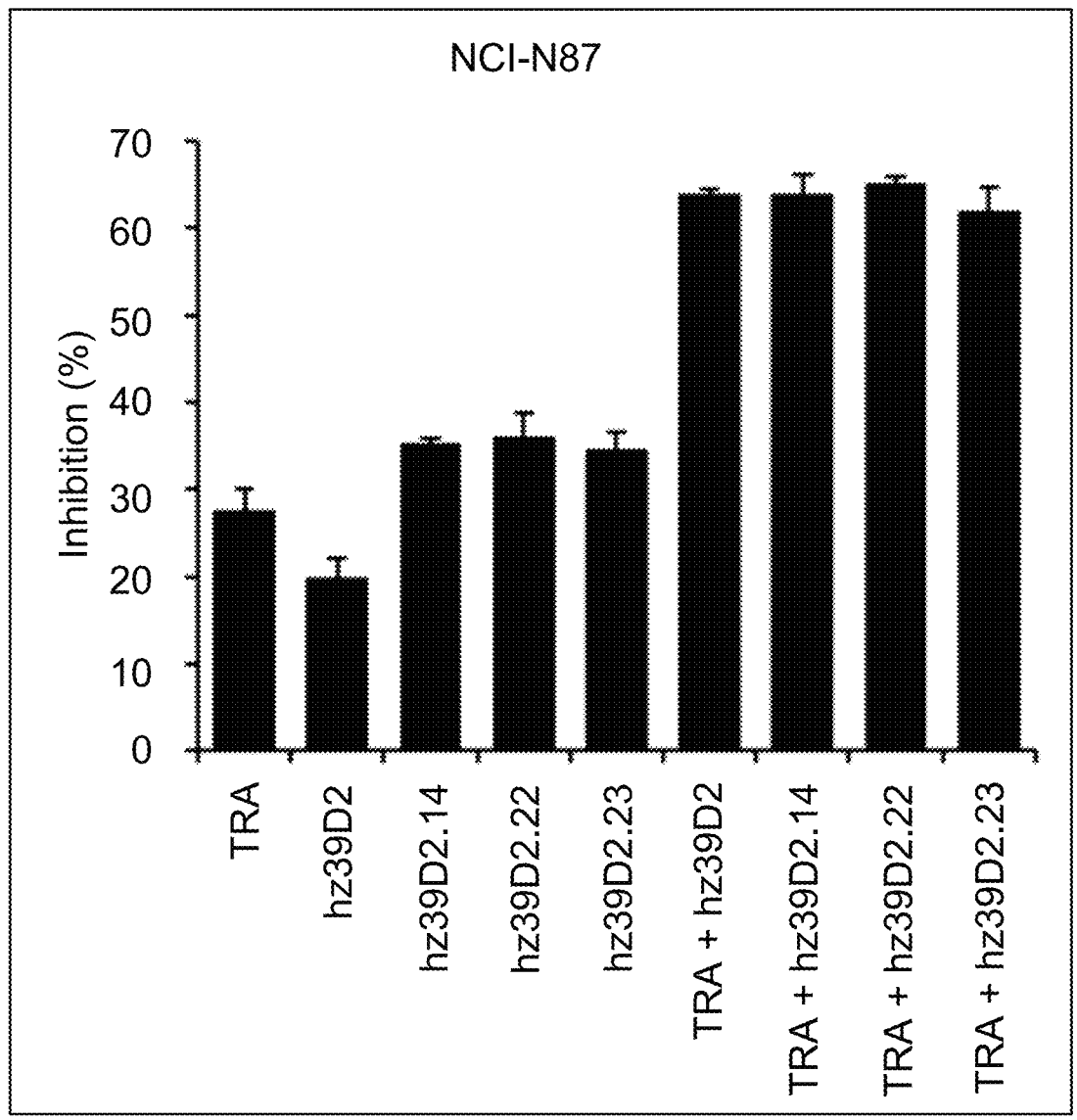
FIGS. 6a-6c show a result of analyzing the effect of single administration of hz39D2 and affinity-improved clones thereof (hz39D2.14, hz39D2.22 and hz39D2.23) or co-administration with the trastuzumab antibody on the inhibition of the growth of HER2-overexpressed gastric cancer and breast cancer cells.
Figure 6B:
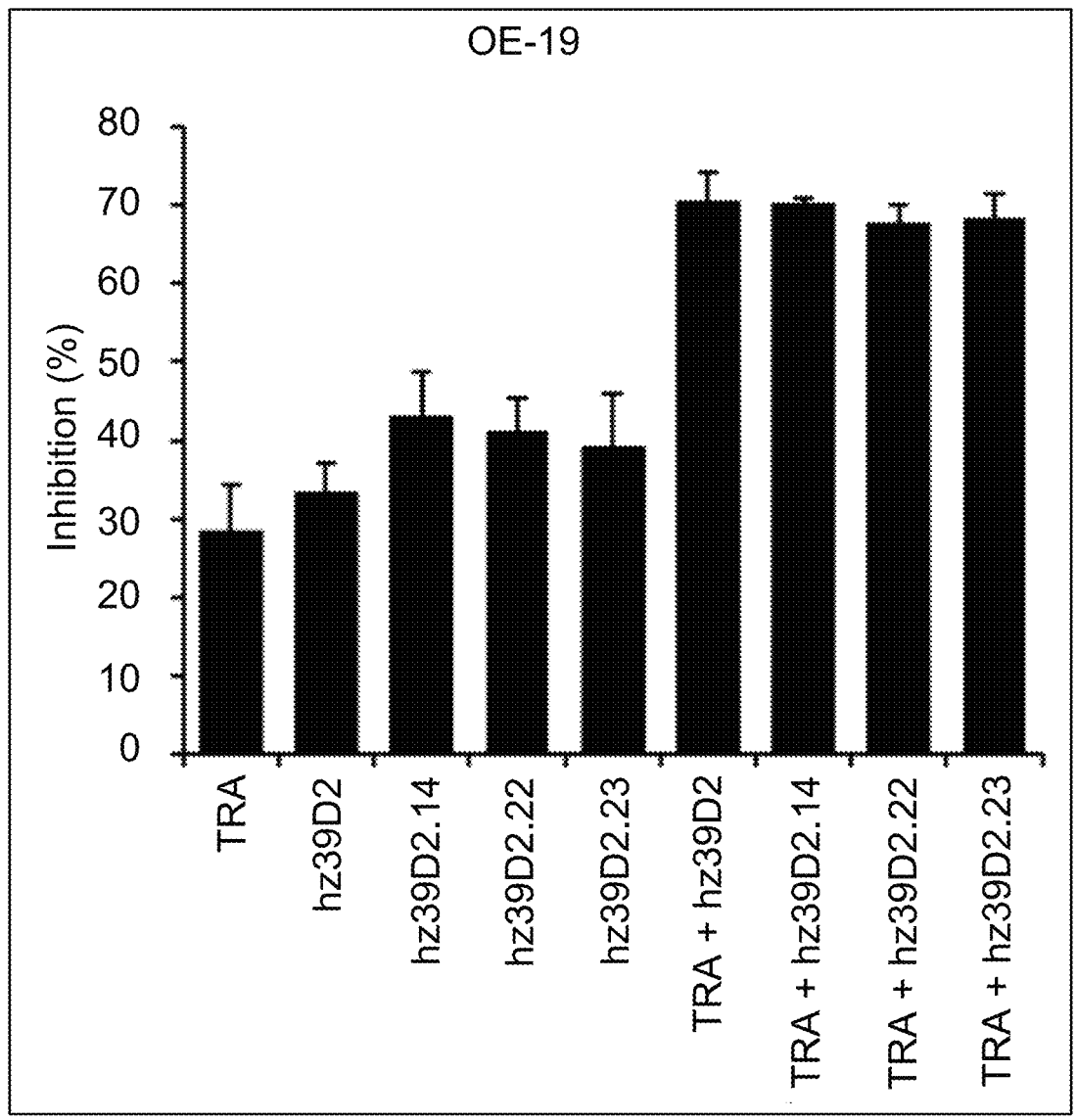
Figure 6C:
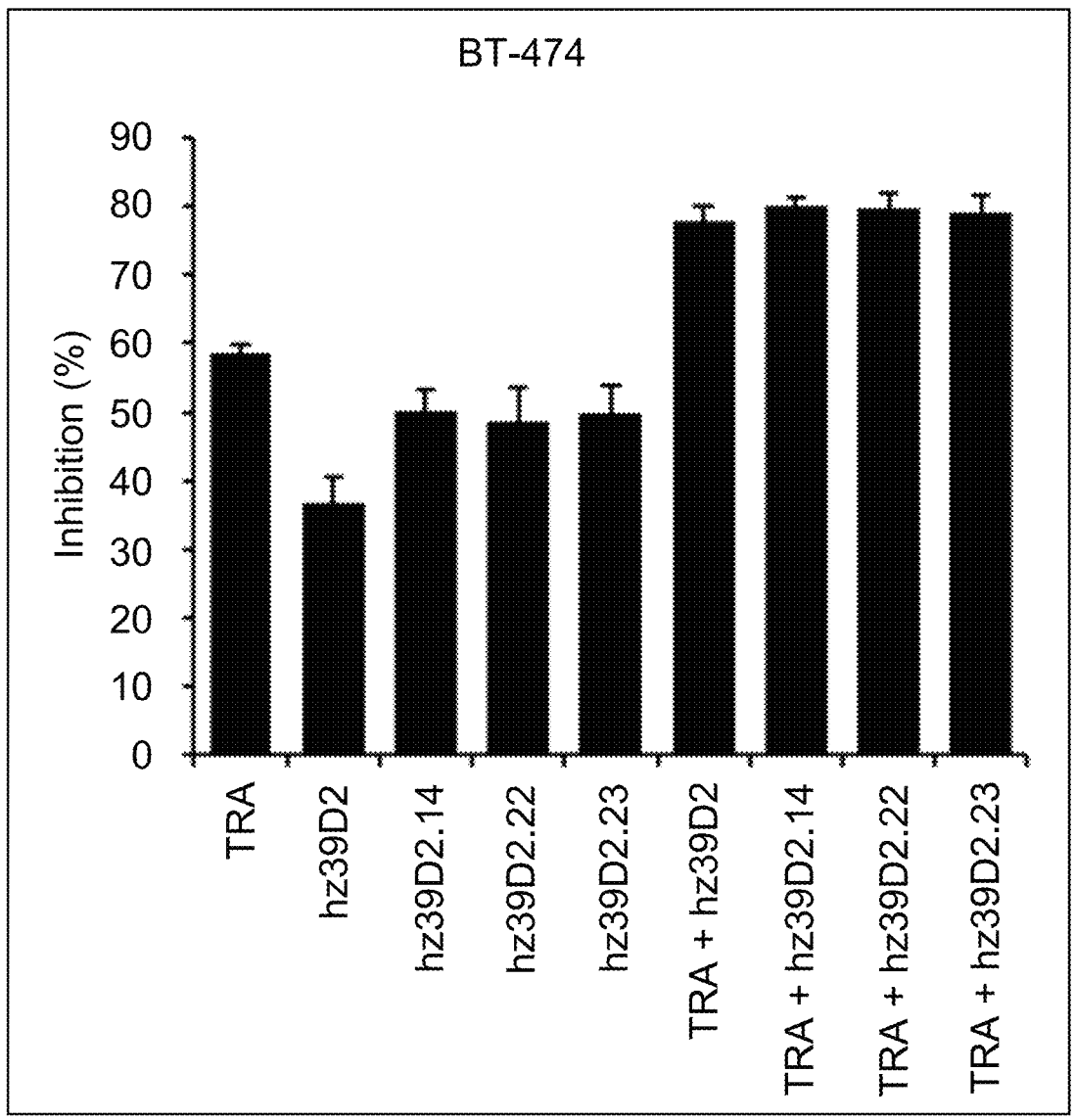

The anticancer effect of the three antibodies (hz39D2.14, hz39D2.22 and hz39D2.23) with improved affinity was analyzed using HER2-overexpressed NCI-N87 and OE-19 gastric cancer cells and BT-474 breast cancer cells. After treating the cells with each antibody at a concentration of 5 μg/mL either alone or in combination with trastuzumab, the viability of the cancer cells was analyzed (FIGS. 6a-6c). As seen from FIGS. 6a-6c, it was confirmed that the hz39D2.14, hz39D2.22, and hz39D2.23 antibodies with improved affinity showed improved effect of inhibiting cancer cell proliferation when treated alone.

What is claimed is:

1. An antibody against human epidermal growth factor receptor 2 (HER2), or an antigen-binding fragment thereof, comprising:
   (a) a heavy chain variable region comprising CDRH1 of SEQ ID NO: 7, CDRH2 of SEQ ID NO: 8 and CDRH3 of SEQ ID NO: 9, and a light chain variable region comprising CDRL1 of SEQ ID NO: 10, CDRL2 of SEQ ID NO: 11 and CDRL3 of SEQ ID NO: 12;
   (b) a heavy chain variable region comprising CDRH1 of SEQ ID NO: 7, CDRH2 of SEQ ID NO: 8 and CDRH3 of SEQ ID NO: 71, and a light chain variable region comprising CDRL1 of SEQ ID NO: 10, CDRL2 of SEQ ID NO: 11 and CDRL3 of SEQ ID NO: 12;
   (c) a heavy chain variable region comprising CDRH1 of SEQ ID NO: 7, CDRH2 of SEQ ID NO: 8 and CDRH3 of SEQ ID NO: 72, and a light chain variable region comprising CDRL1 of SEQ ID NO: 10, CDRL2 of SEQ ID NO: 11 and CDRL3 of SEQ ID NO: 73; or
   (d) a heavy chain variable region comprising CDRH1 of SEQ ID NO: 7, CDRH2 of SEQ ID NO: 8 and CDRH3 of SEQ ID NO: 72, and a light chain variable region comprising CDRL1 of SEQ ID NO: 10, CDRL2 of SEQ ID NO: 11 and CDRL3 of SEQ ID NO: 74.

2. The antibody or the antigen-binding fragment thereof according to claim 1, wherein:
   the heavy chain variable region of (a) comprises amino acid sequence of SEQ ID NO: 39;
   the heavy chain variable region of (b) comprises amino acid sequence of SEQ ID NO: 87;
   the heavy chain variable region of (c) comprises amino acid sequence of SEQ ID NO: 95; and
   the heavy chain variable region of (d) comprises amino acid sequence of SEQ ID NO: 103.

3. The antibody or the antigen-binding fragment thereof according to claim 1, wherein:
   the light chain variable region of (a) comprises amino acid sequence of SEQ ID NO: 43;
   the light chain variable region of (b) comprises amino acid sequence of SEQ ID NO: 91;
   the light chain variable region of (c) comprises amino acid sequence of SEQ ID NO: 99; and
   the light chain variable region of (d) comprises amino acid sequence of SEQ ID NO: 107.

4. The antibody or the antigen-binding fragment thereof according to claim 1, wherein
   the antibody or the antigen-binding fragment thereof comprising (a) comprises a heavy chain comprising the amino acid sequence of SEQ ID NO: 41;
   the antibody or the antigen-binding fragment thereof comprising (b) comprises a heavy chain comprising the amino acid sequence of SEQ ID NO: 89;
   the antibody or the antigen-binding fragment thereof comprising (c) comprises a heavy chain comprising the amino acid sequence of SEQ ID NO: 97; and
   the antibody or the antigen-binding fragment thereof comprising (d) comprises a heavy chain comprising the amino acid sequence of SEQ ID NO: 105.

5. The antibody or the antigen-binding fragment thereof according to claim 1, wherein
   the antibody or the antigen-binding fragment thereof comprising (a) comprises a light chain comprising the amino acid sequence of SEQ ID NO: 45;
   the antibody or the antigen-binding fragment thereof comprising (b) comprises a light chain comprising the amino acid sequence of SEQ ID NO: 93;
   the antibody or the antigen-binding fragment thereof comprising (c) comprises a light chain comprising an amino acid sequence of SEQ ID NO: 101; and
   the antibody or the antigen-binding fragment thereof comprising (d) comprises a light chain comprising the amino acid sequence of SEQ ID NO: 109.

6. The antibody or antigen-binding fragment thereof according to claim 1, wherein the antibody or antigen-binding fragment thereof comprises a heavy chain variable region comprising CDRH1 of SEQ ID NO: 7, CDRH2 of SEQ ID NO: 8, and CDRH3 of SEQ ID NO: 9, and a light chain variable region comprising CDRL1 of SEQ ID NO: 10, CDRL2 of SEQ ID NO: 11, and CDRL3 of SEQ ID NO: 12.

7. The antibody or antigen-binding fragment thereof according to claim 1, wherein the heavy chain variable region comprises an amino acid sequence of SEQ ID NO: 39 and the light chain variable region comprises an amino acid sequence of SEQ ID NO: 43.

8. The antibody or antigen-binding fragment thereof according to claim 1, wherein the heavy chain comprises an amino acid sequence of SEQ ID NO: 41 and the light chain comprises the amino acid sequence of SEQ ID NO: 45.

9. A fusion protein comprising the antibody or antigen-binding fragment thereof according to claim 1.

10. A fusion protein comprising the antibody or antigen-binding fragment thereof according to claim 6.

11. A chimeric antigen receptor polypeptide comprising:
    (a) an HER2-binding domain comprising the antibody or antigen-binding fragment thereof according to claim 1;
    (b) a transmembrane domain (TM);
    (c) a costimulatory domain; and
    (d) an intracellular signaling domain (ICD).

12. A chimeric antigen receptor polypeptide comprising:
    (a) an HER2-binding domain comprising the antibody or antigen-binding fragment thereof according to claim 6;
    (b) a transmembrane domain (TM);
    (c) a costimulatory domain; and
    (d) an intracellular signaling domain (ICD).

13. The chimeric antigen receptor polypeptide according to claim 12, wherein the transmembrane domain is a transmembrane domain of a protein selected from a group consisting of T-cell receptor alpha, beta or zeta chain, CD28, CD3 epsilon, CD45, CD4, CDS, CD8, CD9, CD16, CD22, CD33, CD37, CD64, CD80, CD86, CD134, CD137 and CD154.

14. The chimeric antigen receptor polypeptide according to claim 12, wherein the costimulatory domain is a functional signaling domain obtained from a protein selected from a group consisting of MHC class I molecule, TNF receptor protein, immunoglobulin-like protein, cytokine receptor, integrin, signaling lymphocytic activation molecule (SLAM), activating NK cell receptor, BTLA (B- and T-lymphocyte attenuator), Toll-like ligand receptor, OX40, CD2, CD7, CD27, CD28, CD30, CD40, CDS, ICAM-1, LFA-1 (CD1 1a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11e, ITGB1, CD29, ITGB2, CD18, LFA-1, ITGB7, NKG2D, NKG2C, TNFR2, TRANCE/RANKL, DNAMI (CD226), SLAMF4 (CD244, 2B4), CD84, CD96 (Tactile), CEACAM1, CRTAM, Ly9 (CD229), CD160 (BY55), PSGLI, CD100 (SEMA4D), CD69, SLAMF6 (NTB-A, Ly108), SLAM (SLAMF1, CD150, IPO-3), BLAME (SLAMF8), SELPLG(CD162), LTBR, LAT, GADS, SLP-76, PAG/Cbp, CD19a, and a ligand binding specifically to CD83.

15. The chimeric antigen receptor polypeptide according to claim 12, wherein the intracellular signaling domain comprises a functional signaling domain of 4-1BB, CD28, OX40 or CD3 zeta, or a combination thereof.

16. A nucleic acid molecule encoding the anti-HER2 antibody or the antigen-binding fragment thereof according to claim 6.

17. A nucleic acid molecule encoding the chimeric antigen receptor polypeptide according to claim 12.

18. A recombinant vector comprising the nucleic acid molecule according to claim 17.

19. A host cell transformed with the recombinant vector according to claim 18.

20. An effector cell expressing the chimeric antigen receptor polypeptide according to claim 12.

21. The effector cell according to claim 20, wherein the effector cell is selected from a group consisting of a dendritic cell, a killer dendritic cell, a mast cell, a natural killer cell, a B lymphocyte, a T lymphocyte, a macrophage and precursor cells thereof.

22. A pharmaceutical composition for treating cancer, comprising: (a) a pharmaceutically effective amount of the anti-HER2 antibody or the antigen-binding fragment thereof according to claim 6; and (b) a pharmaceutically acceptable carrier.

23. A pharmaceutical composition for treating cancer, comprising the effector cell expressing the chimeric antigen receptor polypeptide according to claim 20.

24. A kit for diagnosing cancer, comprising the anti-HER2 antibody or the antigen-binding fragment thereof according to claim 6.

* * * * *

SEQUENCE LISTING

<160> NUMBER OF SEQ ID NOS: 110

<210> SEQ ID NO 1
<211> LENGTH: 5
<212> TYPE: PRT
<213> ORGANISM: Artificial Sequence
<220> FEATURE:
<223> OTHER INFORMATION: CDRH1 of hz2G10 antibody

<400> SEQUENCE: 1

Asp Tyr Tyr Met Tyr
1               5

<210> SEQ ID NO 2
<211> LENGTH: 17

```
<212> TYPE: PRT
<213> ORGANISM: Artificial Sequence
<220> FEATURE:
<223> OTHER INFORMATION: CDRH2 of hz2G10 antibody

<400> SEQUENCE: 2

Tyr Ile Asn Ser Gly Gly Gly Ser Thr Tyr Tyr Pro Asp Thr Val Lys
1               5                   10                  15
Gly

<210> SEQ ID NO 3
<211> LENGTH: 12
<212> TYPE: PRT
<213> ORGANISM: Artificial Sequence
<220> FEATURE:
<223> OTHER INFORMATION: CDRH3 of hz2G10 antibody

<400> SEQUENCE: 3

Glu Ala Leu Tyr Asp Tyr Asp Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: CDRL1 of hz2G10 antibody

<400> SEQUENCE: 4

Lys Ser Ser Gln Ser Leu Leu Tyr Ser Asn Gly Lys Thr Tyr Leu Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDRL2 of hz2G10 antibody

<400> SEQUENCE: 5

Leu Val Ser Lys Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3 of hz2G10 antibody

<400> SEQUENCE: 6

Val Gln Gly Thr His Phe Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: CDRH1 of hz39D2 antibody

<400> SEQUENCE: 7

Asn Tyr Gly Val Asn
1               5

<210> SEQ ID NO 8
```

```
<211> LENGTH: 17
<212> TYPE: PRT
<213> ORGANISM: Artificial Sequence
<220> FEATURE:
<223> OTHER INFORMATION: CDRH2 of hz39D2 antibody

<400> SEQUENCE: 8

Trp Ile Asn Thr His Thr Gly Glu Pro Thr Tyr Ala Glu Glu Phe Lys
1               5                   10                  15
Gly

<210> SEQ ID NO 9
<211> LENGTH: 9
<212> TYPE: PRT
<213> ORGANISM: Artificial Sequence
<220> FEATURE:
<223> OTHER INFORMATION: CDRH3 of hz39D2 antibody

<400> SEQUENCE: 9

Asp Asp Tyr Tyr Val Arg Val Asp Tyr
1               5

<210> SEQ ID NO 10
<211> LENGTH: 11
<212> TYPE: PRT
<213> ORGANISM: Artificial Sequence
<220> FEATURE:
<223> OTHER INFORMATION: CDRL1 of hz39D2 antibody

<400> SEQUENCE: 10

Lys Ala Ser Gln Asp Ile Asn Ser Tyr Leu Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CDRL2 of hz39D2 antibody

<400> SEQUENCE: 11

Arg Ala Asn Arg Leu Val Asp
1               5

<210> SEQ ID NO 12
<211> LENGTH: 9
<212> TYPE: PRT
<213> ORGANISM: Artificial Sequence
<220> FEATURE:
<223> OTHER INFORMATION: CDRL3 of hz39D2 antibody

<400> SEQUENCE: 12

Leu Gln Tyr Asp Glu Phe Pro Trp Thr
1               5

<210> SEQ ID NO 13
<211> LENGTH: 5
<212> TYPE: PRT
<213> ORGANISM: Artificial Sequence
<220> FEATURE:
<223> OTHER INFORMATION: CDRH1 of 24D3 antibody

<400> SEQUENCE: 13

Ser Cys Ala Met Ser
1               5
```

```
<210> SEQ ID NO 14
<211> LENGTH: 17
<212> TYPE: PRT
<213> ORGANISM: Artificial Sequence
<220> FEATURE:
<223> OTHER INFORMATION: CDRH2 of 24D3 antibody

<400> SEQUENCE: 14

Thr Ile Ser Gly Gly Gly Ser Tyr Thr Tyr Tyr Pro Asp Ser Val Lys
1               5                   10                  15

Gly

<210> SEQ ID NO 15
<211> LENGTH: 10
<212> TYPE: PRT
<213> ORGANISM: Artificial Sequence
<220> FEATURE:
<223> OTHER INFORMATION: CDRH3 of 24D3 antibody

<400> SEQUENCE: 15

His Gly Gly Tyr Glu Ser Trp Phe Pro Tyr
1               5                   10

<210> SEQ ID NO 16
<211> LENGTH: 16
<212> TYPE: PRT
<213> ORGANISM: Artificial Sequence
<220> FEATURE:
<223> OTHER INFORMATION: CDRL1 of 24D3 antibody

<400> SEQUENCE: 16

Arg Ser Ser Gln Ser Leu Val His Ser Asn Gly Asn Thr Tyr Leu His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: CDRL2 of 24D3 antibody

<400> SEQUENCE: 17

Lys Val Ser Asn Arg Phe Ser
1               5

<210> SEQ ID NO 18
<211> LENGTH: 10
<212> TYPE: PRT
<213> ORGANISM: Artificial Sequence
<220> FEATURE:
<223> OTHER INFORMATION: CDRL3 of 24D3 antibody

<400> SEQUENCE: 18

Ser Gln Ser Thr His Val Pro Pro Trp Thr
1               5                   10

<210> SEQ ID NO 19
<211> LENGTH: 5
<212> TYPE: PRT
<213> ORGANISM: Artificial Sequence
<220> FEATURE:
<223> OTHER INFORMATION: CDRH1 of 1G3 antibody

<400> SEQUENCE: 19

Asp Thr Tyr Met His
1               5
```

```
<210> SEQ ID NO 20
<211> LENGTH: 17
<212> TYPE: PRT
<213> ORGANISM: Artificial Sequence
<220> FEATURE:
<223> OTHER INFORMATION: CDRH2 of 1G3 antibody

<400> SEQUENCE: 20

Arg Ile Asp Pro Ala Asn Gly Tyr Thr Arg Tyr Asp Pro Asn Phe Gln
1               5                   10                  15

Gly

<210> SEQ ID NO 21
<211> LENGTH: 10
<212> TYPE: PRT
<213> ORGANISM: Artificial Sequence
<220> FEATURE:
<223> OTHER INFORMATION: CDRH3 of 1G3 antibody

<400> SEQUENCE: 21

Tyr Tyr Tyr Gly Phe Tyr Ala Met Asp Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: CDRL1 of 1G3 antibody

<400> SEQUENCE: 22

Lys Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: CDRL2 of 1G3 antibody

<400> SEQUENCE: 23

Ser Ala Ser Tyr Arg Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: CDRL3 of 1G3 antibody

<400> SEQUENCE: 24

Gln Gln His Tyr Ser Thr Pro Pro Thr
1               5

<210> SEQ ID NO 25
<211> LENGTH: 5
<212> TYPE: PRT
<213> ORGANISM: Artificial Sequence
<220> FEATURE:
<223> OTHER INFORMATION: CDRH1 of hz8G11 antibody

<400> SEQUENCE: 25

Gly Tyr Tyr Met His
1               5
```

<210> SEQ ID NO 26
<211> LENGTH: 17
<212> TYPE: PRT
<213> ORGANISM: Artificial Sequence
<220> FEATURE:
<223> OTHER INFORMATION: CDRH2 of hz8G11 antibody

<400> SEQUENCE: 26

His Ile Asn Pro Asn Asn Gly Gly Thr Ser Tyr Asn Gln Lys Phe Lys
1               5                   10                  15

Gly

<210> SEQ ID NO 27
<211> LENGTH: 6
<212> TYPE: PRT
<213> ORGANISM: Artificial Sequence
<220> FEATURE:
<223> OTHER INFORMATION: CDRH3 of hz8G11 antibody

<400> SEQUENCE: 27

Glu Glu Ala Phe Ala Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: CDRL1 of hz8G11 antibody

<400> SEQUENCE: 28

Arg Ala Ser Gln Asp Ile Ser Asn Tyr Leu Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CDRL2 of hz8G11 antibody

<400> SEQUENCE: 29

Tyr Thr Ser Arg Leu His Ser
1               5

<210> SEQ ID NO 30
<211> LENGTH: 9
<212> TYPE: PRT
<213> ORGANISM: Artificial Sequence
<220> FEATURE:
<223> OTHER INFORMATION: CDRL3 of hz8G11 antibody

<400> SEQUENCE: 30

Gln Gln Gly Ile Thr Pro Pro Trp Thr
1               5

<210> SEQ ID NO 31
<211> LENGTH: 121
<212> TYPE: PRT
<213> ORGANISM: Artificial Sequence
<220> FEATURE:
<223> OTHER INFORMATION: Amino acid sequence of hz2G10 heavy chain
      variable region

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
            35                  40                  45

Ala Tyr Ile Asn Ser Gly Gly Gly Ser Thr Tyr Tyr Pro Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Leu Tyr Asp Tyr Asp Tyr Ala Met Asp Tyr Trp Gly
            100                 105                 110

Gln Gly Thr Thr Val Thr Val Ser Ser
        115                 120
```

<210> SEQ ID NO 32
<211> LENGTH: 363
<212> TYPE: DNA
<213> ORGANISM: Artificial Sequence
<220> FEATURE:
<223> OTHER INFORMATION: Nucleic acid sequence of hz2G10 heavy chain variable region

<400> SEQUENCE: 32

```
gaggtgcagt tggtcgagtc tggaggaggt ctggtacagc caggggggaag tctgagactg    60
agctgcgccg cttctggttt tacctttagc gattactata tgtattgggt aagacaggca   120
cctggtaaag gtttggaatg ggtggcctac ataaactcgg gcgggggcag cacctactac   180
ccggataccg tgaagggccg cttcaccatc tcccgagaca acgcgaaaaa ttcattgtat   240
ctgcaaatga actcacttag agctgaagat actgccgttt actactgcgc cagagaagca   300
ctctatgact atgattacgc tatggattac tgggggcagg gcacaaccgt cactgtttct   360
agt                                                                 363
```

<210> SEQ ID NO 33
<211> LENGTH: 451
<212> TYPE: PRT
<213> ORGANISM: Artificial Sequence
<220> FEATURE:
<223> OTHER INFORMATION: Amino acid sequence of hz2G10 heavy chain

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
            35                  40                  45

Ala Tyr Ile Asn Ser Gly Gly Gly Ser Thr Tyr Tyr Pro Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Leu Tyr Asp Tyr Asp Tyr Ala Met Asp Tyr Trp Gly
            100                 105                 110
```

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 34
<211> LENGTH: 1353
<212> TYPE: DNA
<213> ORGANISM: Artificial Sequence
<220> FEATURE:
<223> OTHER INFORMATION: Nucleic acid sequence of hz2G10 heavy chain

<400> SEQUENCE: 34
gaggtgcagt tggtcgagtc tggaggaggt ctggtacagc caggggggaag tctgagactg    60

| | | |
|---|---|---|
| agctgcgccg cttctggttt tacctttagc gattactata tgtattgggt aagacaggca | 120 |
| cctggtaaag gtttggaatg ggtggcctac ataaactcgg gcgggggcag cacctactac | 180 |
| ccggataccg tgaagggccg cttcaccatc tcccgagaca cgcgaaaaa ttcattgtat | 240 |
| ctgcaaatga actcacttag agctgaagat actgccgttt actactgcgc cagagaagca | 300 |
| ctctatgact atgattacgc tatggattac tgggggcagg gcacaaccgt cactgtttct | 360 |
| agtgcctcca ccaagggccc ctccgtgttc cctctggccc cctccagcaa gtccacctct | 420 |
| ggcggcacag ccgccctggg ctgcctggtg aaagactact ccccgagcc cgtgaccgtg | 480 |
| tcctggaact ctggcgccct gacctccggc gtgcacacct tcccgccgt gctgcagtcc | 540 |
| tccggcctgt actccctgtc ctccgtggtg accgtgccct ccagctctct gggcacccag | 600 |
| acctacatct gtaacgtgaa ccacaagccc tccaacacca aggtggacaa gaaggtggaa | 660 |
| cccaagtcct gcgacaagac ccacacctgt cccccctgcc ctgcccctga actgctgggc | 720 |
| ggaccttccg tgttcctgtt cccccccaaag cccaaggaca ccctgatgat ctcccggacc | 780 |
| cccgaagtga cctgcgtggt ggtggacgtg tcccacgagg accctgaagt gaagttcaat | 840 |
| tggtacgtgg acggcgtgga agtgcacaat gccaagacca gcccagaga ggaacagtac | 900 |
| aactccacct accgggtggt gtctgtgctg accgtgctgc accaggactg gctgaacggc | 960 |
| aaagaataca gtgcaaagt ctccaacaag gccctgcctg cccccatcga aagaccatc | 1020 |
| tccaaggcca agggccagcc ccgcgagccc caggtgtaca ccctgccccc tagccgggac | 1080 |
| gagctgacca gaaccaggt gtccctgacc tgtctggtga aaggcttcta ccoctccgac | 1140 |
| attgccgtgg aatgggagtc caacggccag cccgagaaca actacaagac cacccccct | 1200 |
| gtgctggact ccgacggctc attcttcctg tactccaagc tgaccgtgga caagtcccgg | 1260 |
| tggcagcagg gcaacgtgtt ctcctgctcc gtgatgcacg aggccctgca caaccactac | 1320 |
| acccagaagt ccctgtccct gagccccggc aag | 1353 |

<210> SEQ ID NO 35
<211> LENGTH: 112
<212> TYPE: PRT
<213> ORGANISM: Artificial Sequence
<220> FEATURE:
<223> OTHER INFORMATION: Amino acid sequence of hz2G10 light chain
      variable region

<400> SEQUENCE: 35

Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Leu Thr Phe Gly Gly Gly Thr Lys Val Glu Ile Lys
            100                 105                 110

<210> SEQ ID NO 36
<211> LENGTH: 336

<212> TYPE: DNA
<213> ORGANISM: Artificial Sequence
<220> FEATURE:
<223> OTHER INFORMATION: Nucleic acid sequence of hz2G10 light chain
      variable region

<400> SEQUENCE: 36

```
gacattgtca tgacgcagag ccccctttca ctcagcgtga ctcccggtca gcccgccagc    60
atttcctgta aaagctctca gtcgctcctg tacagcaatg gcaagactta tctgaattgg   120
ctgttacaga accaggcca agcccctcaa aggcttatct acctggtgag taagttagac    180
agcggggtgc ctgacagatt tagcggatct ggaagcggga ccgatttcac actaaaaatc   240
agcagggttg aggcagagga cgtgggcgtg tattattgtg tgcagggcac acacttccca   300
ctcacattcg ggggaggcac aaaggtggaa atcaag                             336
```

<210> SEQ ID NO 37
<211> LENGTH: 219
<212> TYPE: PRT
<213> ORGANISM: Artificial Sequence
<220> FEATURE:
<223> OTHER INFORMATION: Amino acid sequence of hz2G10 light chain

<400> SEQUENCE: 37

```
Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 38
<211> LENGTH: 657
<212> TYPE: DNA
<213> ORGANISM: Artificial Sequence
<220> FEATURE:
<223> OTHER INFORMATION: Nucleic acid sequence of hz2G10 light chain

<400> SEQUENCE: 38

```
gacattgtca tgacgcagag ccccctttca ctcagcgtga ctcccggtca gcccgccagc   60
atttcctgta aaagctctca gtcgctcctg tacagcaatg gcaagactta tctgaattgg  120
ctgttacaga aaccaggcca aagccctcaa aggcttatct acctggtgag taagttagac  180
agcggggtgc ctgacagatt tagcggatct ggaagcggga ccgatttcac actaaaaatc  240
agcagggttg aggcagagga cgtgggcgtg tattattgtg tgcagggcac acacttccca  300
ctcacattcg ggggaggcac aaaggtggaa atcaagcgga ccgtggccgc tcctccgtg   360
ttcatcttcc caccctccga cgagcagctg aagtccggca ccgccagcgt ggtctgcctg  420
ctgaacaact ctacccccg cgaggccaag gtgcagtgga aggtggacaa cgccctgcag   480
tccggcaact cccaggaatc cgtcaccgag caggactcca aggacagcac ctactccctg  540
tcctccaccc tgaccctgtc caaggccgac tacgagaagc acaaggtgta cgcctgcgaa  600
gtgacccacc agggcctgtc cagccccgtg accaagtcct caaccggggg cgagtgc     657
```

<210> SEQ ID NO 39
<211> LENGTH: 118
<212> TYPE: PRT
<213> ORGANISM: Artificial Sequence
<220> FEATURE:
<223> OTHER INFORMATION: Amino acid sequence of hz39D2 heavy chain variable region

<400> SEQUENCE: 39

```
Gln Val Gln Leu Val Gln Ser Gly Ser Glu Leu Lys Lys Pro Gly Ala
1               5                  10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Asp Tyr Tyr Val Arg Val Asp Tyr Trp Gly Gln Gly Thr
            100                 105                 110

Thr Val Thr Val Ser Ser
        115
```

<210> SEQ ID NO 40
<211> LENGTH: 354
<212> TYPE: DNA
<213> ORGANISM: Artificial Sequence
<220> FEATURE:
<223> OTHER INFORMATION: Nucleic acid sequence of hz39D2 heavy chain variable region

<400> SEQUENCE: 40

```
caagtccaac tcgtgcagtc aggatctgaa ctgaagaaac ctggagcgag cgttaaggtt   60
tcctgcaagg ccagcggcta tacgttcact aactatggtg tcaactgggt gagacaggca  120
cccggccagg gcctggagtg gatgggttgg atcaatactc acacagggga accaacatat  180
gctgaggagt tcaaaggacg gtttgttttt agtctggaca cctccgtgtc taccgcctac  240
```

```
ctgcagattt ccagccttaa agcagaggac actgctgtat actactgtgc cagagacgat     300
tactatgtga gggtggatta ctgggggcag gggaccaccg tgacagtctc aagt            354
```

<210> SEQ ID NO 41
<211> LENGTH: 448
<212> TYPE: PRT
<213> ORGANISM: Artificial Sequence
<220> FEATURE:
<223> OTHER INFORMATION: Amino acid sequence of hz39D2 heavy chain

<400> SEQUENCE: 41

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Asp Tyr Tyr Val Arg Val Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
                Pro Pro Ser Arg Asp Glu Leu Thr Lys Asn Gln Val Ser Leu Thr Cys
                        355                 360                 365

Leu Val Lys Gly Phe Tyr Pro Ser Asp Ile Ala Val Glu Trp Glu Ser
                    370                 375                 380

Asn Gly Gln Pro Glu Asn Asn Tyr Lys Thr Thr Pro Pro Val Leu Asp
                385                 390                 395                 400

Ser Asp Gly Ser Phe Phe Leu Tyr Ser Lys Leu Thr Val Asp Lys Ser
                                405                 410                 415

Arg Trp Gln Gln Gly Asn Val Phe Ser Cys Ser Val Met His Glu Ala
                                420                 425                 430

Leu His Asn His Tyr Thr Gln Lys Ser Leu Ser Leu Ser Pro Gly Lys
                        435                 440                 445

<210> SEQ ID NO 42
<211> LENGTH: 1344
<212> TYPE: DNA
<213> ORGANISM: Artificial Sequence
<220> FEATURE:
<223> OTHER INFORMATION: Nucleic acid sequence of hz39D2 heavy chain

<400> SEQUENCE: 42
caagtccaac tcgtgcagtc aggatctgaa ctgaagaaac ctggagcgag cgttaaggtt      60
tcctgcaagg ccagcggcta tacgttcact aactatggtg tcaactgggt gagacaggca     120
cccggccagg gcctggagtg gatgggttgg atcaatactc acacagggga accaacatat     180
gctgaggagt tcaaaggacg gtttgttttt agtctggaca cctccgtgtc taccgcctac     240
ctgcagattt ccagccttaa agcagaggac actgctgtat actactgtgc cagagacgat     300
tactatgtga gggtggatta ctgggggcag ggaccaccgt gacagtctc aagtgcctcc      360 accaagggcc cctccgtgtt ccctctggcc cctccagca gtccacctc tggcggcaca       420 gccgccctgg gctgcctggt gaaagactac ttccccgagc ccgtgaccgt gtcctggaac     480
tctggcgccc tgacctccgg cgtgcacacc ttccctgccg tgctgcagtc ctccggcctg     540
tactccctgt cctccgtggt gaccgtgccc tccagctctc tgggcaccca gacctacatc     600
tgtaacgtga accacaagcc ctccaacacc aaggtggaca agaaggtgga acccaagtcc     660
tgcgacaaga cccacacctg tcccccctgc cctgccccctg aactgctggg cggaccttcc     720
gtgttcctgt tcccccaaa gcccaaggac accctgatga tctcccggac ccccgaagtg      780
acctgcgtgg tggtggacgt gtcccacgag gaccctgaag tgaagttcaa ttggtacgtg     840
gacggcgtgg aagtgcacaa tgccaagacc aagcccagag aggaacagta caactccacc     900
taccgggtgg tgtctgtgct gaccgtgctg caccaggact ggctgaacgg caaagaatac     960
aagtgcaaag tctccaacaa ggccctgcct gcccccatcg aaaagaccat ctccaaggcc    1020
aagggccagc ccgcgagcc ccaggtgtac accctgcccc ctagccggga cgagctgacc      1080
aagaaccagg tgtccctgac ctgtctggtg aaaggcttct acccctccga cattgccgtg    1140
gaatgggagt ccaacggcca gccgagaac aactacaaga ccaccccccc tgtgctggac     1200
tccgacggct cattcttcct gtactccaag ctgaccgtgg acaagtcccg gtggcagcag    1260
ggcaacgtgt tctcctgctc cgtgatgcac gaggccctgc acaaccacta cacccagaag    1320
tccctgtccc tgagccccgg caag                                           1344

<210> SEQ ID NO 43
<211> LENGTH: 107
<212> TYPE: PRT
```

<213> ORGANISM: Artificial Sequence
<220> FEATURE:
<223> OTHER INFORMATION: Amino acid sequence of hz39D2 light chain
    variable region

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95

Thr Phe Gly Gln Gly Thr Lys Val Glu Ile Lys
            100                 105

<210> SEQ ID NO 44
<211> LENGTH: 321
<212> TYPE: DNA
<213> ORGANISM: Artificial Sequence
<220> FEATURE:
<223> OTHER INFORMATION: Nucleic acid sequence of hz39D2 light chain
    variable region

<400> SEQUENCE: 44

```
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctgcaa tacgatgagt tcccatggac cttcggccag     300
ggcaccaagg tggagattaa a                                               321
```

<210> SEQ ID NO 45
<211> LENGTH: 214
<212> TYPE: PRT
<213> ORGANISM: Artificial Sequence
<220> FEATURE:
<223> OTHER INFORMATION: Amino acid sequence of hz39D2 light chain

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 46
<211> LENGTH: 642
<212> TYPE: DNA
<213> ORGANISM: Artificial Sequence
<220> FEATURE:
<223> OTHER INFORMATION: Nucleic acid sequence of hz39D2 light chain

<400> SEQUENCE: 46

```
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctgcaa tacgatgagt cccatggaca cttcggccag     300
ggcaccaagg tggagattaa acggaccgtg gccgctccct ccgtgttcat cttcccaccc     360
tccgacgagc agctgaagtc cggcaccgcc agcgtggtct gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga aagcacaag gtgtacgcct gcgaagtgac ccaccagggc     600
ctgtccagcc ccgtgaccaa gtccttcaac cggggcgagt gc                        642
```

<210> SEQ ID NO 47
<211> LENGTH: 119
<212> TYPE: PRT
<213> ORGANISM: Artificial Sequence
<220> FEATURE:
<223> OTHER INFORMATION: Amino acid sequence of 24D3 heavy chain
      variable region

<400> SEQUENCE: 47

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Cys
            20                  25                  30

Ala Met Ser Trp Val Arg Gln Thr Pro Glu Lys Arg Leu Glu Trp Val
        35                  40                  45

Ala Thr Ile Ser Gly Gly Gly Ser Tyr Thr Tyr Tyr Pro Asp Ser Val
    50                  55                  60
```

```
Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg His Gly Gly Tyr Glu Ser Trp Phe Pro Tyr Trp Gly Gln Gly
            100                 105                 110

Thr Leu Val Thr Val Ser Ala
            115

<210> SEQ ID NO 48
<211> LENGTH: 357
<212> TYPE: DNA
<213> ORGANISM: Artificial Sequence
<220> FEATURE:
<223> OTHER INFORMATION: Nucleic acid sequence of 24D3 heavy chain
      variable region

<400> SEQUENCE: 48
gaggtgaagc tggtggagtc tgggggaggc ttagtgaagc ctggagggtc cctgaaactc    60
tcctgtgcag cctctggatt cactttcagt agctgtgcca tgtcttgggt ccgccagact   120
ccggagaaga ggctggagtg ggtcgcaacc attagtggtg gtggtagtta cacctactat   180
ccagacagtg tgaaggggcg attcaccatc tccagagaca atgccaagaa caccctgtac   240
ctgcaaatga gcagtctgag gtctgaggac acggccatgt attactgtgc aagacatggc   300
gggtacgagt cctggtttcc ttactggggc caagggactc tggtcactgt ctctgca      357

<210> SEQ ID NO 49
<211> LENGTH: 449
<212> TYPE: PRT
<213> ORGANISM: Artificial Sequence
<220> FEATURE:
<223> OTHER INFORMATION: Amino acid sequence of 24D3 heavy chain

<400> SEQUENCE: 49

Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Ser Cys
                 20                  25                  30

Ala Met Ser Trp Val Arg Gln Thr Pro Glu Lys Arg Leu Glu Trp Val
             35                  40                  45

Ala Thr Ile Ser Gly Gly Gly Ser Tyr Thr Tyr Tyr Pro Asp Ser Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg His Gly Gly Tyr Glu Ser Trp Phe Pro Tyr Trp Gly Gln Gly
            100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

|  |  |  | 180 |  |  | 185 |  |  | 190 |  |  |
|---|---|---|---|---|---|---|---|---|---|---|---|

Ser Ser Leu Gly Thr Gln Thr Tyr Ile Cys Asn Val Asn His Lys Pro
        195                200              205

Ser Asn Thr Lys Val Asp Lys Lys Val Glu Pro Lys Ser Cys Asp Lys
210               215              220

Thr His Thr Cys Pro Pro Cys Pro Ala Pro Glu Leu Leu Gly Gly Pro
225               230            235              240

Ser Val Phe Leu Phe Pro Pro Lys Pro Lys Asp Thr Leu Met Ile Ser
        245                250              255

Arg Thr Pro Glu Val Thr Cys Val Val Val Asp Val Ser His Glu Asp
          260              265            270

Pro Glu Val Lys Phe Asn Trp Tyr Val Asp Gly Val Glu Val His Asn
        275                280            285

Ala Lys Thr Lys Pro Arg Glu Glu Gln Tyr Asn Ser Thr Tyr Arg Val
          290              295            300

Val Ser Val Leu Thr Val Leu His Gln Asp Trp Leu Asn Gly Lys Glu
305             310             315              320

Tyr Lys Cys Lys Val Ser Asn Lys Ala Leu Pro Ala Pro Ile Glu Lys
            325              330           335

Thr Ile Ser Lys Ala Lys Gly Gln Pro Arg Glu Pro Gln Val Tyr Thr
          340              345            350

Leu Pro Pro Ser Arg Asp Glu Leu Thr Lys Asn Gln Val Ser Leu Thr
        355                360            365

Cys Leu Val Lys Gly Phe Tyr Pro Ser Asp Ile Ala Val Glu Trp Glu
          370              375            380

Ser Asn Gly Gln Pro Glu Asn Asn Tyr Lys Thr Thr Pro Pro Val Leu
385               390            395              400

Asp Ser Asp Gly Ser Phe Phe Leu Tyr Ser Lys Leu Thr Val Asp Lys
        405                410            415

Ser Arg Trp Gln Gln Gly Asn Val Phe Ser Cys Ser Val Met His Glu
          420              425            430

Ala Leu His Asn His Tyr Thr Gln Lys Ser Leu Ser Leu Ser Pro Gly
        435                440            445

Lys

```
<210> SEQ ID NO 50
<211> LENGTH: 1347
<212> TYPE: DNA
<213> ORGANISM: Artificial Sequence
<220> FEATURE:
<223> OTHER INFORMATION: Nucleic acid sequence of 24D3 heavy chain

<400> SEQUENCE: 50
```
gaggtgaagc tggtggagtc tgggggaggc ttagtgaagc ctggagggtc cctgaaactc     60
tcctgtgcag cctctggatt cactttcagt agctgtgcca tgtcttgggt ccgccagact    120
ccggagaaga ggctggagtg ggtcgcaacc attagtggtg gtggtagtta cacctactat    180
ccagacagtg tgaaggggcg attcaccatc tccagagaca atgccaagaa caccctgtac    240
ctgcaaatga gcagtctgag gtctgaggac acggccatgt attactgtgc aagacatggc    300
gggtacgagt cctggttttcc ttactgggc caagggactc tggtcactgt ctctgcagcc    360
tccaccaagg gcccctccgt gttccctctg gccccctcca gcaagtccac ctctggcggc    420
acagccgccc tgggctgcct ggtgaaagac tacttccccg agcccgtgac cgtgtcctgg    480
aactctggcg ccctgacctc cggcgtgcac accttccctg ccgtgctgca gtcctccggc    540

```
ctgtactccc tgtcctccgt ggtgaccgtg ccctccagct ctctgggcac ccagacctac     600
atctgtaacg tgaaccacaa gccctccaac accaaggtgg acaagaaggt ggaacccaag     660
tcctgcgaca agacccacac ctgtcccccc tgccctgccc ctgaactgct gggcggacct     720
tccgtgttcc tgttcccccc aaagcccaag gacacccctg atctctcccg gacccccgaa     780
gtgacctgcg tggtggtgga cgtgtcccac gaggaccctg aagtgaagtt caattggtac     840
gtggacggcg tggaagtgca caatgccaag accaagccca gagaggaaca gtacaactcc     900
acctaccggg tggtgtctgt gctgaccgtg ctgcaccagg actggctgaa cggcaaagaa     960
tacaagtgca aagtctccaa caaggccctg cctgccccca tcgaaaagac catctcccaa    1020
gccaagggcc agccccgcga gccccaggtg tacaccctgc ccctagccg ggacgagctg    1080 accaagaacc aggtgtccct gacctgtctg gtgaaaggct tctacccctc cgacattgcc    1140
gtggaatggg agtccaacgg ccagcccgag aacaactaca agaccacccc ccctgtgctg    1200
gactccgacg gctcattctt cctgtactcc aagctgaccg tggacaagtc cggtggcag    1260 cagggcaacg tgttctcctg ctccgtgatg cacgaggccc tgcacaacca ctacacccag    1320
aagtccctgt ccctgagccc cggcaag                                        1347
```

<210> SEQ ID NO 51
<211> LENGTH: 113
<212> TYPE: PRT
<213> ORGANISM: Artificial Sequence
<220> FEATURE:
<223> OTHER INFORMATION: Amino acid sequence of 24D3 light chain
      variable region

<400> SEQUENCE: 51

```
Asp Ile Val Met Thr Gln Ser Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys
```

<210> SEQ ID NO 52
<211> LENGTH: 339
<212> TYPE: DNA
<213> ORGANISM: Artificial Sequence
<220> FEATURE:
<223> OTHER INFORMATION: Nucleic acid sequence of 24D3 light chain
      variable region

<400> SEQUENCE: 52

```
gatattgtga tgacccagtc tccactctcc ctgcctgtca gtcttggaga tcaagcctcc      60
atctcttgca gatctagtca gagccttgta cacagtaatg aaacacccta tttacattgg     120
tacctgcaga agccaggcca gtctccaaag ctcctgatct acaaagtttc caaccgattt     180
```

```
tctggggttc cagacaggtt cagtggcagt ggatcaggga cagatttcac actcaagatc    240
agcagagtgg aggctgagga tctgggagtt tatttctgct ctcaaagtac acatgttcct    300
ccgtggacgt tcggtggagg gaccaagctg gaaatcaaa                          339
```

<210> SEQ ID NO 53
<211> LENGTH: 220
<212> TYPE: PRT
<213> ORGANISM: Artificial Sequence
<220> FEATURE:
<223> OTHER INFORMATION: Amino acid sequence of 24D3 light chain

<400> SEQUENCE: 53

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 54
<211> LENGTH: 660
<212> TYPE: DNA
<213> ORGANISM: Artificial Sequence
<220> FEATURE:
<223> OTHER INFORMATION: Nucleic acid sequence of 24D3 light chain

<400> SEQUENCE: 54

```
gatattgtga tgacccagtc tccactctcc ctgcctgtca gtcttggaga tcaagcctcc     60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggttc cagacaggtt cagtggcagt ggatcaggga cagatttcac actcaagatc    240
agcagagtgg aggctgagga tctgggagtt tatttctgct ctcaaagtac acatgttcct    300
```

```
ccgtggacgt tcggtggagg gaccaagctg gaaatcaaac ggaccgtggc cgctccctcc      360
gtgttcatct tcccaccctc cgacgagcag ctgaagtccg gcaccgccag cgtggtctgc      420
ctgctgaaca acttctaccc ccgcgaggcc aaggtgcagt ggaaggtgga caacgccctg      480
cagtccggca actcccagga atccgtcacc gagcaggact ccaaggacag cacctactcc      540
ctgtcctcca ccctgacccT gtccaaggcc gactacgaga agcacaaggt gtacgcctgc      600
gaagtgaccc accagggcct gtccagcccc gtgaccaagt ccttcaaccg ggcgagtgc       660
```

<210> SEQ ID NO 55
<211> LENGTH: 119
<212> TYPE: PRT
<213> ORGANISM: Artificial Sequence
<220> FEATURE:
<223> OTHER INFORMATION: Amino acid sequence of 1G3 heavy chain variable region

<400> SEQUENCE: 55

```
Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Val Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Thr Arg Tyr Asp Pro Asn Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Tyr Tyr Gly Phe Tyr Ala Met Asp Tyr Trp Gly Gln Gly
            100                 105                 110

Thr Thr Val Thr Val Ser Ser
        115
```

<210> SEQ ID NO 56
<211> LENGTH: 357
<212> TYPE: DNA
<213> ORGANISM: Artificial Sequence
<220> FEATURE:
<223> OTHER INFORMATION: Nucleic acid sequence of 1G3 heavy chain variable region

<400> SEQUENCE: 56

```
gaggttcagc tgcagcagtc tggggcagag cttgtgaagc caggggcctc agtcaagttg       60
tcctgcacag cttctgactt caacattgta gacacctata tgcactgggt gaagcagagg      120
cctgaacagg gcctggagtg gattggaagg attgatcctg cgaatggtta tactagatat      180
gacccgaact tccagggcaa ggccactata acagcagaca catcctccaa cacagcctac      240
ctgcagctca gcagcctgac atctgaggac actgccgtct attactgtgc ccgttattac      300
tacggcttct atgctatgga ctactggggt caaggaacca cggtcaccgt ctcctca        357
```

<210> SEQ ID NO 57
<211> LENGTH: 449
<212> TYPE: PRT
<213> ORGANISM: Artificial Sequence
<220> FEATURE:
<223> OTHER INFORMATION: Amino acid sequence of 1G3 heavy chain

<400> SEQUENCE: 57

```
Glu Val Gln Leu Gln Gln Ser Gly Ala Glu Leu Val Lys Pro Gly Ala
 1               5                  10                  15

Ser Val Lys Leu Ser Cys Thr Ala Ser Asp Phe Asn Ile Val Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Thr Arg Tyr Asp Pro Asn Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Tyr Tyr Gly Phe Tyr Ala Met Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 58
<211> LENGTH: 1347
<212> TYPE: DNA
<213> ORGANISM: Artificial Sequence
<220> FEATURE:
<223> OTHER INFORMATION: Nucleic acid sequence of 1G3 heavy chain

<400> SEQUENCE: 58

| gaggttcagc tgcagcagtc tggggcagag cttgtgaagc caggggcctc agtcaagttg | 60 |
| tcctgcacag cttctgactt caacattgta gacacctata tgcactgggt gaagcagagg | 120 |
| cctgaacagg gcctggagtg gattggaagg attgatcctg cgaatggtta tactagatat | 180 |
| gacccgaact tccagggcaa ggccactata acagcagaca tcctccaaac acagcctac | 240 |
| ctgcagctca gcagcctgac atctgaggac actgccgtct attactgtgc ccgttattac | 300 |
| tacggcttct atgctatgga ctactggggt caaggaacca cggtcaccgt ctcctcagcc | 360 |
| tccaccaagg gcccctccgt gttccctctg gccccctcca gcaagtccac ctctggcggc | 420 |
| acagccgccc tgggctgcct ggtgaaagac tacttccccg agcccgtgac cgtgtcctgg | 480 |
| aactctggcg ccctgacctc cggcgtgcac accttccctg ccgtgctgca gtcctccggc | 540 |
| ctgtactccc tgtcctccgt ggtgaccgtg ccctccagct ctctgggcac ccagacctac | 600 |
| atctgtaacg tgaaccacaa gccctccaac accaaggtgg acaagaaggt ggaacccaag | 660 |
| tcctgcgaca gacccacac tgtccccccc tgccctgccc ctgaactgct gggcggacct | 720 |
| tccgtgttcc tgttcccccc aaagcccaag gacaccctga tgatctcccg gacccccgaa | 780 |
| gtgacctgcg tggtggtgga cgtgtcccac gaggaccctg aagtgaagtt caattggtac | 840 |
| gtggacggcg tggaagtgca caatgccaag accagcccca gagaggaaca gtacaactcc | 900 |
| acctaccggg tggtgtctgt gctgaccgtg ctgcaccagg actggctgaa cggcaaagaa | 960 |
| tacaagtgca agtctccaa caaggccctg cctgccccca tcgaaaagac catctccaag | 1020 |
| gccaagggcc agccccgcga gccccaggtg tacaccctgc cccctagccg ggacgagctg | 1080 |
| accaagaacc aggtgtccct gacctgtctg gtgaaaggct tctacccctc cgacattgcc | 1140 |
| gtggaatggg agtccaacgg ccagcccgag aacaactaca agaccaccc cctgtgctg | 1200 |
| gactccgacg gctcattctt cctgtactcc aagctgaccg tggacaagtc ccggtggcag | 1260 |
| cagggcaacg tgttctcctg ctccgtgatg cacgaggccc tgcacaacca ctacacccag | 1320 |
| aagtccctgt ccctgagccc cggcaag | 1347 |

<210> SEQ ID NO 59
<211> LENGTH: 107
<212> TYPE: PRT
<213> ORGANISM: Artificial Sequence
<220> FEATURE:
<223> OTHER INFORMATION: Amino acid sequence of 1G3 light chain variable
      region

<400> SEQUENCE: 59

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala

```
                    20                  25                  30
Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Thr Phe Gly Gly Gly Thr Lys Leu Glu Leu Lys
            100                 105

<210> SEQ ID NO 60
<211> LENGTH: 321
<212> TYPE: DNA
<213> ORGANISM: Artificial Sequence
<220> FEATURE:
<223> OTHER INFORMATION: Nucleic acid sequence of 1G3 light chain
      variable region

<400> SEQUENCE: 60
gatattgtga tgacgcagtc tcacaaattc atgtccacat cagtaggaga cagggtcagc      60
atcacctgca aggccagtca ggatgtgagt actgctgtag cctggtatca acagaaacca    120
ggacaatctc ctaaactact gatttactcg gcatcctacc ggtacactgg agtccctgat    180
cgcttcactg gcagtggatc tgggacggat ttcactttca ccatcagcag tgtgcaggct    240
gaagacctgg cagtttatta ctgtcagcaa cattatagta ctcctcccac gttcggaggg    300
gggaccaagc tggagctgaa a                                              321

<210> SEQ ID NO 61
<211> LENGTH: 214
<212> TYPE: PRT
<213> ORGANISM: Artificial Sequence
<220> FEATURE:
<223> OTHER INFORMATION: Amino acid sequence of 1G3 light chain

<400> SEQUENCE: 61

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 62
<211> LENGTH: 642
<212> TYPE: DNA
<213> ORGANISM: Artificial Sequence
<220> FEATURE:
<223> OTHER INFORMATION: Nucleic acid sequence of 1G3 light chain

<400> SEQUENCE: 62

```
gatattgtga tgacgcagtc tcacaaattc atgtccacat cagtaggaga cagggtcagc    60
atcacctgca aggccagtca ggatgtgagt actgctgtag cctggtatca acagaaacca   120
ggacaatctc ctaaactact gatttactcg gcatcctacc ggtacactgg agtccctgat   180
cgcttcactg gcagtggatc tgggacggat ttcactttca ccatcagcag tgtgcaggct   240
gaagacctgg cagtttatta ctgtcagcaa cattatagta ctcctcccac gttcggaggg   300
gggaccaagc tggagctgaa acggaccgtg gccgctccct ccgtgttcat cttcccaccc   360
tccgacgagc agctgaagtc cggcaccgcc agcgtggtct gcctgctgaa caacttctac   420
ccccgcgagg ccaaggtgca gtggaaggtg gacaacgccc tgcagtccgg caactcccag   480
gaatccgtca ccgagcagga ctccaaggac agcacctact ccctgtcctc caccctgacc   540
ctgtccaagg ccgactacga aagcacaag gtgtacgcct gcgaagtgac ccaccagggc   600
ctgtccagcc ccgtgaccaa gtccttcaac cggggcgagt gc                      642
```

<210> SEQ ID NO 63
<211> LENGTH: 115
<212> TYPE: PRT
<213> ORGANISM: Artificial Sequence
<220> FEATURE:
<223> OTHER INFORMATION: Amino acid sequence of hz8G11 heavy chain
      variable region

<400> SEQUENCE: 63

Gln Val Gln Leu Val Gln Ser Gly Gln Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
            35                  40                  45

Gly His Ile Asn Pro Asn Asn Gly Gly Thr Ser Tyr Asn Gln Lys Phe
    50                  55                  60

Lys Gly Arg Thr Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Glu Ala Phe Ala Tyr Trp Gly Gln Gly Thr Leu Val Thr
            100                 105                 110

Val Ser Ser
            115

<210> SEQ ID NO 64
<211> LENGTH: 345
<212> TYPE: DNA
<213> ORGANISM: Artificial Sequence
<220> FEATURE:
<223> OTHER INFORMATION: Nucleic acid sequence of hz8G11 heavy chain variable region

<400> SEQUENCE: 64

```
caggtacagc tagtgcagag cggccaggaa gtaaagaagc caggcgcctc tgttaaggtg      60
tcatgtaagg ccagcggtta cagcttcact ggctattaca tgcactgggt ccggcaggca     120
cccggacaag ggctggaatg gataggtcac attaatccaa acaatggcgg taccagttat     180
aaccagaaat ttaaggggag gacaacccctg acagttgata atccatcag tacagcatat    240 atggagctca gcagactgag aagcgacgat actgctgtgt actactgcgc gcgggaggag    300
gctttcgcct actggggcca aggaccttta gtgactgtct catca                    345
```

<210> SEQ ID NO 65
<211> LENGTH: 445
<212> TYPE: PRT
<213> ORGANISM: Artificial Sequence
<220> FEATURE:
<223> OTHER INFORMATION: Amino acid sequence of hz8G11 heavy chain

<400> SEQUENCE: 65

Gln Val Gln Leu Val Gln Ser Gly Gln Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Gly Leu Glu Trp Ile
            35                  40                  45

Gly His Ile Asn Pro Asn Asn Gly Gly Thr Ser Tyr Asn Gln Lys Phe
        50                  55                  60

Lys Gly Arg Thr Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Glu Ala Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

```
Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 66
<211> LENGTH: 1335
<212> TYPE: DNA
<213> ORGANISM: Artificial Sequence
<220> FEATURE:
<223> OTHER INFORMATION: Nucleic acid sequence of hz8G11 heavy chain

<400> SEQUENCE: 66
caggtacagc tagtgcagag cggccaggaa gtaaagaagc caggcgcctc tgttaaggtg      60
tcatgtaagg ccagcggtta cagcttcact ggctattaca tgcactgggt ccggcaggca     120 cccgacaag ggctggaatg gataggtcac attaatccaa acaatggcgg taccagttat     180
aaccagaaat ttaaggggag acaaccctg acagttgata atccatcag tacagcatat     240 atggagctca gcagactgag aagcgacgat actgctgtgt actactgcgc gcgggaggag     300
gctttcgcct actggggcca agggaccta gtgactgtct catcagcctc caccaagggc     360
ccctccgtgt tccctctggc ccctccagc aagtccacct ctggcggcac agccgccctg     420
ggctgcctgg tgaaagacta cttccccgag cccgtgaccg tgtcctggaa ctctggcgcc     480
ctgacctccg gcgtgcacac cttccctgcc gtgctgcagt cctccggcct gtactccctg     540
tcctccgtgg tgaccgtgcc ctccagctct ctgggcaccc agacctacat ctgtaacgtg     600
aaccacaagc cctccaacac caaggtggac aagaaggtgg aacccaagtc ctgcgacaag     660
acccacacct gtccccctg ccctgcccct gaactgctgg gcggaccttc cgtgttcctg     720
ttccccccaa agcccaagga caccctgatg atctcccgga ccccgaagt gacctgcgtg     780 gtggtggacg tgtcccacga ggaccctgaa gtgaagttca attggtacgt ggacggcgtg     840
gaagtgcaca tgccaagac caagcccaga gaggaacagt acaactccac ctaccgggtg     900
```

```
gtgtctgtgc tgaccgtgct gcaccaggac tggctgaacg gcaaagaata caagtgcaaa    960
gtctccaaca aggccctgcc tgccccatc gaaaagacca tctccaaggc caagggccag   1020
ccccgcgagc ccaggtgta caccctgccc ctagccggg acgagctgac caagaaccag    1080
gtgtccctga cctgtctggt gaaaggcttc taccccctccg acattgccgt ggaatgggag  1140
tccaacggcc agcccgagaa caactacaag accacccccc ctgtgctgga ctccgacggc  1200
tcattcttcc tgtactccaa gctgaccgtg gacaagtccc ggtggcagca gggcaacgtg  1260
ttctcctgct ccgtgatgca cgaggccctg cacaaccact acacccagaa gtccctgtcc  1320
ctgagccccg gcaag                                                   1335
```

<210> SEQ ID NO 67
<211> LENGTH: 107
<212> TYPE: PRT
<213> ORGANISM: Artificial Sequence
<220> FEATURE:
<223> OTHER INFORMATION: Amino acid sequence of hz8G11 light chain
      variable region

<400> SEQUENCE: 67

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Ile Ala Thr Tyr Tyr Cys Gln Gln Gly Ile Thr Pro Pro Trp
                85                  90                  95

Thr Phe Gly Gly Gly Thr Lys Val Glu Ile Lys
            100                 105
```

<210> SEQ ID NO 68
<211> LENGTH: 321
<212> TYPE: DNA
<213> ORGANISM: Artificial Sequence
<220> FEATURE:
<223> OTHER INFORMATION: Nucleic acid sequence of hz8G11 light chain
      variable region

<400> SEQUENCE: 68

```
gacatacaga tgacgcagag ccctagttca ctgtctgcct ccgtcggcga cagagtgacg     60
atcagctgcc gagccagcca agatattagt aactacctca attggtacca gcagaaacct    120
ggaaaagcac ccaagctttt gatctattac accagcaggc tgcatagcgg agtgccgagc    180
agattttcgg gttctggcag cggcaccgat ttctctctga ctatcagtag cctgcaaccc    240
gaagacattg ctacatatta ttgtcagcag ggaatcaccc ctccatggac atttggaggg    300
ggaacaaagg tggagattaa a                                              321
```

<210> SEQ ID NO 69
<211> LENGTH: 214
<212> TYPE: PRT
<213> ORGANISM: Artificial Sequence
<220> FEATURE:
<223> OTHER INFORMATION: Amino acid sequence of hz8G11 light chain

<400> SEQUENCE: 69

```
Asp Ile Gln Met Thr Gln Ser Pro Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Ser Leu Thr Ile Ser Ser Leu Gln Pro
65                  70                  75                  80

Glu Asp Ile Ala Thr Tyr Tyr Cys Gln Gln Gly Ile Thr Pro Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 70
<211> LENGTH: 642
<212> TYPE: DNA
<213> ORGANISM: Artificial Sequence
<220> FEATURE:
<223> OTHER INFORMATION: Nucleic acid sequence of hz8G11 light chain

<400> SEQUENCE: 70

```
gacatacaga tgacgcagag ccctagttca ctgtctgcct ccgtcggcga cagagtgacg    60
atcagctgcc gagccagcca agatattagt aactacctca attggtacca gcagaaacct   120
ggaaaagcac ccaagctttt gatctattac accagcaggc tgcatagcgg agtgccgagc   180
agattttcgg gttctggcag cggcaccgat ttctctctga ctatcagtag cctgcaaccc   240
gaagacattg ctacatatta ttgtcagcag ggaatcaccc ctccatggac atttggaggg   300
ggaacaaagg tggagattaa acggaccgtg gccgctccct ccgtgttcat cttcccaccc   360
tccgacgagc agctgaagtc cggcaccgcc agcgtggtct gctgctgaa caacttctac   420
ccccgcgagg ccaaggtgca gtggaaggtg gacaacgccc tgcagtccgg caactcccag   480
gaatccgtca ccgagcagga ctccaaggac agcacctact ccctgtcctc cacccctgacc   540
ctgtccaagg ccgactacga aagcacaag gtgtacgcct gcgaagtgac ccaccagggc   600
ctgtccagcc ccgtgaccaa gtccttcaac cggggcgagt gc                       642
```

<210> SEQ ID NO 71
<211> LENGTH: 9

```
<212> TYPE: PRT
<213> ORGANISM: Artificial Sequence
<220> FEATURE:
<223> OTHER INFORMATION: CDRH3 of hz39D2.14 antibody

<400> SEQUENCE: 71

Asp Glu Tyr Tyr Val Arg Thr Asp Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: CDRH3 of hz39D2.22 and hz39D2.23 antibody

<400> SEQUENCE: 72

Asp Glu Tyr Tyr Val Arg Val Asp Tyr
1               5

<210> SEQ ID NO 73
<211> LENGTH: 9
<212> TYPE: PRT
<213> ORGANISM: Artificial Sequence
<220> FEATURE:
<223> OTHER INFORMATION: CDRL3 of hz39D2.22 antibody

<400> SEQUENCE: 73

Leu Glu Leu Asp Glu Phe Pro Trp Thr
1               5

<210> SEQ ID NO 74
<211> LENGTH: 9
<212> TYPE: PRT
<213> ORGANISM: Artificial Sequence
<220> FEATURE:
<223> OTHER INFORMATION: CDRL3 of hz39D2.23 antibody

<400> SEQUENCE: 74

Leu Gln Leu Asp Glu Phe Pro Trp Thr
1               5

<210> SEQ ID NO 75
<211> LENGTH: 121
<212> TYPE: PRT
<213> ORGANISM: Artificial Sequence
<220> FEATURE:
<223> OTHER INFORMATION: Amino acid sequence of 2G10 heavy chain
      variable region

<400> SEQUENCE: 75

Glu Val Lys Leu Leu Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Met Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Glu Ala Leu Tyr Asp Tyr Asp Tyr Ala Met Asp Tyr Trp Gly
```

```
                        100                 105                 110
Gln Gly Thr Thr Val Thr Val Ser Ser
            115                 120

<210> SEQ ID NO 76
<211> LENGTH: 363
<212> TYPE: DNA
<213> ORGANISM: Artificial Sequence
<220> FEATURE:
<223> OTHER INFORMATION: Nucleic acid sequence of 2G10 heavy chain
      variable region

<400> SEQUENCE: 76
gaggtgaagc ttctcgagtc tgggggaggc ttagtgcagc ctggagggtc cctgaaactc      60
tcctgtgcaa cctctggatt cactttcagt gactattaca tgtattgggt tcgccagact     120
ccagagatga ggctggagtg ggtcgcatat attaatagtg gtggtggtag cacctattat     180
ccagacactg taaagggccg attcaccatc tccagagaca tgccaagaa cacccctgtac     240 ctgcaaatga gccgtctgaa gtctgaggac acagccatgt attactgtgc aagagaggcc     300
ctctatgatt acgactatgc tatggactac tggggtcaag gaaccacggt caccgtctcc     360
tca                                                                   363

<210> SEQ ID NO 77
<211> LENGTH: 112
<212> TYPE: PRT
<213> ORGANISM: Artificial Sequence
<220> FEATURE:
<223> OTHER INFORMATION: Amino acid sequence of 2G10 light chain
      variable region

<400> SEQUENCE: 77

Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Leu Thr Phe Gly Ala Gly Thr Lys Leu Glu Leu Lys
            100                 105                 110

<210> SEQ ID NO 78
<211> LENGTH: 336
<212> TYPE: DNA
<213> ORGANISM: Artificial Sequence
<220> FEATURE:
<223> OTHER INFORMATION: Nucleic acid sequence of 2G10 light chain
      variable region

<400> SEQUENCE: 78
gatattgtga tgacccagtc tccactcact ttgtcggtta ccattggaca accagcctct      60
atctcttgca agtcaagtca gagcctctta tatagtaatg gaaaaaccta tttgaattgg     120
ttattacaga ggccaggcca gtctccaaag cgcctaatct atctggtgtc taaactggac     180
```

| | |
|---|---:|
| tctggagtcc ctgacaggtt cactggcagt gggtcaggaa cagattttac actgaaaatc | 240 |
| agcagagtgg aggctgagga tttgggagtt tattactgcg tgcaaggtac acattttccg | 300 |
| ctcacgttcg gtgctgggac caagctggag ctgaaa | 336 |

```
<210> SEQ ID NO 79
<211> LENGTH: 115
<212> TYPE: PRT
<213> ORGANISM: Artificial Sequence
<220> FEATURE:
<223> OTHER INFORMATION: Amino acid sequence of 8G11 heavy chain
      variable region

<400> SEQUENCE: 79
```

Glu Val Gln Leu Gln Gln Ser Gly Pro Asp Leu Val Lys Pro Gly Thr
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Gly Lys Ser Leu Glu Trp Ile
            35                  40                  45

Gly His Ile Asn Pro Asn Asn Gly Gly Thr Ser Tyr Asn Gln Lys Phe
        50                  55                  60

Lys Gly Lys Thr Ile Leu Thr Val Asp Lys Ser Ser Thr Ala Phe
65                  70                  75                  80

Met Glu Leu Arg Ser Leu Thr Ser Glu Asp Ser Ala Val Tyr Tyr Cys
                85                  90                  95

Ala Arg Glu Glu Ala Phe Ala Tyr Trp Gly Gln Gly Thr Leu Val Thr
                100                 105                 110

Val Ser Ala
        115

```
<210> SEQ ID NO 80
<211> LENGTH: 345
<212> TYPE: DNA
<213> ORGANISM: Artificial Sequence
<220> FEATURE:
<223> OTHER INFORMATION: Nucleic acid sequence of 8G11 heavy chain
      variable region

<400> SEQUENCE: 80
```

| | |
|---|---:|
| gaggtgcaac ttcagcagtc tggacctgac ctggtgaagc ctgggacttc agtgaagata | 60 |
| tcctgcaagg cttctggtta ctcattcact ggctactaca tgcactgggt gaagcagagc | 120 |
| catggaaaga gccttgagtg gattggacat attaatccta acaatggtgg tactagctac | 180 |
| aaccagaagt tcaagggcaa gaccatatta actgtggaca agtcttccag cacagccttc | 240 |
| atggagctcc gcagcctgac atctgaggac tctgcggtct attactgtgc aagagaagaa | 300 |
| gcctttgctt actggggcca aggactctg gtcactgtct ctgca | 345 |

```
<210> SEQ ID NO 81
<211> LENGTH: 107
<212> TYPE: PRT
<213> ORGANISM: Artificial Sequence
<220> FEATURE:
<223> OTHER INFORMATION: Amino acid sequence of 8G11 light chain
      variable region

<400> SEQUENCE: 81
```

Asp Ile Val Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr 20                  25                  30
Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Ser Leu Thr Ile Ser Asn Val Glu Gln
65                  70                  75                  80

Glu Asp Ile Ala Thr Tyr Phe Cys Gln Gln Gly Ile Thr Pro Pro Trp
                85                  90                  95

Thr Phe Gly Gly Gly Thr Lys Leu Glu Leu Lys
            100                 105

<210> SEQ ID NO 82
<211> LENGTH: 321
<212> TYPE: DNA
<213> ORGANISM: Artificial Sequence
<220> FEATURE:
<223> OTHER INFORMATION: Nucleic acid sequence of 8G11 light chain
      variable region

<400> SEQUENCE: 82
gatattgtga tgacccagtc tacatcctcc ctgtctgcct ctctgggaga cagagtcacc      60
atcagttgca gggcaagtca ggacattagc aattatttaa actggtatca gcagaaacca    120
gatggaactg ttaaactcct gatctactac acatcaagat acactcagg agtcccatca     180 aggttcagtg gcagtgggtc tggaacagat ttttctctca ccattagcaa cgtggagcaa    240
gaagacattg ccacttactt ttgccaacag ggtattacgc tccgtggac gttcggtgga     300 gggaccaagc tggagctgaa a                                              321

<210> SEQ ID NO 83
<211> LENGTH: 118
<212> TYPE: PRT
<213> ORGANISM: Artificial Sequence
<220> FEATURE:
<223> OTHER INFORMATION: Amino acid sequence of 39D2 heavy chain
      variable region

<400> SEQUENCE: 83

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Val Asn Trp Val Lys Gln Ala Pro Gly Lys Gly Leu Lys Trp Met
            35                  40                  45

Gly Trp Ile Asn Thr His Thr Gly Glu Pro Thr Tyr Ala Glu Glu Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Asp Tyr Tyr Val Arg Val Asp Tyr Trp Gly Gln Gly Thr
            100                 105                 110

Thr Leu Thr Val Ser Ser
            115

<210> SEQ ID NO 84
<211> LENGTH: 354
<212> TYPE: DNA

<213> ORGANISM: Artificial Sequence
<220> FEATURE:
<223> OTHER INFORMATION: Nucleic acid sequence of 39D2 heavy chain
     variable region

<400> SEQUENCE: 84

```
gaggttcagc tgcagcagtc tggacctgag ctgaagaagc ctggagagac agtcaagatc       60
tcctgcaagg cttctgggta taccttcaca aactatggag tgaattgggt gaagcaggct      120
ccaggaaagg gtttaaagtg gatgggctgg ataaacaccc acactggaga gccaacatat      180
gctgaagagt tcaagggacg gtttgccttc tctttggaaa cctctgccag cactgcctat      240
ttgcagatca caaccctcaa aaatgaggac acggctacat atttctgtgc aagagatgat      300
tactacgtaa gggtagacta ctggggccaa ggcaccactc tcacagtctc ctca            354
```

<210> SEQ ID NO 85
<211> LENGTH: 107
<212> TYPE: PRT
<213> ORGANISM: Artificial Sequence
<220> FEATURE:
<223> OTHER INFORMATION: Amino acid sequence of 39D2 light chain
     variable region

<400> SEQUENCE: 85

```
Asp Ile Val Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Trp
                85                  90                  95

Thr Phe Gly Gly Gly Thr Lys Leu Glu Leu Lys
            100                 105
```

<210> SEQ ID NO 86
<211> LENGTH: 321
<212> TYPE: DNA
<213> ORGANISM: Artificial Sequence
<220> FEATURE:
<223> OTHER INFORMATION: Nucleic acid sequence of 39D2 light chain
     variable region

<400> SEQUENCE: 86

```
gatattgtaa tgacccagtc tccatcttcc atgtatgcat ccctaggaga gagagtcact       60
atcacttgca aggcgagtca ggacattaat agctatttaa gctggttcca gcagaaacca      120
gggaaatctc ctaagaccct gatctatcgt gcaaacagat tggtagatgg ggtcccatca      180
aggttcagtg gcagtggatc tgggcaagat tattctctca ccatcagcag cctggagtat      240
gaagatatgg gaatttatta ttgtctacag tatgatgagt ttccgtggac gttcggtgga      300
gggaccaagc tggagctgaa a                                                321
```

<210> SEQ ID NO 87
<211> LENGTH: 118
<212> TYPE: PRT
<213> ORGANISM: Artificial Sequence
<220> FEATURE:
<223> OTHER INFORMATION: Amino acid sequence of hz39D2.14 heavy chain
      variable region

<400> SEQUENCE: 87

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Glu Tyr Tyr Val Arg Thr Asp Tyr Trp Gly Gln Gly Thr
            100                 105                 110

Thr Val Thr Val Ser Ser
        115
```

<210> SEQ ID NO 88
<211> LENGTH: 354
<212> TYPE: DNA
<213> ORGANISM: Artificial Sequence
<220> FEATURE:
<223> OTHER INFORMATION: Nucleic acid sequence of hz39D2.14 heavy chain
      variable region

<400> SEQUENCE: 88

```
caagtccaac tcgtgcagtc aggatctgaa ctgaagaaac ctggagcgag cgttaaggtt    60
tcctgcaagg ccagcggcta tacgttcact aactatggtg tcaactgggt gagacaggca   120
cccggccagg gcctggagtg gatgggttgg atcaatactc acacagggga accaacatat   180
gctgaggagt tcaaaggacg gtttgttttt agtctggaca cctccgtgtc taccgcctac   240
ctgcagattt ccagccttaa agcagaggac actgctgtat actactgtgc cagagacgag   300
tactatgtga ggaccgatta ctggggggcag gggaccaccg tgacagtctc aagt         354
```

<210> SEQ ID NO 89
<211> LENGTH: 448
<212> TYPE: PRT
<213> ORGANISM: Artificial Sequence
<220> FEATURE:
<223> OTHER INFORMATION: Amino acid sequence of hz39D2.14 heavy chain

<400> SEQUENCE: 89

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
```

```
            85                  90                  95
Ala Arg Asp Glu Tyr Tyr Val Arg Thr Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 90
<211> LENGTH: 1344
<212> TYPE: DNA
<213> ORGANISM: Artificial Sequence
<220> FEATURE:
<223> OTHER INFORMATION: Nucleic acid sequence of hz39D2.14 heavy chain

<400> SEQUENCE: 90
caagtccaac tcgtgcagtc aggatctgaa ctgaagaaac ctggagcgag cgttaaggtt    60

```
tcctgcaagg ccagcggcta tacgttcact aactatggtg tcaactgggt gagacaggca    120
cccggccagg gcctggagtg gatgggttgg atcaatactc acacagggga accaacatat    180
gctgaggagt tcaaaggacg gtttgttttt agtctggaca cctccgtgtc taccgcctac    240
ctgcagattt ccagccttaa agcagaggac actgctgtat actactgtgc cagagacgag    300
tactatgtga ggaccgatta ctgggggcag gggaccaccg tgacagtctc aagtgcctcc    360
accaagggcc cctccgtgtt ccctctggcc cctccagca agtccacctc tggcggcaca    420
gccgccctgg gctgcctggt gaaagactac ttccccgagc ccgtgaccgt gtcctggaac    480
tctggcgccc tgacctccgg cgtgcacacc ttccctgccg tgctgcagtc ctccggcctg    540
tactccctgt cctccgtggt gaccgtgccc tccagctctc tgggcaccca gacctacatc    600
tgtaacgtga accacaagcc ctccaacacc aaggtggaca gaaggtggaa cccaagtcc     660
tgcgacaaga cccacacctg tccccctgc cctgccctg aactgctggg cggaccttcc     720
gtgttcctgt tccccccaaa gcccaaggac accctgatga tctcccggac ccccgaagtg    780
acctgcgtgg tggtggacgt gtcccacgag gaccctgaag tgaagttcaa ttggtacgtg    840
gacggcgtgg aagtgcacaa tgccaagacc aagcccagag gaacagta caactccacc     900
taccgggtgg tgtctgtgct gaccgtgctg caccaggact ggctgaacgg caagaatac    960
aagtgcaaag tctccaacaa ggccctgcct gcccccatcg aaaagaccat ctccaaggcc   1020
aagggccagc cccgcgagcc ccaggtgtac accctgcccc ctagccggga cgagctgacc   1080
aagaaccagg tgtccctgac ctgtctggtg aaaggcttct accctccga cattgccgtg   1140
gaatgggagt ccaacggcca gcccgagaac aactacaaga ccaccccccc tgtgctggac   1200
tccgacggct cattcttcct gtactccaag ctgaccgtgg acaagtcccg gtggcagcag   1260
ggcaacgtgt tctcctgctc cgtgatgcac gaggccctgc acaaccacta cacccagaag   1320
tccctgtccc tgagccccgg caag                                          1344
```

<210> SEQ ID NO 91
<211> LENGTH: 107
<212> TYPE: PRT
<213> ORGANISM: Artificial Sequence
<220> FEATURE:
<223> OTHER INFORMATION: Amino acid sequence of hz39D2.14 light chain
      variable region

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95

Thr Phe Gly Gln Gly Thr Lys Val Glu Ile Lys
            100                 105

<210> SEQ ID NO 92

<211> LENGTH: 321
<212> TYPE: DNA
<213> ORGANISM: Artificial Sequence
<220> FEATURE:
<223> OTHER INFORMATION: Nucleic acid sequence of hz39D2.14 light chain variable region

<400> SEQUENCE: 92

```
cggaccgtgg ccgctccctc cgtgttcatc ttcccaccct ccgacgagca gctgaagtcc    60
ggcaccgcca gcgtggtctg cctgctgaac aacttctacc ccgcgaggc caaggtgcag   120
tggaaggtgg acaacgccct gcagtccggc aactcccagg aatccgtcac cgagcaggac   180
tccaaggaca gcacctactc cctgtcctcc accctgaccc tgtccaaggc cgactacgag   240
aagcacaagg tgtacgcctg cgaagtgacc caccagggcc tgtccagccc cgtgaccaag   300
tccttcaacc ggggcgagtg c                                             321
```

<210> SEQ ID NO 93
<211> LENGTH: 214
<212> TYPE: PRT
<213> ORGANISM: Artificial Sequence
<220> FEATURE:
<223> OTHER INFORMATION: Amino acid sequence of hz39D2.14 light chain

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 642
<212> TYPE: DNA
<213> ORGANISM: Artificial Sequence
<220> FEATURE:

<223> OTHER INFORMATION: Nucleic acid sequence of hz39D2.14 light chain

<400> SEQUENCE: 94

```
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctgcaa tacgatgagt tcccatggac cttcggccag     300
ggcaccaagg tggagattaa acggaccgtg gccgctccct ccgtgttcat cttcccaccc     360
tccgacgagc agctgaagtc cggcaccgcc agcgtggtct gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga gaagcacaag gtgtacgcct gcgaagtgac ccaccagggc     600
ctgtccagcc ccgtgaccaa gtccttcaac cggggcgagt gc                         642
```

<210> SEQ ID NO 95
<211> LENGTH: 118
<212> TYPE: PRT
<213> ORGANISM: Artificial Sequence
<220> FEATURE:
<223> OTHER INFORMATION: Amino acid sequence of hz39D2.22 heavy chain
    variable region

<400> SEQUENCE: 95

```
Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Val Asn Trp Val Arg Gln Ala Pro Gly Gln Gly Leu Glu Trp Met
        35                  40                  45
Gly Trp Ile Asn Thr His Thr Gly Glu Pro Thr Tyr Ala Glu Glu Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Asp Glu Tyr Tyr Val Arg Val Asp Tyr Trp Gly Gln Gly Thr
            100                 105                 110
Thr Val Thr Val Ser Ser
        115
```

<210> SEQ ID NO 96
<211> LENGTH: 354
<212> TYPE: DNA
<213> ORGANISM: Artificial Sequence
<220> FEATURE:
<223> OTHER INFORMATION: Nucleic acid sequence of hz39D2.22 heavy chain
    variable region

<400> SEQUENCE: 96

```
caagtccaac tcgtgcagtc aggatctgaa ctgaagaaac ctggagcgag cgttaaggtt      60
tcctgcaagg ccagcggcta cgttcact aactatggtg tcaactgggt gagacaggca      120
cccggccagg gctggagtg gatgggttgg atcaatactc acacagggga accaacatat     180
gctgaggagt tcaaaggacg gtttgttttt agtctggaca cctccgtgtc taccgcctac     240
```

```
ctgcagattt ccagccttaa agcagaggac actgctgtat actactgtgc cagagacgag    300
tactatgtga gggtggatta ctgggggcag gggaccaccg tgacagtctc aagt           354
```

<210> SEQ ID NO 97
<211> LENGTH: 448
<212> TYPE: PRT
<213> ORGANISM: Artificial Sequence
<220> FEATURE:
<223> OTHER INFORMATION: Amino acid sequence of hz39D2.22 heavy chain

<400> SEQUENCE: 97

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Glu Tyr Tyr Val Arg Val Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
```

```
                 340              345              350
Pro Pro Ser Arg Asp Glu Leu Thr Lys Asn Gln Val Ser Leu Thr Cys
            355                  360              365

Leu Val Lys Gly Phe Tyr Pro Ser Asp Ile Ala Val Glu Trp Glu Ser
        370              375              380

Asn Gly Gln Pro Glu Asn Asn Tyr Lys Thr Thr Pro Pro Val Leu Asp
385              390              395              400

Ser Asp Gly Ser Phe Phe Leu Tyr Ser Lys Leu Thr Val Asp Lys Ser
                405              410              415

Arg Trp Gln Gln Gly Asn Val Phe Ser Cys Ser Val Met His Glu Ala
            420              425              430

Leu His Asn His Tyr Thr Gln Lys Ser Leu Ser Leu Ser Pro Gly Lys
        435              440              445
```

<210> SEQ ID NO 98
<211> LENGTH: 1344
<212> TYPE: DNA
<213> ORGANISM: Artificial Sequence
<220> FEATURE:
<223> OTHER INFORMATION: Nucleic acid sequence of hz39D2.22 heavy chain

<400> SEQUENCE: 98

```
caagtccaac tcgtgcagtc aggatctgaa ctgaagaaac ctggagcgag cgttaaggtt      60
tcctgcaagg ccagcggcta tacgttcact aactatggtg tcaactgggt gagacaggca     120
cccggccagg gcctggagtg gatgggttgg atcaatactc acacagggga accaacatat     180
gctgaggagt tcaaaggacg gtttgttttt agtctggaca cctccgtgtc taccgcctac     240
ctgcagattt ccagccttaa agcagaggac actgctgtat actactgtgc cagagacgag     300
tactatgtga gggtggatta ctgggggcag gggaccaccg tgacagtctc aagtgcctcc     360
accaagggcc cctccgtgtt ccctctggcc cctccagca agtccacctc tggcggcaca     420
gccgccctgg gctgcctggt gaaagactac ttccccgagc ccgtgaccgt gtcctggaac     480
tctggcgccc tgacctccgg cgtgcacacc ttcctgccg tgctgcagtc ctccggcctg     540
tactccctgt cctccgtggt gaccgtgccc tccagctctc tgggcaccca gacctacatc     600
tgtaacgtga accacaagcc ctccaacacc aaggtggaca gaaggtgga acccaagtcc     660
tgcgacaaga cccacacctg tccccccttg cctgccccg aactgctggg cggaccttcc     720
gtgttcctgt tcccccaaa gcccaaggac accctgatga tctcccggac ccccgaagtg     780
acctgcgtgg tggtggacgt gtcccacgag accctgaag tgaagttcaa ttggtacgtg     840
gacggcgtgg aagtgcacaa tgccaagacc aagcccagag aggaacagta caactccacc     900
taccgggtgg tgtctgtgct gaccgtgctg caccaggact ggctgaacgg caaagaatac     960
aagtgcaaag tctccaacaa ggccctgcct gcccccatcg aaaagaccat ctccaaggcc    1020
aagggccagc ccgcgagcc ccaggtgtac accctgcccc ctagccggga cgagctgacc    1080
aagaaccagg tgtccctgac ctgtctggtg aaaggcttct acccctccga cattgccgtg    1140
gaatgggagt ccaacggcca gcccgagaac aactacaaga ccaccccccc tgtgctggac    1200
tccgacggct cattcttcct gtactccaag ctgaccgtgg acaagtcccg gtggcagcag    1260
ggcaacgtgt tctcctgctc cgtgatgcac gaggccctgc acaaccacta cacccagaag    1320
tccctgtccc tgagccccgg caag                                           1344
```

<210> SEQ ID NO 99
<211> LENGTH: 107

```
<212> TYPE: PRT
<213> ORGANISM: Artificial Sequence
<220> FEATURE:
<223> OTHER INFORMATION: Amino acid sequence of hz39D2.22 light chain
      variable region

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Glu Leu Asp Glu Phe Pro Trp
                85                  90                  95

Thr Phe Gly Gln Gly Thr Lys Val Glu Ile Lys
            100                 105

<210> SEQ ID NO 100
<211> LENGTH: 321
<212> TYPE: DNA
<213> ORGANISM: Artificial Sequence
<220> FEATURE:
<223> OTHER INFORMATION: Nucleic acid sequence of hz39D2.22 light chain
      variable region

<400> SEQUENCE: 100
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctggag ctcgatgagt tcccatggac cttcggccag     300
ggcaccaagg tggagattaa a                                               321

<210> SEQ ID NO 101
<211> LENGTH: 214
<212> TYPE: PRT
<213> ORGANISM: Artificial Sequence
<220> FEATURE:
<223> OTHER INFORMATION: Amino acid sequence of hz39D2.22 light chain

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Glu Leu Asp Glu Phe Pro Trp
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 642
<212> TYPE: DNA
<213> ORGANISM: Artificial Sequence
<220> FEATURE:
<223> OTHER INFORMATION: Nucleic acid sequence of hz39D2.22 light chain

<400> SEQUENCE: 102
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctggag ctcgatgagt tcccatggac cttcggccag     300
ggcaccaagg tggagattaa acggaccgtg gccgctccct ccgtgttcat cttcccaccc     360
tccgacgagc agctgaagtc cggcaccgcc agcgtggtct gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga aagcacaag gtgtacgcct gcgaagtgac ccaccagggc     600
ctgtccagcc ccgtgaccaa gtccttcaac cggggcgagt gc                        642

<210> SEQ ID NO 103
<211> LENGTH: 118
<212> TYPE: PRT
<213> ORGANISM: Artificial Sequence
<220> FEATURE:
<223> OTHER INFORMATION: Amino acid sequence of hz39D2.23 heavy chain
      variable region

<400> SEQUENCE: 103

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60
```

```
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Glu Tyr Tyr Val Arg Val Asp Tyr Trp Gly Gln Gly Thr
            100                 105                 110

Thr Val Thr Val Ser Ser
        115

<210> SEQ ID NO 104
<211> LENGTH: 354
<212> TYPE: DNA
<213> ORGANISM: Artificial Sequence
<220> FEATURE:
<223> OTHER INFORMATION: Nucleic acid sequence of hz39D2.23 heavy chain
      variable region

<400> SEQUENCE: 104
caagtccaac tcgtgcagtc aggatctgaa ctgaagaaac ctggagcgag cgttaaggtt     60
tcctgcaagg ccagcggcta tacgttcact aactatggtg tcaactgggt gagacaggca    120
cccggccagg gcctggagtg gatgggttgg atcaatactc acacagggga accaacatat    180
gctgaggagt tcaaggacg gtttgttttt agtctggaca cctccgtgtc taccgcctac    240
ctgcagattt ccagccttaa agcagaggac actgctgtat actactgtgc cagagacgag    300
tactatgtga gggtggatta ctgggggcag ggaccaccg tgacagtctc aagt           354

<210> SEQ ID NO 105
<211> LENGTH: 448
<212> TYPE: PRT
<213> ORGANISM: Artificial Sequence
<220> FEATURE:
<223> OTHER INFORMATION: Amino acid sequence of hz39D2.23 heavy chain

<400> SEQUENCE: 105

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
             20                  25                  30

Gly Val Asn Trp Val Arg Gln Ala Pro Gly Gln Gly Leu Glu Trp Met
         35                  40                  45

Gly Trp Ile Asn Thr His Thr Gly Glu Pro Thr Tyr Ala Glu Glu Phe
     50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Glu Tyr Tyr Val Arg Val Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 106
<211> LENGTH: 1344
<212> TYPE: DNA
<213> ORGANISM: Artificial Sequence
<220> FEATURE:
<223> OTHER INFORMATION: Nucleic acid sequence of hz39D2.23 heavy chain

<400> SEQUENCE: 106
caagtccaac tcgtgcagtc aggatctgaa ctgaagaaac tggagcgag cgttaaggtt     60 tcctgcaagg ccagcggcta tacgttcact aactatggtg tcaactgggt gagacaggca    120
cccggccagg gctggagtg gatgggttgg atcaatactc acacagggga accaacatat    180
gctgaggagt tcaaggacg gtttgttttt agtctggaca cctccgtgtc taccgcctac    240
ctgcagattt ccagccttaa agcagaggac actgctgtat actactgtgc cagagacgag    300
tactatgtga ggtggattac tggggggcag gggaccaccg tgacagtctc aagtgcctcc    360
accaagggcc cctccgtgtt ccctctggcc ccctccagca gtccacctc tggcggcaca    420 gccgccctgg gctgcctggt gaaagactac ttccccgagc ccgtgaccgt gtcctggaac    480
tctggcgccc tgacctccgg cgtgcacacc ttccctgccg tgctgcagtc ctccggcctg    540
```

```
tactccctgt cctccgtggt gaccgtgccc tccagctctc tgggcaccca gacctacatc    600
tgtaacgtga accacaagcc ctccaacacc aaggtggaca agaaggtgga acccaagtcc    660
tgcgacaaga cccacacctg tccccctgc cctgcccctg aactgctggg cggaccttcc    720
gtgttcctgt tcccccaaa gcccaaggac accctgatga tctcccggac ccccgaagtg    780
acctgcgtgg tggtggacgt gtcccacgag gaccctgaag tgaagttcaa ttggtacgtg    840
gacggcgtgg aagtgcacaa tgccaagacc aagcccagag aggaacagta caactccacc    900
taccgggtgg tgtctgtgct gaccgtgctg caccaggact ggctgaacgg caagaatac    960 aagtgcaaag tctccaacaa ggccctgcct gcccccatcg aaaagaccat ctccaaggcc   1020
aagggccagc ccgcgagcc ccaggtgtac accctgcccc ctagccggga cgagctgacc   1080
aagaaccagg tgtccctgac ctgtctggtg aaaggcttct accctccga cattgccgtg   1140 gaatgggagt ccaacggcca gccgagaac aactacaaga ccacccccc tgtgctggac   1200 tccgacggct cattcttcct gtactccaag ctgaccgtgg acaagtcccg gtggcagcag   1260
ggcaacgtgt tctcctgctc cgtgatgcac gaggccctgc acaaccacta cacccagaag   1320
tccctgtccc tgagccccgg caag                                           1344
```

<210> SEQ ID NO 107
<211> LENGTH: 107
<212> TYPE: PRT
<213> ORGANISM: Artificial Sequence
<220> FEATURE:
<223> OTHER INFORMATION: Amino acid sequence of hz39D2.23 light chain
      variable region

<400> SEQUENCE: 107

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Leu Asp Glu Phe Pro Trp
                85                  90                  95

Thr Phe Gly Gln Gly Thr Lys Val Glu Ile Lys
            100                 105
```

<210> SEQ ID NO 108
<211> LENGTH: 321
<212> TYPE: DNA
<213> ORGANISM: Artificial Sequence
<220> FEATURE:
<223> OTHER INFORMATION: Nucleic acid sequence of hz39D2.23 light chain
      variable region

<400> SEQUENCE: 108

```
gacattcaaa tgacacagtc tcccagctcc cttagtgctt cggtgggcga tcgggtgacc     60
ataacatgca aggcctcaca ggacatcaac agctatctct catggtttca gcagaagcca    120
ggaaaagcac ctaaaacgtt gatctacagg gccaatcgcc tcgttgacgg agtcccctcc    180
agattcagcg ggagtgggtc tggtcaggat tatactctga ccatctcctc tctgcagcct    240
```

```
gaagactttg ccacttacta ctgtctgcaa ctcgatgagt tcccatggac cttcggccag    300
ggcaccaagg tggagattaa a                                              321
```

<210> SEQ ID NO 109
<211> LENGTH: 214
<212> TYPE: PRT
<213> ORGANISM: Artificial Sequence
<220> FEATURE:
<223> OTHER INFORMATION: Amino acid sequence of hz39D2.23 light chain

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Leu Asp Glu Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 110
<211> LENGTH: 642
<212> TYPE: DNA
<213> ORGANISM: Artificial Sequence
<220> FEATURE:
<223> OTHER INFORMATION: Nucleic acid sequence of hz39D2.23 light chain

<400> SEQUENCE: 110

```
gacattcaaa tgacacagtc tcccagctcc cttagtgctt cggtgggcga tcgggtgacc    60
ataacatgca aggcctcaca ggacatcaac agctatctct catggttttca gcagaagcca   120 ggaaaagcac ctaaaacgtt gatctacagg gccaatcgcc tcgttgacgg agtcccctcc    180
agattcagcg ggagtgggtc tggtcaggat tatactctga ccatctcctc tctgcagcct    240
gaagactttg ccacttacta ctgtctgcaa ctcgatgagt tcccatggac cttcggccag    300
ggcaccaagg tggagattaa acggaccgtg gccgctccct ccgtgttcat cttcccaccc    360
tccgacgagc agctgaagtc cggcaccgcc agcgtggtct gcctgctgaa caacttctac    420
```

```
ccccgcgagg ccaaggtgca gtggaaggtg gacaacgccc tgcagtccgg caactcccag    480
gaatccgtca ccgagcagga ctccaaggac agcacctact ccctgtcctc cacctgacc     540 ctgtccaagg ccgactacga gaagcacaag gtgtacgcct gcgaagtgac ccaccagggc    600
ctgtccagcc ccgtgaccaa gtccttcaac cggggcgagt gc                       642
```